(12) United States Patent
Ram

(10) Patent No.: US 10,918,297 B2
(45) Date of Patent: Feb. 16, 2021

(54) MICROELECTRONIC SENSORS FOR NON-INVASIVE MONITORING OF PHYSIOLOGICAL PARAMETERS

(71) Applicant: EPITRONIC HOLDINGS PTE LTD., Singapore (SG)

(72) Inventor: Ayal Ram, Singapore (SG)

(73) Assignee: EPITRONIC HOLDINGS PTE LTD., Singapore (SG)

(*) Notice: Subject to any disclaimer, the term of this patent is extended or adjusted under 35 U.S.C. 154(b) by 106 days.

(21) Appl. No.: 16/082,515

(22) PCT Filed: Mar. 7, 2017

(86) PCT No.: PCT/IB2017/051320
§ 371 (c)(1),
(2) Date: Oct. 10, 2018

(87) PCT Pub. No.: WO2017/153907
PCT Pub. Date: Sep. 14, 2017

(65) Prior Publication Data
US 2019/0192022 A1 Jun. 27, 2019

Related U.S. Application Data

(63) Continuation of application No. 15/067,093, filed on Mar. 10, 2016, now abandoned, and a continuation of
(Continued)

(51) Int. Cl.
*A61B 5/04* (2006.01)
*H01L 29/778* (2006.01)
(Continued)

(52) U.S. Cl.
CPC .......... *A61B 5/0408* (2013.01); *A61B 1/2736* (2013.01); *A61B 3/16* (2013.01);
(Continued)

(58) Field of Classification Search
CPC ................ H01L 29/778; H01L 29/7781–7786
(Continued)

(56) References Cited

U.S. PATENT DOCUMENTS 3,991,365 A * 11/1976 Takeuchi ................. A61B 8/02
324/76.22
2002/0185655 A1 12/2002 Fahimulla et al.
(Continued)

FOREIGN PATENT DOCUMENTS

CN 102194867 A 9/2011
JP 2008047767 A 2/2008
(Continued)

OTHER PUBLICATIONS

Gassoumi et al. "Effect of surface passivation by SiN/SiO2 of AlGaN/GaN high-electron mobility transistors on Si substrate by deep level transient spectroscopy method" Semiconductor Physics and Technology (translated), 2013, vol. 47, Issue 7 2013. (Year: 2013).*
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, the PC-HEMT based microelectronic sensors are used in cardiovascular and pulmonary monitoring, detection and measurements of electrocardiography signals, detection of the primary heart activity signals and measurements of the central venous pressure and heart rate variability, measurements of the right and left atrium pressures, recording a phonocardiogram, detection of the S2-split phenomena, measurements of breath dynamics and lung activity diagnostics, monitoring the brain activity and
(Continued)

measuring and monitoring electrical signals associated with an electroencephalogram, and eye pressure diagnostics.

21 Claims, 53 Drawing Sheets
(45 of 53 Drawing Sheet(s) Filed in Color)

Related U.S. Application Data application No. 15/157,285, filed on May 17, 2016, now abandoned.

(51) Int. Cl.

| | | |
|---|---|---|
| A61B 5/0408 | (2006.01) | |
| A61B 7/00 | (2006.01) | |
| A61B 5/00 | (2006.01) | |
| G01N 27/414 | (2006.01) | |
| A61B 1/273 | (2006.01) | |
| A61B 3/16 | (2006.01) | |
| A61B 5/021 | (2006.01) | |
| A61B 5/0452 | (2006.01) | |
| A61B 5/0478 | (2006.01) | |
| A61B 5/11 | (2006.01) | |
| A61B 7/04 | (2006.01) | |
| H01L 29/20 | (2006.01) | |
| H01L 29/205 | (2006.01) | |
| A61B 5/08 | (2006.01) | |

(52) U.S. Cl.
CPC .............. *A61B 5/00* (2013.01); *A61B 5/0006* (2013.01); *A61B 5/021* (2013.01); *A61B 5/04017* (2013.01); *A61B 5/0452* (2013.01); *A61B 5/0478* (2013.01); *A61B 5/1102* (2013.01); *A61B 7/00* (2013.01); *A61B 7/045* (2013.01); *G01N 27/414* (2013.01); *H01L 29/2003* (2013.01); *H01L 29/205* (2013.01); *H01L 29/7786* (2013.01); *A61B 5/08* (2013.01); *A61B 2562/0204* (2013.01); *A61B 2562/028* (2013.01); *A61B 2562/029* (2013.01); *A61B 2562/0209* (2013.01); *A61B 2562/0247* (2013.01); *A61B 2562/0261* (2013.01); *A61B 2562/043* (2013.01); *A61B 2562/12* (2013.01); *A61B 2562/164* (2013.01)

(58) Field of Classification Search
USPC .................................................. 257/194–195
See application file for complete search history.

(56) References Cited

U.S. PATENT DOCUMENTS

| | | | |
|---|---|---|---|
| 2004/0144991 A1* | 7/2004 | Kikkawa | H01L 29/66462 257/103 |
| 2004/0262636 A1* | 12/2004 | Yang | B82Y 10/00 257/200 |
| 2007/0114568 A1* | 5/2007 | Simin | H01L 29/94 257/192 |
| 2008/0265258 A1* | 10/2008 | Tanabe | H01L 29/7787 257/76 |
| 2009/0072272 A1* | 3/2009 | Suh | H01L 29/1066 257/194 |
| 2011/0199102 A1* | 8/2011 | Garcia | G01N 27/4148 324/658 |
| 2011/0213271 A1* | 9/2011 | Telfort | A61B 7/003 600/586 |
| 2014/0203797 A1* | 7/2014 | Stivoric | F24F 11/30 324/76.11 |
| 2014/0323895 A1 | 10/2014 | Vitushinsky et al. | |
| 2015/0002135 A1* | 1/2015 | Moyer | G01R 19/14 324/119 |
| 2016/0064600 A1* | 3/2016 | Kuroda | H01L 29/7786 257/13 |
| 2017/0294528 A1* | 10/2017 | Ren | H01L 29/0657 |

FOREIGN PATENT DOCUMENTS

| | | |
|---|---|---|
| TW | I344205 B | 6/2011 |
| WO | 2009137768 A2 | 11/2009 |

OTHER PUBLICATIONS

Corekci et al. "Surface Morphology of Al0.3Ga0.7N/Al2O3—High Electron Mobility Transistor Structure" Journal of Nanoscience and Nanotechnology, vol. 8 Issue: 2 pp. 640-644, Feb. 2008 (Year: 2008).*
International Search Report PCT/IB2017/051320 Completed May 31, 2017; dated Aug. 16, 2017 7 pages.
Written Opinion of the International Searching Authority PCT/IB2017/051320 dated Aug. 16, 2017 16 pages.

* cited by examiner

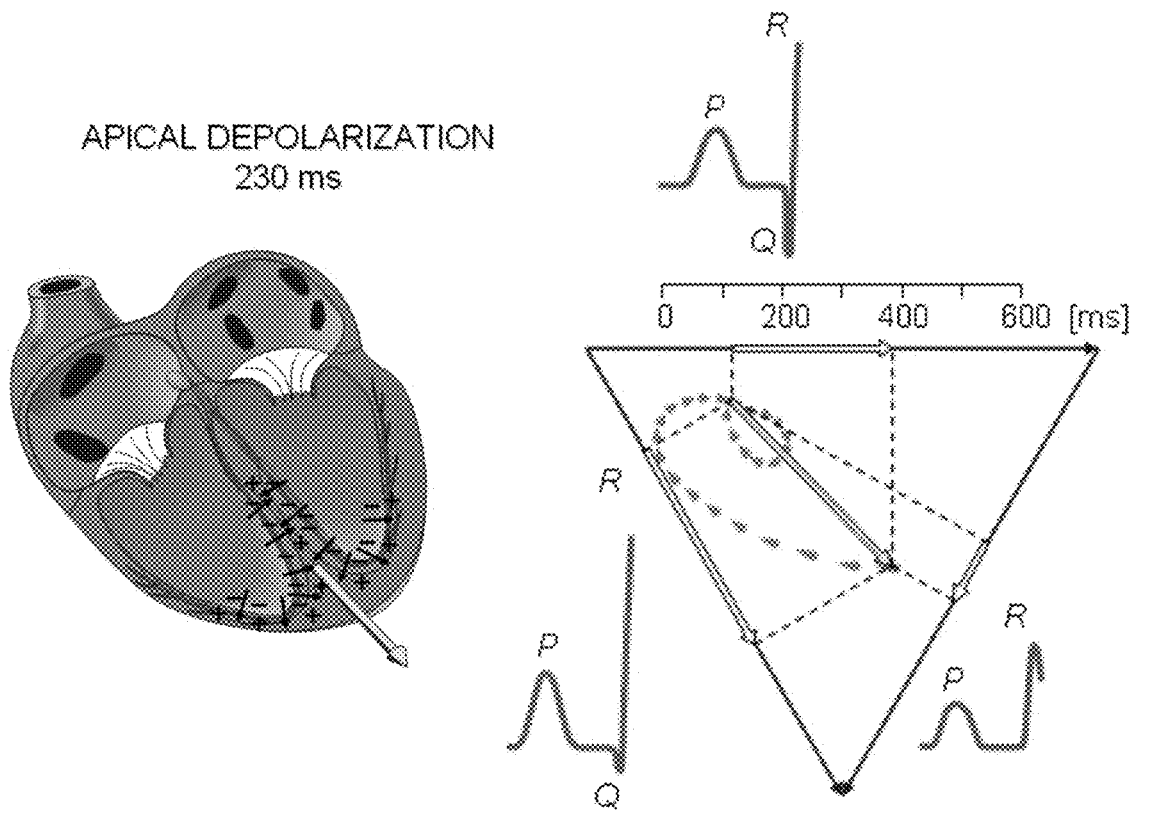
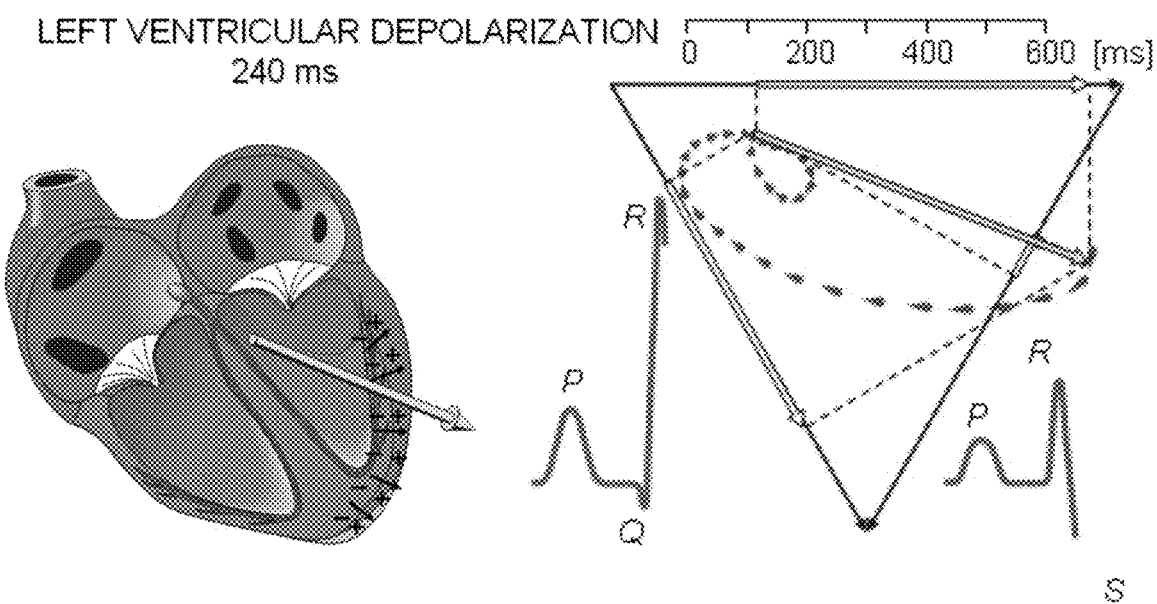
Fig. 1d (Prior Art)

LATE LEFT VENTRICULAR DEPOLARIZATION
250 ms
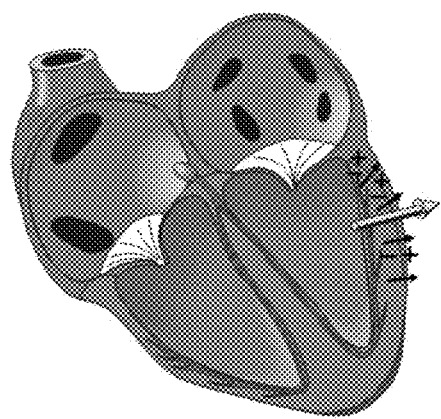
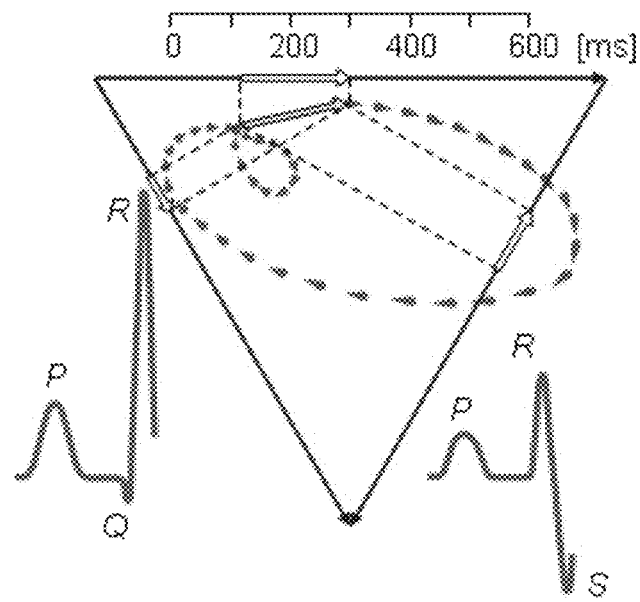
VENTRICLES DEPOLARIZED
350 ms
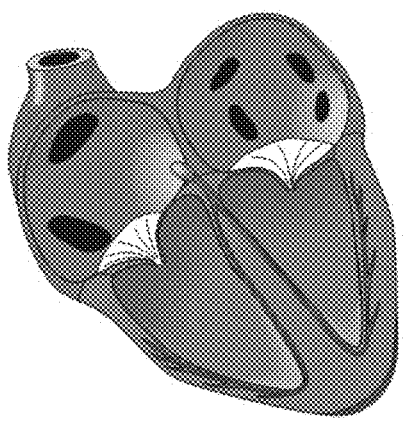
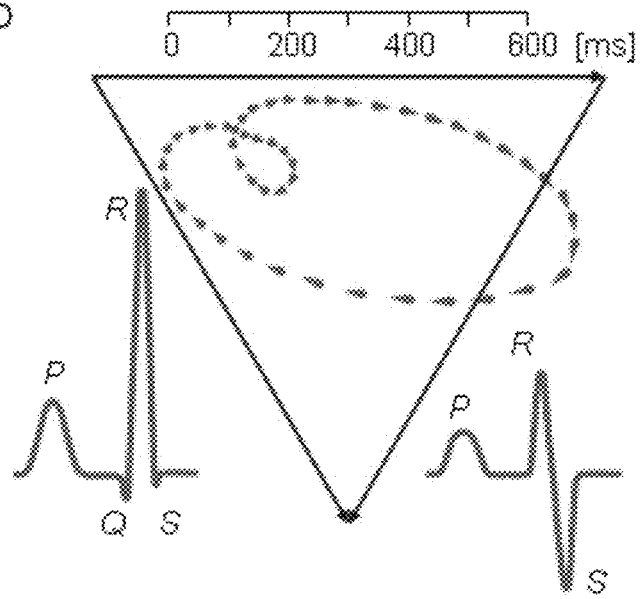
Fig. 1e (Prior Art)

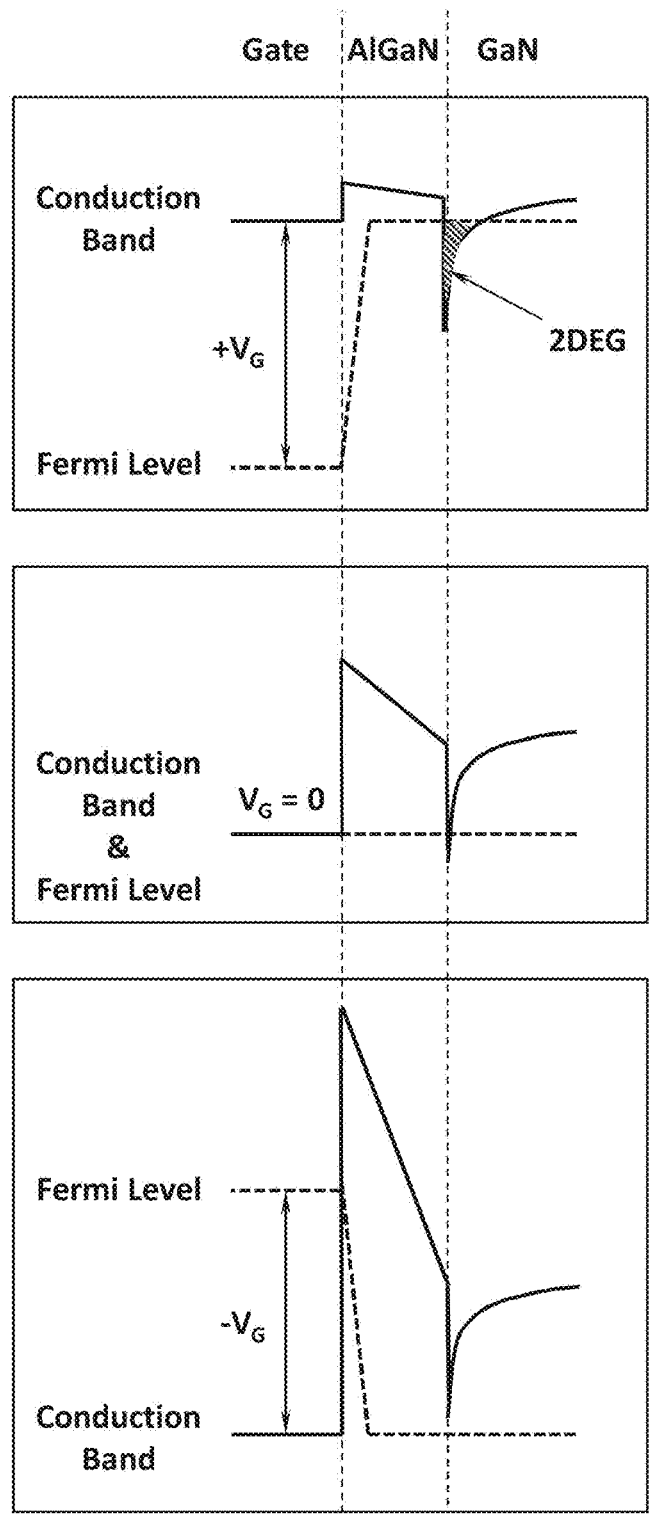

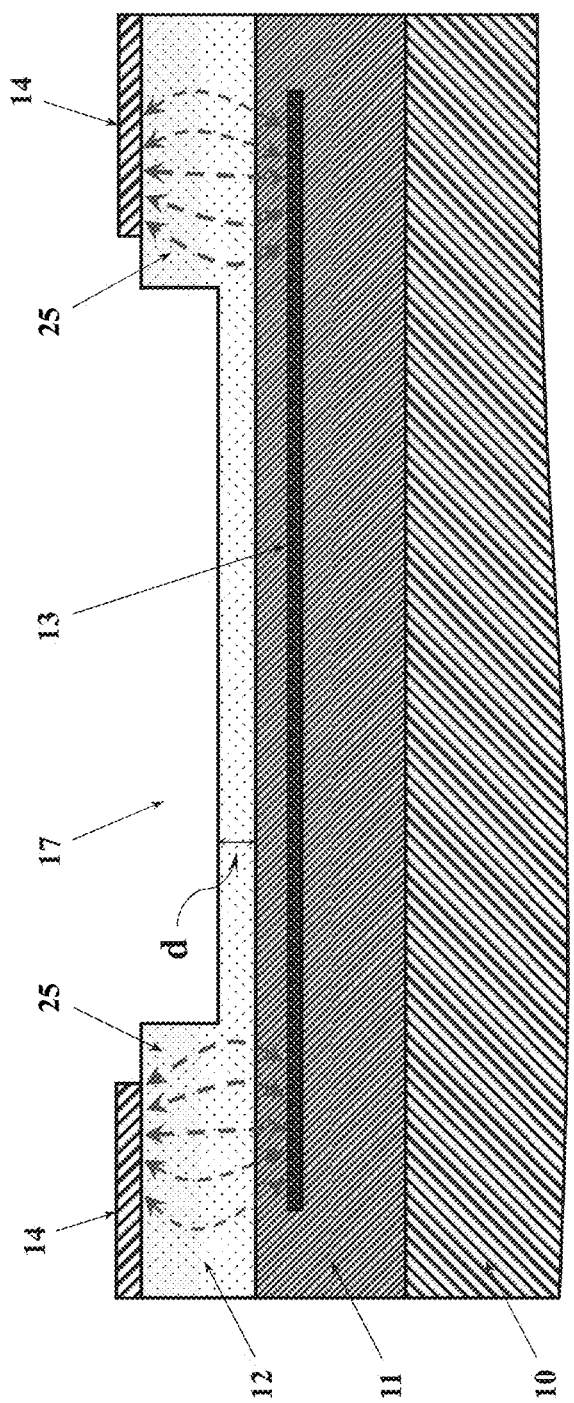

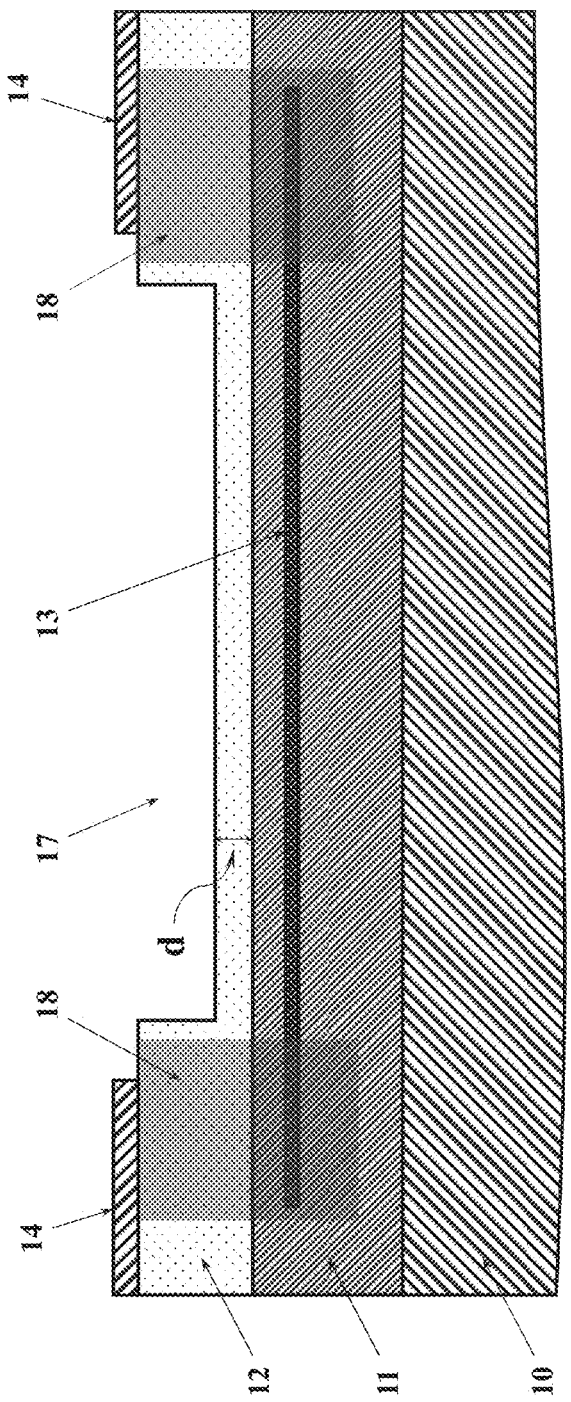

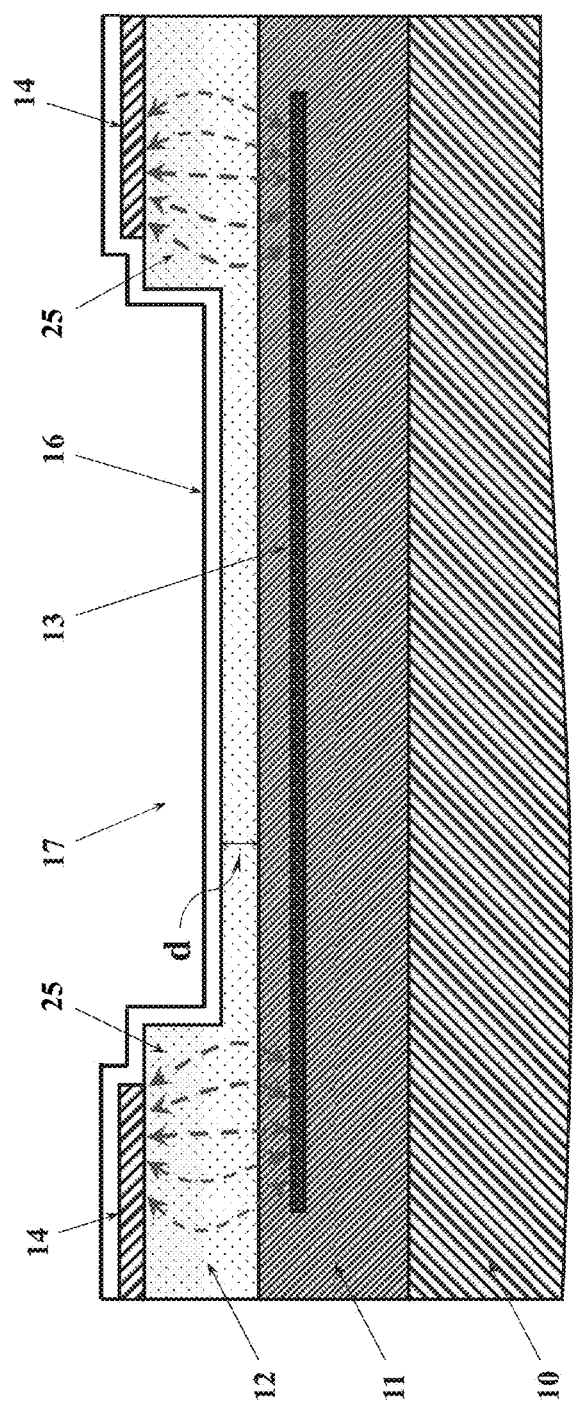

Fig. 7a        Ga-Face Polarity
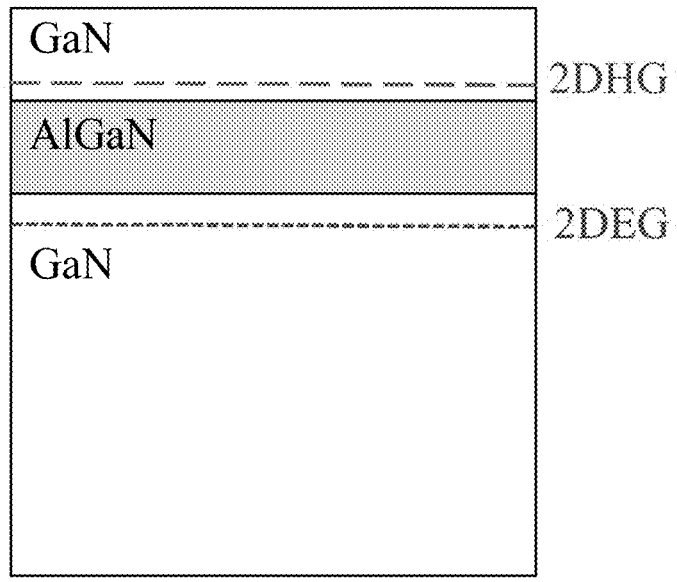
Fig. 7b        N-Face Polarity
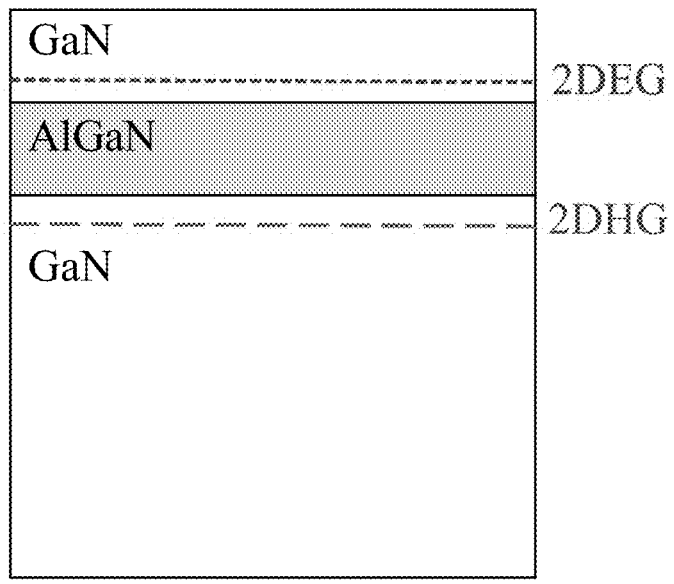

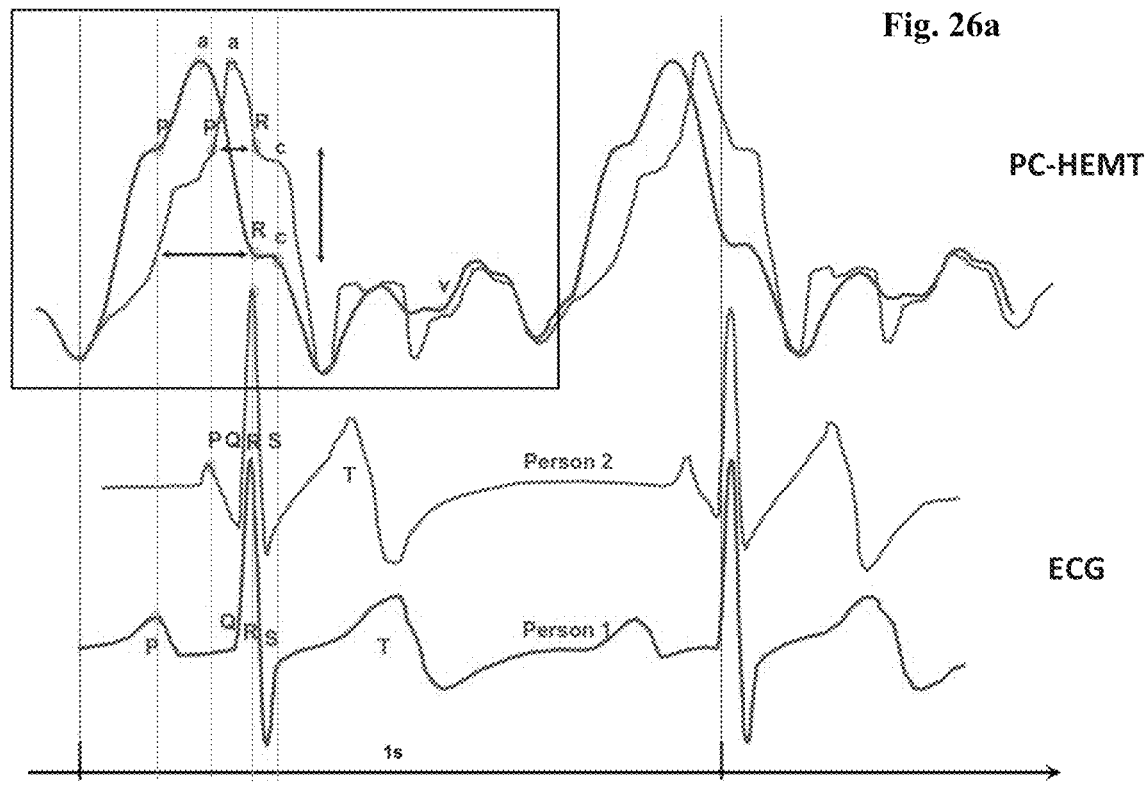
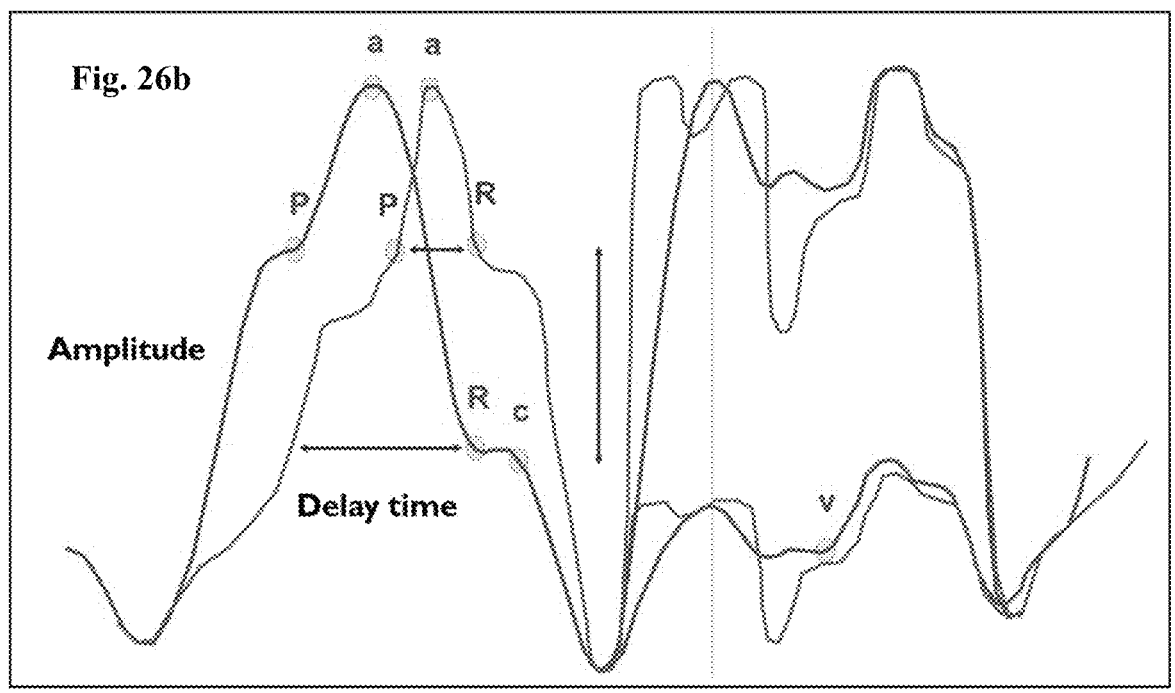

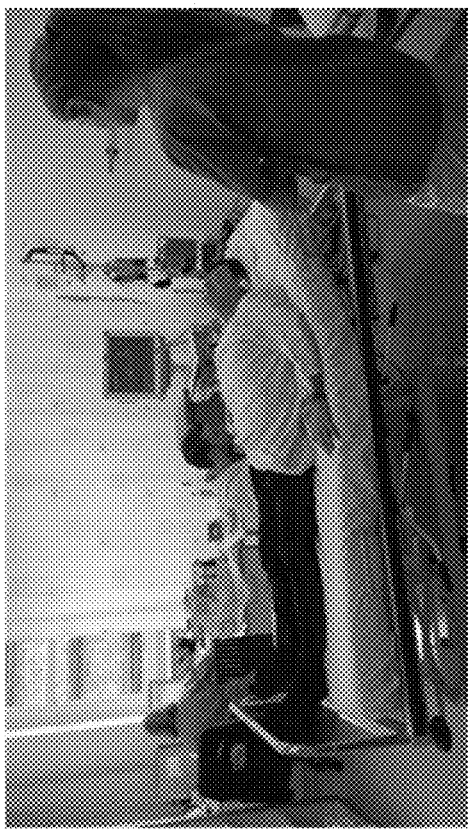
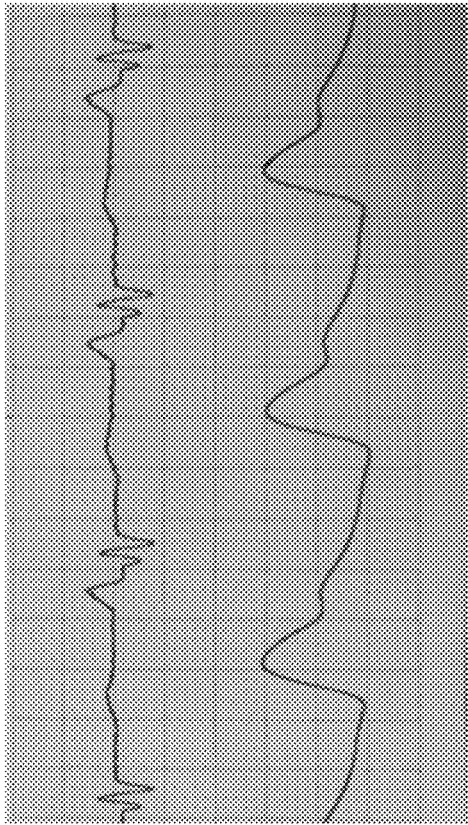
Fig. 30a

MICROELECTRONIC SENSORS FOR NON-INVASIVE MONITORING OF PHYSIOLOGICAL PARAMETERS

RELATED APPLICATIONS

This application is a National Phase of PCT Patent Application No. PCT/IB2017/051320 having International filing date of Mar. 7, 2017, which claims the benefit of priority of U.S. patent application Ser. No. 15/067,093 filed on Mar. 10, 2016 and U.S. patent application Ser. No. 15/157,285 filed on May 17, 2016. The contents of the above applications are all incorporated by reference as if fully set forth herein in their entirety.

TECHNICAL FIELD

The present application relates to the field of microelectronic sensors based on high-electron-mobility transistors and their use in detection and continuous monitoring of electrical signals generated by a human body. In particular, the present application relates to the open-gate pseudo-conductive high-electron-mobility transistors and their use in non-invasive monitoring of physiological parameters of a human body.

BACKGROUND

Human health state is determined by many self-interdependent physiological parameters. Not all of them are equally informative and important. Besides, not all of those parameters could be easily and precisely monitored, since measurement of them requires special conditions, expensive medical equipment and materials. While designing the overall monitoring system, it is necessary to assess not only importance of measured parameters but also techniques of their measurement and potentiality of implication into practical systems. Medical investigations have proven that the most important parameters are those that specify the work of heart and respiratory or pulmonary system.

Typical parameters that reflect the status of cardiovascular and respiratory or pulmonary systems to be monitored are cardiac output and primary heart activity associated with an electrocardiogram, central venous pressure, left and right atrium pressures, lung or pulmonary activity associated with a breath cycle, respiratory rate and volume, and brain activity associated with an electroencephalogram. Other physiological parameters that can be evaluated from the above parameters are stroke volume, breathing related changes of the stroke volume, peripheral vascular resistance, arterial compliance, breathing rate and amplitude (or tidal volume).

Cardiovascular and pulmonary systems are inherently multivariate closed-loop systems. Main physiological parameters of these system have a close interrelation mediated by various mechanical and neural mechanisms which can also be evaluated by monitoring brain activity. The autonomous nervous system controls different parts of this system by a continuous neural modulation causing small variations of the variables around their mean values. Breathing as an external stimulator is capable of modulating the hemodynamic parameters significantly. The relationship and interaction between the brain activity, blood circulation and breathing is very tight, which emphasizes the need of simultaneous monitoring and estimation of these systems in clinical work.

Currently, a number of different types of devices are available for monitoring human subjects in a non-invasive manner. For example, heart function can be monitored in a patient through the use of electrodes, which must be attached to the skin of the patient. Although non-invasive, such equipment is nevertheless uncomfortable for the patient, who is attached to a network of cables and wired sensors. In addition, such equipment is costly, limiting its use to hospitals, laboratories and other medical settings in which both the cost and the discomfort of the patient can be justified.

In general, non-invasive and continuous monitoring of a human subject is desired. In order to support regular monitoring of human subjects in their normal environment, for example at home or at the office, the equipment must be non-invasive and easy to use. For instance, such monitoring could be very useful as part of the overall health maintenance of a patient, and could be used in order to detect a deterioration in the physiological condition of the patient before a concomitant deterioration in the health becomes noticeable.

Typical equipment used in hospitals and laboratories is able to monitor at least one physiological parameter of a patient, without requiring the patient to perform any complicated actions and/or to operate complex devices. However, as mentioned above, it would be highly preferred for the equipment to be incorporated as part of the regular daily living routine of the user or patient, since the requirement for any additional or special actions on the part of the patient is likely to result in decreased compliance. In addition, the equipment should be robust yet inexpensive, for example a small wristband to attach a physiological sensor to the wrist of a user. A number of different types of such wristband devices, which will be specified below, are currently available, most of which are intended to be used as stand-alone devices to provide information about the user's own physical condition, mainly for heart rate and blood pressure.

Electrocardiography

It is always advisable to register heart work related physiological parameters when evaluating human health condition, since the heart work is associated with physiological functions of vital importance to the human body. The prime heart work related physiological parameters are heart work rate (pulse) and blood pressure. Electrocardiogram (ECG) is one of the most representative physiological characteristics of heart work.

Electrocardiography is the process of recording the electrical activity of the heart over a period of time using electrodes placed on a patient's body. These electrodes detect the tiny electrical changes on the skin that arise from the heart muscle polarisation and depolarizing during each heartbeat, and the recording is generated therefrom and/or by another device, such as an electrode reader.

Conventional electrocardiographs employ multiple (8-12) electrodes for measuring the electrical activity of the heart. Each electrode is placed on a patient at a particular location within some tolerance. From these electrodes, the overall magnitude of the heart's electrical potential is usually measured from twelve different angles ("leads") and is recorded over a period of time (usually 10 seconds). In this way, the overall magnitude and direction of the heart's electrical dipole is captured at each moment throughout the cardiac cycle. The obtained graph of voltage versus time produced by this non-invasive medical procedure is referred to as an electrocardiogram (ECG or EKG). Various conventional electrocardiographs include 3, 5, 15, 16, etc. leads.

During each heartbeat, a healthy heart has an orderly progression of depolarisation and polarisation that starts with pacemaker cells in the sinoatrial node, spreads out through the atrium, passes through the atrioventricular node down into the bundle of HIS and into the Purkinje fibres spreading down and to the left throughout the ventricles. This orderly pattern of depolarisation and polarisation gives rise to the characteristic ECG tracing.

Thus, ECG represents an absolutely essential method of medical diagnostics. The health medical information extracted from ECG is indispensable for direct determination of the heart function and many other vital body parameters such as heart diseases, atrial fibrillation, cholesterol clogging, heart attack prediction, hypertension and many others. ECG conveys a large amount of information about the structure of the heart and the function of its electrical conduction system. Among other things, ECG can be used to measure the rate and rhythm of heartbeats, the size and position of the heart chambers, the presence of any damage to the heart's muscle cells or conduction system, the effects of cardiac drugs, and the function of implanted pacemakers.

The possibility of continuous ECG detection in the daily life is extremely important and invaluable for predictive health care in the modern society, where the heart distress signals could be detected as early as possible. Pulse-watches measuring the heart rate from a single point on a wrist using photoplethysmography (pulse oximetry) have been recently commercialised. Tom-Tom® Runner Cardio and Mio® Alpha watches use photoplethysmography to continuously measure the hemodynamic blood waves and heart rate. Their principle of operation is based on pulse transit time method with additional ECG-signal for calculation of blood pressure.

Skin Surface Potential Along the Arm

An ECG is by definition a differential measurement. There is a gradient electric field distribution along the arm according to a bioelectric volume conductor body nature and to a dynamic electric field volume source representing the heart dipole function. This heart-dipole electric field creates a dynamic body surface potential map on the skin, which is measured differentially at least at two skin points representing the ECG signal.

As shown in FIGS. 1a-1f (Malmivuo and Plonsey, 1975), to obtain the maximal clearest amplitude of P-QRS-T heart cycle, the ECG signal is normally measured across the dipole according to Einthoven triangle dipole vector projection method. In this method, electrodes are connected to three limbs (left and right arms and left foot) to get a projection of the electrical dipole vector, which is generated by a heart during its depolarisation cycle. If there is some observed irregularity in electrical excitation of the heart, which can be caused by a cardiac infarct, the related electrical excitation is changing and the signal is moving to other directions. This irregularity will then be visible in the projection signal.

The ECG signal can be easily measured along the arm using a standard differential low noise amplifier. FIG. 2a schematically shows various ECG recording on the 17 marked body points relative to initial point "1". FIG. 2b shows voltage values (Q-to-R peak amplitude) recorded at marked electrode positions from 1 to 15 (positions 16 and 17 are hand and fingertip). FIG. 2c demonstrates three body surface potential maps during the 50-ms QRS-interval. The potential is colour coded onto the body surface. The distribution of the electrical field is computed with numerical methods outgoing from cardiac sources. The differential ECG signal is measured using the standard Ag/AgCl gel ECG electrodes when the reference electrode is placed on a patient's chest near his heart (point 1) and the second electrode is moving gradually to the direction of fingertips between points 2-16 accordingly.

At the electrode position 8 (elbow), the differential signal reaches a maximum value and remains constant till fingertips (position 16). This experimental observation originates from the nature of the electric field distribution within a body volume conductor shown in FIG. 2c and clearly evidenced in FIG. 2b. Since, the Q-to-R peak amplitude doesn't change in the wrist area (electrode positions 13-14), the signal distribution eminently hinders the actual ECG detection with the aforementioned wrist-watch devices (at the) based on pulse oximetry.

Therefore, there is a demand for a new type of sensors, which would be based on a different detection principle. The new sensors will be attached to a lower part of the limbs and provide a continuous single-point cardiovascular monitoring. Even more demand exists for cardiovascular sensors that do need to be attached to a body but can remotely monitor the cardiovascular activity.

Non-Differential Sensing Techniques

There are only two existing non-differential sensing techniques which are recently developed for cardiovascular monitoring on a chest or even on lower limbs. Nakayama et al (2011) and An et al (2012) described microelectronic CMOS-based magnetic field sensors based on giant magneto impedance (GMI). These types of microelectronic devices were able to detect the magnetocardiography (MCG)-single point signals from chest but failed to detect the MCG signal from wrist.

Kado et al (2010) described optoelectronic detectors changing their optical properties, such as reflectance, as a function of e-field magnitude. Such transducers have already found their application in personal RFID systems, for example RedTacton® NTT. However, the detection of a lower limb ECG signals based on a non-differential skin potential or remote cardiovascular monitoring still remains unproven and challenging.

Respiratory Physiological Parameters

Respiratory ensures permeation of the oxygen into the human body. Special medical equipment is required to register respiratory characteristics, so called respiratory or pulmonary physiological parameters. Those parameters featuring human health state consequently can be divided into three groups: volume parameters, respiratory system physical parameters (respiratory rate and other mechanical parameters of respiratory system) and parameters of gas metathesis within the lungs. Volume parameters, such as total lungs capacity, tidal breath and functional remaining capacity, characterise potential and functionality of human body parts that respond for respiratory functions. Physical parameters, such as respiratory rate and breath cycle, are related to mechanical model of respiratory or pulmonary system. Gas metathesis physiological parameters are related to gas penetration into human body and exhausting from it when breathing. All those parameters are interdependent and measurement of some of those parameters allows calculating the rest of them.

Both conventional and remote measurement of pulmonary system parameters traditionally uses respiratory masks, which are not much compatible with telemetric principles of measurement. Indirect mask-free methods evaluate respiratory parameters according some other physical body parameters, like recurrent impedance of human body tissues and others. The main problem is the accuracy of the results, since most of known methods are sensitive to human body movements and that introduces significant errors into respiratory parameters measurements.

Central Venous Pressure Monitoring

Central venous pressure (CVP) is the blood pressure formed in the thoracic vein, at the right atrium of the heart, and corresponds to the amount of blood pumped back to the heart. There is currently only one method to measure the pressure from the right atrium. This method utilises catheters and hence, invasive. Due to different catheter positions, the CVP data recorded from the same patient may be different. Information obtained on the atrium pressure is important for the diagnosis of many cardiovascular diseases. The atrium pressure actually represents the most stable and reliable pressure for monitoring. Moreover, the atrium pressure provides information on the pulmonary pressure which is required for diagnosis of pulmonary diseases, such as pulmonary hypertension recently shown to be one of the largest disease groups in the world. Using the aforementioned single-point cardiovascular sensing is the only non-invasive approach to continuous monitoring of the pulmonary pressure.

High Electron Mobility Transistor

The polarization doped high-electron-mobility transistor (HEMT) is a field effect transistor (FET) in which two layers of different bandgap and polarisation field are grown upon each other forming a hetero-junction structure. As a consequence of the discontinuity in the polarisation field, surface charges are created at the interface between the layers of the hetero-junction structure. If the induced surface charge is positive, electrons will tend to compensate the induced charge resulting in the formation of the channel. Since in the HEMT, the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

The HEMTs based on the layers of III-V semiconductor materials, such as gallium nitride (GaN) and aluminium gallium nitride (AlGaN), have recently been developed with a view to high-voltage and high-power switching applications. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor should be regulated.

FIGS. 3a-3c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage required to populate electrons at the interface between the GaN and AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 3a). This enables high population of the 2DEG channel electrons and hence, high conductivity. The HEMT is turned on in this case. However, when $V_G$ decreases to 0V (FIG. 3b), the Fermi level also drops with respect to the quantum well. As a result, much fewer electron energy levels are populated and the amount of the 2DEG channel electrons significantly decreases. When $V_G \ll V_T$ (FIG. 3c), all electron energy levels are above the Fermi level, and there is no 2DEG electrons below the gate. This situation is called "channel depletion", and the HEMT is turned off.

Many commercially available AlGaN/GaN-based HEMT structures have a negative $V_T$, resulting in a "normally-on" operation mode at 0V gate potential. They are called "depletion-mode transistors" and used in various power switching applications when the negative voltage must be applied on the gate in order to block the current. However, for safe operation at high voltage or high power density, in order to reduce the circuit complexity and eliminate standby power consumption, HEMTs with "normally-off" characteristics are preferred.

Several techniques to manufacture the normally-off HEMTs have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. The normally-off operation of the transistor is achieved once the depletion region reaches the interface and depletes the 2DEG channel at zero gate voltage. The major advantages of these HEMTs are relatively lower power consumption, lower noise and simpler drive circuits. These HEMTs are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves normally-off operation by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

SUMMARY

The present application describes embodiments of a method for monitoring physiological parameters of a human subject using a microelectronic sensor based on an open-gate pseudo-conductive high-electron mobility transistor (PC-HEMT). In some embodiments, a transistor comprises a substrate, on which a multilayer hetero-junction structure is deposited. In other embodiments, the multilayer hetero-junction structure is placed on free-standing membranes. This hetero-junction structure may comprise at least two layers, a buffer layer and a barrier layer, which are grown from III-V single-crystalline or polycrystalline semiconductor materials.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain, either ohmic or capacitively-coupled (non-ohmic) contacts are connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/

2DHG channel underneath, which is about 5-20 nm bellow metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:
(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor,
(ii) the surface of the top layer within the open gate area between the source and drain contacts has a roughness of about 0.2 nm or less, preferably 0.1 nm or less, more preferably 0.05 nm, and
(iii) the non-ohmic source and drain contacts for the capacitive coupling with the conductive 2DEG/2DHG channel optionally replace the ohmic contacts.

In some embodiments, the PC-HEMT multilayer hetero-junction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and $LaAlO_3/SrTiO_3$. In case of the GaN/AlGaN PC-HEMT, it has been surprisingly found that in the open gate area of the PC-HEMT, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

Further, in some embodiments, the present application provides sensors based on the PC-HEMT of the application for non-invasive and continuous cardiovascular and pulmonary monitoring, i.e. detecting, measuring and monitoring the electrocardiography signals and central venous pressure (CVP). They are also capable of breath monitoring and lung activity diagnostics and hence, can be used in pulmonary and respiratory related applications. In addition, these sensors can monitor the brain activity and measure and monitor electrical signals associated with an electroencephalogram (EEC). Further, the sensors of the invention can be used in eye pressure diagnostics.

Working principle of the PC-HEMT sensor of the application is based on ultra-high charge sensitivity at the sensor/tissue surface interface. Physically, the human heart represents a volume source of an electric dipole field acting within a volume electrolytic conductor represented by human body. Using the enormously high charge sensitivity, it is possible to record both processes: an appearance and wave (dynamic distribution) of an electrical heart dipole due to a heart muscle polarisation/depolarisation cycles, followed by corresponding mechanical movements of polarised heart parts in a real time. In a particular embodiment, the sensor of the present application is used for cardiovascular monitoring, the GUI of this sensor is programmed in such a way as to interpret the signal peaks obtained from the sensor, process their shape and time intervals, and correlate them with the corresponding ECG peak/point readings of P, Q, R, S, T and J peaks, and with related intervals between said points in the electrocardiogram.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures.

FIGS. 1a-1f show the Einthoven triangle and heart polarisation-depolarisation cycle according to the prior art.

FIG. 3 schematically shows the quantum well at three different biasing conditions: FIG. 3a: positive gate potential ($+V_G$) is much higher than threshold voltage ($V_T$), FIG. 3b: 0V gate potential, and FIG. 3c: negative gate potential ($-V_G$) is below threshold voltage ($V_T$).

FIG. 4c schematically shows a cross-sectional view of the PC-HEMT of an embodiment having non-ohmic (capacitively-coupled) contacts and no dielectric layer.

FIG. 4d schematically shows a cross-sectional view of the PC-HEMT of an embodiment with highly-doped source and drain areas.

FIG. 4f schematically shows a cross-sectional view of the PC-HEMT of an embodiment having non-ohmic (capacitively-coupled) contacts and a dielectric layer.

FIG. 7a schematically shows the formation of the 2DEG and 2DHG conducting channels in the Ga-face three-layer GaN/AlGaN/GaN PC-HEMT structure.

FIG. 7b schematically shows the formation of the 2DEG and 2DHG conducting channels in the N-face three-layer GaN/AlGaN/GaN PC-HEMT structure.

FIGS. 26a-26b show the comparison of normal (red) and abnormal (grey) cardiac signal shape from two patients.

FIG. 30a shows the ECG and PPG print-outs from the medical catheter control-unit for the second patient and his laboratory environment during the test.

DETAILED DESCRIPTION

Figure 1A:
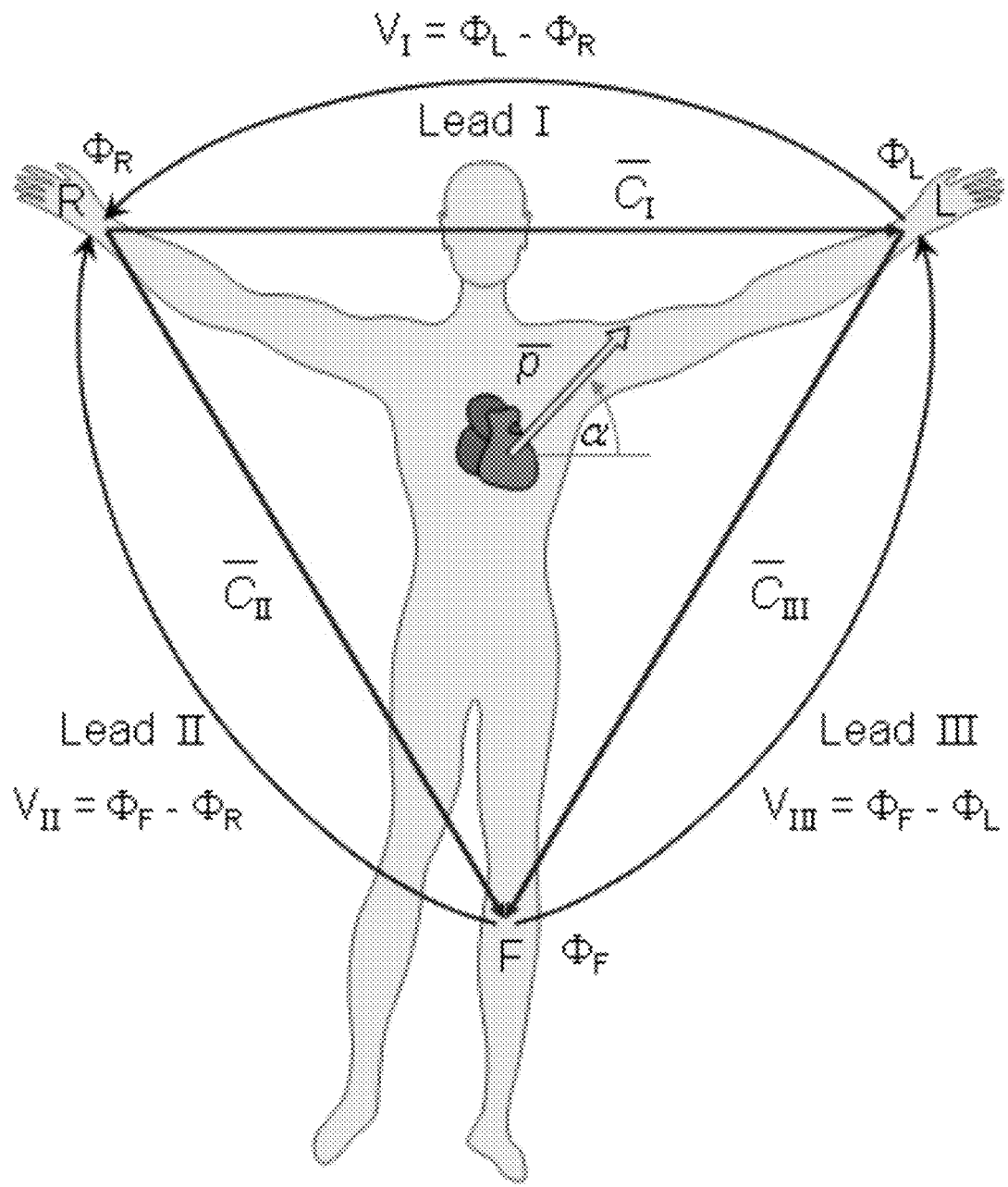
Figure 1B:
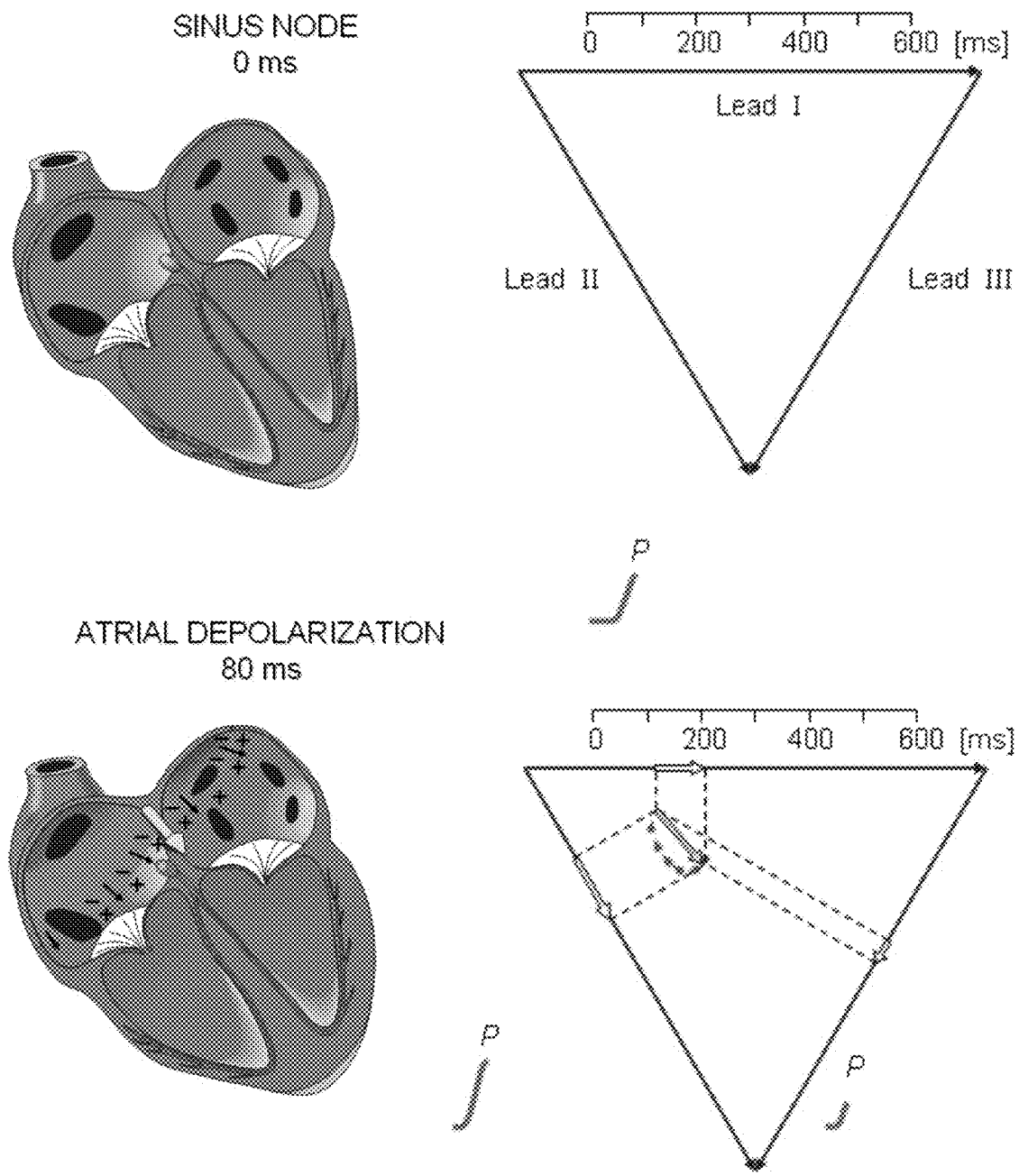
Figure 1C:
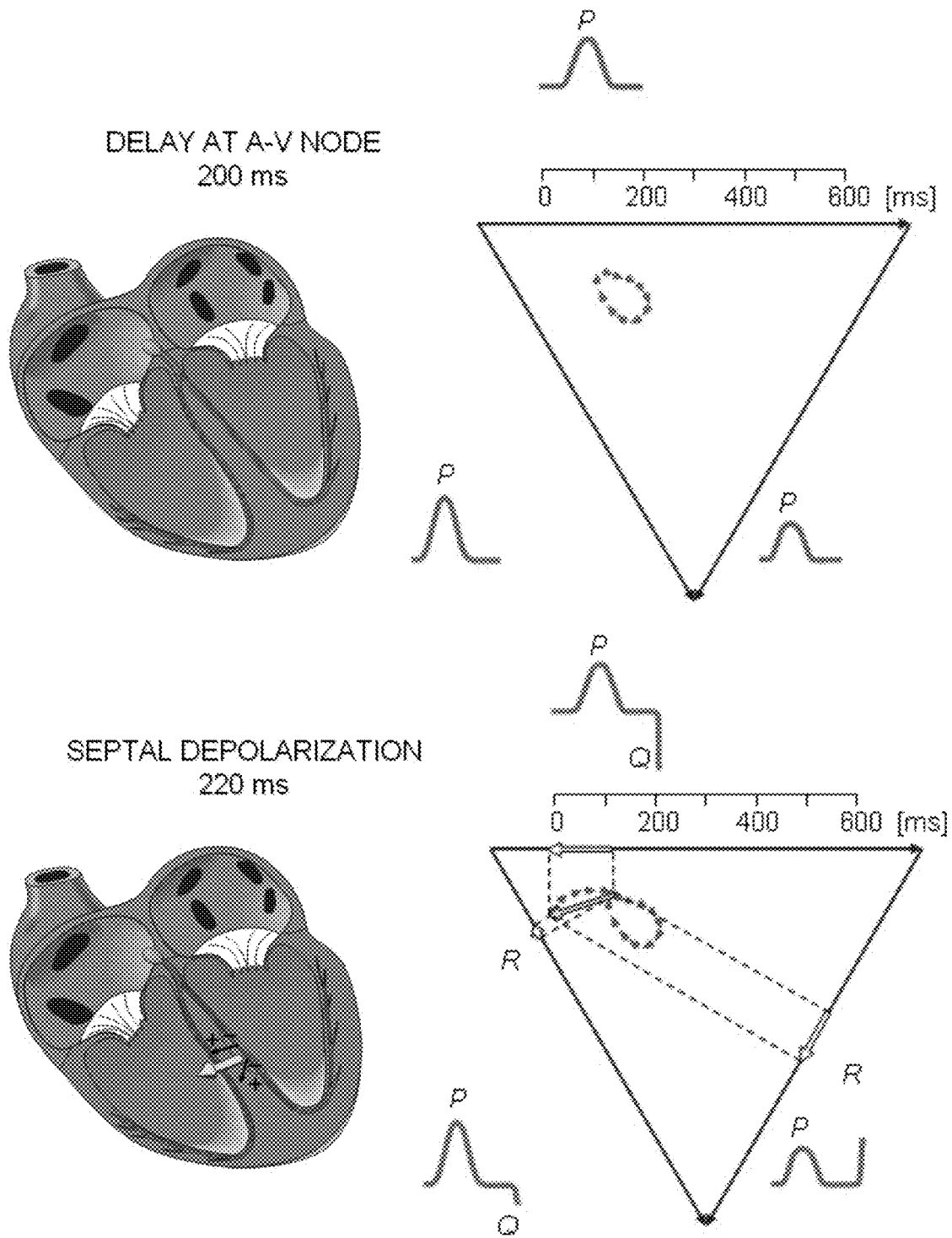
Figure 1F:
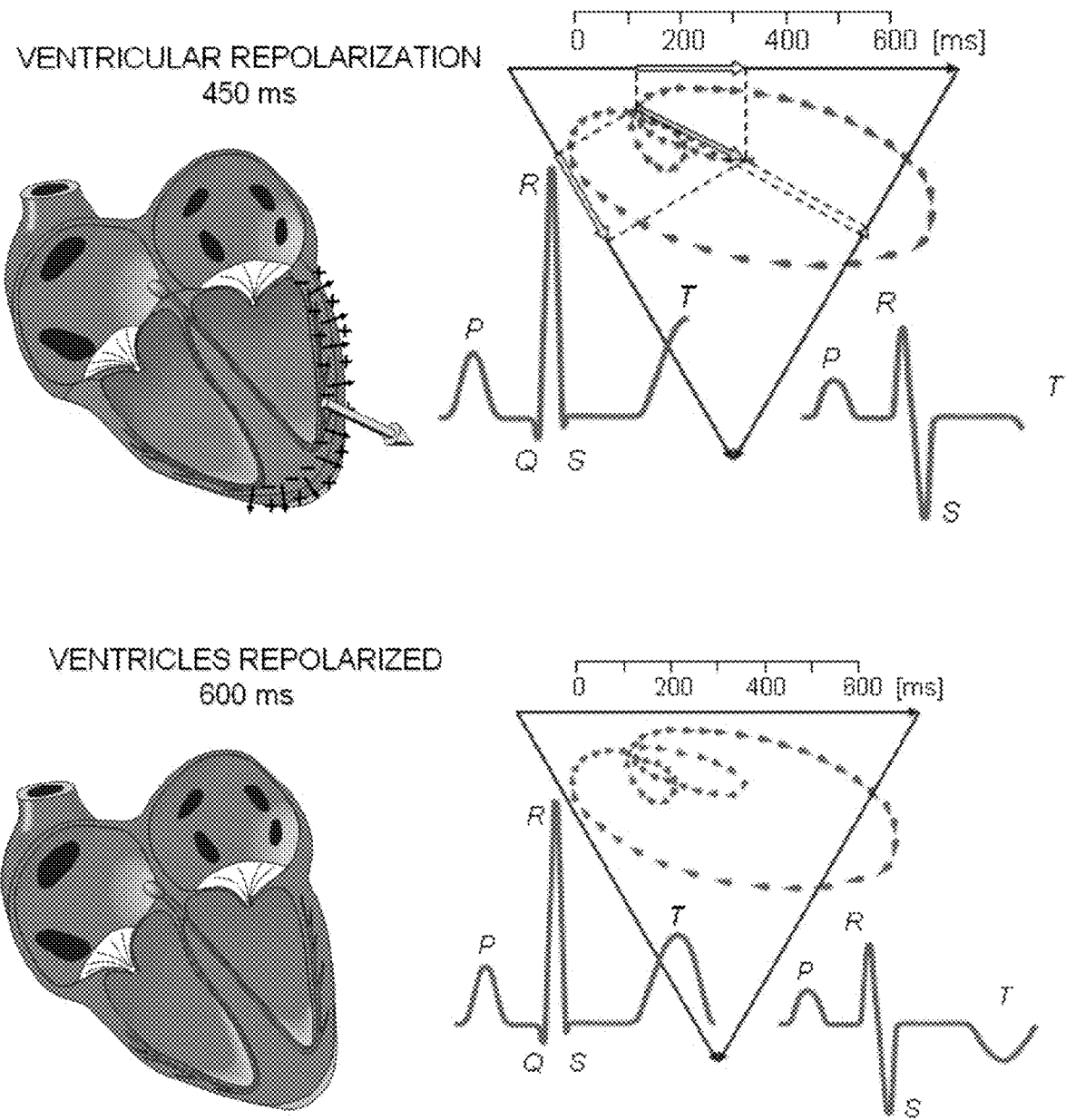
Figures 2A, 2B:
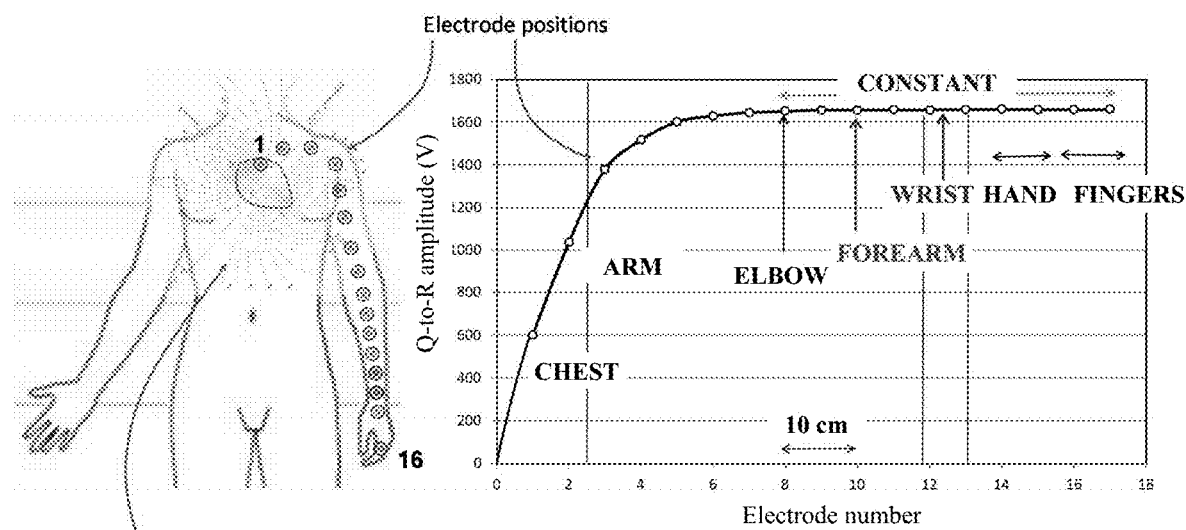
FIG. 2a schematically shows ECG recording on the 17 marked body points relative to initial (reference) point close to the patient's heart according to the prior art.
FIG. 2b shows voltage values (Q-to-R peak amplitude) recorded at marked electrode positions from 1 to 15 (positions 16 and 17 are hand and fingertip) according to the prior art.
Figure 2C:
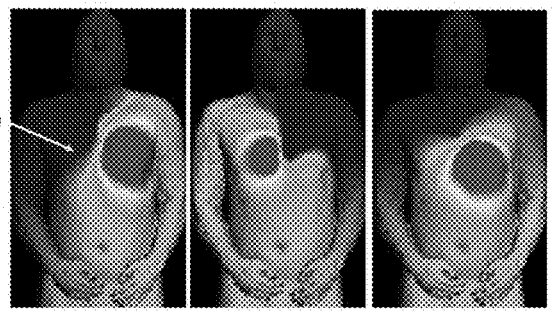
FIG. 2c shows three body surface potential maps during 50-ms QRS-interval (the potential is colour coded onto the body surface) according to the prior art.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

In one aspect of the disclosure, the present application describes a non-invasive method for continuous monitoring of at least one physiological parameter of a patient comprising:
1) Contacting a single sensing point on the patient's body with, or remotely positioning in a space against the patient's body, a microelectronic sensor comprising an open-gate pseudo-conductive high-electron mobility transistor (defined hereinafter as "transistor") or an array thereof;
2) Continuously recording electrical signals received from the patient's body in a form of a source-drain electric current of said transistor over time (defined as IDS dynamics) with said sensor;
3) Continuously transmitting the recorded signals from said sensor to an external memory; and
4) Processing the transmitted signals in the external memory, correlating said IDS dynamics with the physiological parameter and extracting the physiological parameter from said signals in a form of medical data, thereby continuously monitoring said physiological parameter;
wherein said transistor comprises:
  a) a multilayer hetero-junction structure made of III-V single-crystalline or polycrystalline semiconductor materials, said structure comprising at least one buffer layer and at least one barrier layer, said layers being stacked alternately, and said structure being deposited on a substrate layer or placed on free-standing membranes;
  b) a conducting channel comprising a two-dimensional electron gas (2DEG) or a two-dimensional hole gas (2DHG), formed at the interface between said buffer layer and said barrier layer and providing electron or hole current in said transistor between source and drain contacts;
  c) the source and drain contacts connected to said 2DEG or 2DHG conducting channel and to electrical metallizations for connecting said transistor to an electric circuit; and
  d) an open gate area between said source and drain contacts;
  wherein:
    (i) the thickness of a top layer (barrier or buffer) of said structure in said open gate area of said transistor is 5-9 nanometre (nm) which corresponds to the pseudo-conducting current range between normally-on and normally-off operation mode of the transistor, and
    (ii) the surface of said top layer has a roughness of about 0.2 nm or less.

In some embodiments, said external memory is a mobile device, desktop computer, server, remote storage, internet storage or telemedicine cloud. In other embodiments, said medical data is further displayed in form of a visual, graphical or mathematical representation of the IDS dynamics or any other readable format.

In a particular aspect, the physiological parameters monitored with the sensor of the embodiments are cardiac output and primary heart activity associated with an electrocardiogram, central venous pressure, left and right atrium pressures, heart rate variability, S2 split phenomenon associated with a phonocardiogram, lung or pulmonary activity associated with a breath cycle and dynamics, and with respiratory rate and volume, and brain activity associated with an electroencephalogram. In a specific embodiment, the physiological parameters are stroke volume, breathing related changes of the stroke volume, peripheral vascular resistance, breathing rate and amplitude (or tidal volume) and arterial compliance.

The user interface to which the recorded signals from the microelectronic sensor are transmitted may be any stationary or mobile processor. In case of a wearable device, such as bracelet, contacting a single sensing point on the patient's body with the sensor of embodiments is done by fastening the wearable device to the wrist of the patient, followed by recording the IDS dynamics and thereby, measuring at least one physiological parameter, such as electrocardiogram or right atrium pressure, of the patient.

Figure 4A:
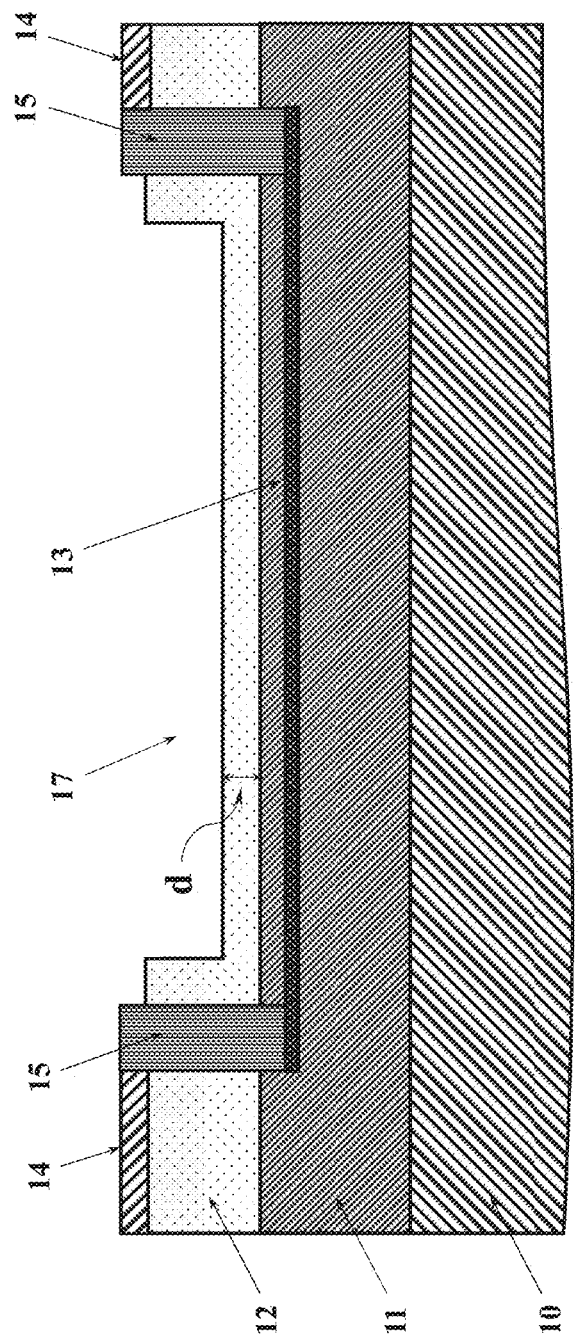
FIGS. 4a-4b schematically shows a cross-sectional view (XZ) (a) and a top view (XY) (b) of the PC-HEMT of an embodiment without a dielectric layer.
Figure 4B:
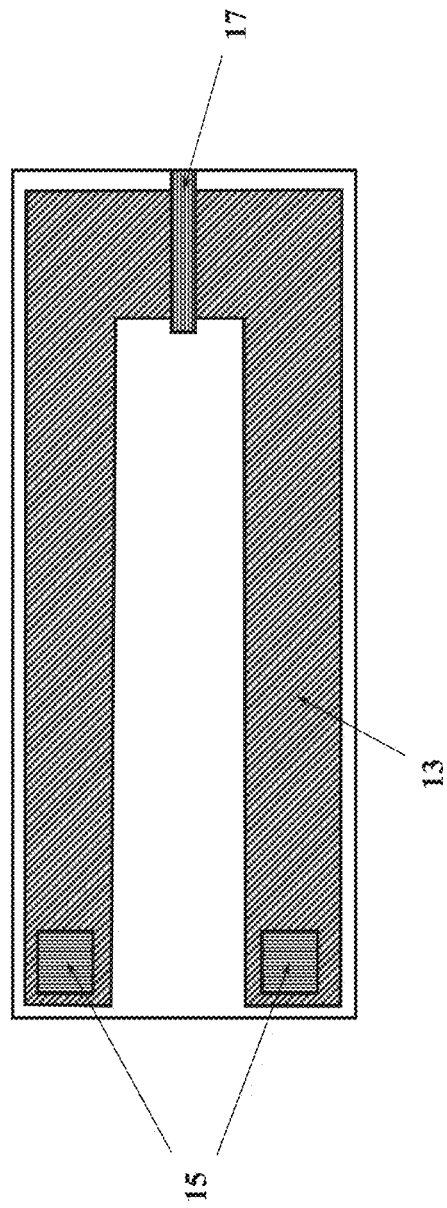

The source and drain contacts connecting the PC-HEMT to the electric circuit may be ohmic or non-ohmic (capacitively-coupled, as will be described below). In one embodiment, FIGS. 4a-4b shows a cross-sectional view (XZ) (a) and a top view (XY) (b) of the PC-HEMT of the present application comprising:

- a multilayer hetero-junction structure made of III-V single-crystalline or polycrystalline semiconductor materials, said structure comprising one buffer layer (11) and one top barrier layer (12), and being deposited on a substrate layer (10);
- a two-dimensional electron gas (2DEG) conducting channel (13) formed at the interface between said buffer layer (11) and said top barrier layer (12);
- source and drain ohmic contacts (15) connected to said 2DEG conducting channel (13) and to electrical metallizations (14) for connecting said transistor to an electric circuit; and
- an open gate area (17) between said source and drain ohmic contacts (15); wherein:
  (i) the thickness (d) of said barrier layer (12) in said open gate area (17) is 5-9 nm which corresponds to the pseudo-conducting current range between normally-on and normally-off operation mode of the transistor, and
  (ii) the surface of said top barrier layer (12) has a roughness of about 0.2 nm or less.

Further, FIG. 4c shows a cross-sectional view of the PC-HEMT of another embodiment comprising:

- a multilayer hetero-junction structure made of III-V single-crystalline or polycrystalline semiconductor materials, said structure comprising one buffer layer (11) and one top barrier layer (12), and being deposited on a substrate layer (10);
- a two-dimensional electron gas (2DEG) conducting channel (13) formed at the interface between said buffer layer (11) and said top barrier layer (12);
- electrical metallizations (14) capacitively-coupled to said 2DEG channel (13) for inducing displacement currents (25) thereby creating non-ohmic source and drain contacts connecting said transistor to an electric circuit; and
- an open gate area (17) between said source and drain non-ohmic contacts; wherein:
  (i) the thickness of the top barrier layer (12) in the open gate area (17) is 5-9 nm which corresponds to the pseudo-conducting current range between normally-on and normally-off operation mode of the transistor, and
  (ii) the surface of the top barrier layer (12) has a roughness of about 0.2 nm or less.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conductive channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semi-conductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

FIG. 4c illustrates the situation when an electrical connection of the transistor to the 2DEG channel is realised via capacitive coupling to the electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents. These displacement currents are induced by existing electrical fields between the electrical metallizations and the 2DEG conducting channel operated in the AC frequency mode through the Schottky contact as explained above.

Reference is now made to FIG. 4d that schematically shows a cross-sectional view of the PC-HEMT of an embodiment of the present application with highly-doped source and drain areas (18). In that case, the strong doping of the source and drain areas may result in a band-edge mismatch. However, if the semiconductor is doped strongly enough, it will form a certain potential barrier, low enough for conducting electrons to have a high probability of tunnelling through this barrier, and therefore conducting an electric current through the 2DEG channel.

An electrical connection to the 2DEG channel shown in FIG. 4d is realised with a highly doped semiconductor areas (18) overlapping the 2DEG channel and having a very low electrical resistance. Dopant ions such as boron ($B^+$), phosphorus ($P^+$) or arsenic ($As^+$) are generally created from a gas source, so that the purity of the source can be very high. When implanted in a semiconductor, each dopant atom creates a charge carrier in the semiconductor material after annealing. Holes are created for a p-type dopant, and electrons are created for an n-type dopant, modifying conductivity of the semiconductor in its vicinity. $As^+$ can be used for n-type doping, while $B^+$ and $P^+$ ions can be used for p-type doping. For example, in case of the AlGaN/GaN structure, the source and drain areas of the silicon structure are heavily doped with either $B^+$ or $P^+$ to create an electrical connection to the 2DEG channel. The silicon layers have a very low electrical junction resistance between each other in that case, and in order to induce an electrical current in the 2DEG channel, the metallizations are placed on top of the source and drain areas and connected to a circuit.

The third option would be the use of the photo effect that may also induce an electric current in the 2DEG channel. In order to couple the light excitation with the electronic effects in the conductive 2DEG channel, a photo effect in a silicon layer should be created. Regarding the direct photo effect, it is well known that light can only be absorbed when the energy of the absorbed photon ($E=h\nu$) is large enough for an electron to be excited into the valence band. In that case, E is the photon energy, h is Planck's constant and $\nu$ is the frequency of the photon. The frequency is coupled to the wavelength $\lambda$ of light by the constant speed of light $c=\lambda\nu$. Typically the bandgap of silicon at room temperature is 1.12.eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photo effect, it can be tuned by the size, crystalline direction and surface termination. These effects actually originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete these holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

If the source and drain contacts are non-ohmic (capacitively-coupled), in order to electrically contact the 2DEG channel underneath, which is about 7-20 nm bellow metallizations (14), the AC frequency regime is used. The capacitive coupling of the non-ohmic metal contacts with the 2DEG channel is normally induced at the frequency higher than 30 kHz. In the case of the non-ohmic contacts, the DC readout cannot be performed. Instead, the AC readout or impedance measurements of the electric current flowing through the 2DEG channel are carried out.

In some embodiments, the significant features of the PC-HEMT structure are that:
(i) the non-ohmic source and drain contacts for the capacitive coupling with the conductive 2DEG channel are used,
(ii) the thickness of the barrier layer in the open gate area is 5-9 nm, preferably 6-7 nm, more preferably 6.3 nm, corresponding to the pseudo-conducting current range between normally-on and normally-off operation mode of the transistor, and
(iii) the surface of the barrier layer has a roughness of 0.2 nm or less, preferably 0.1 nm or less, more preferably 0.05 nm.

Figure 4E:
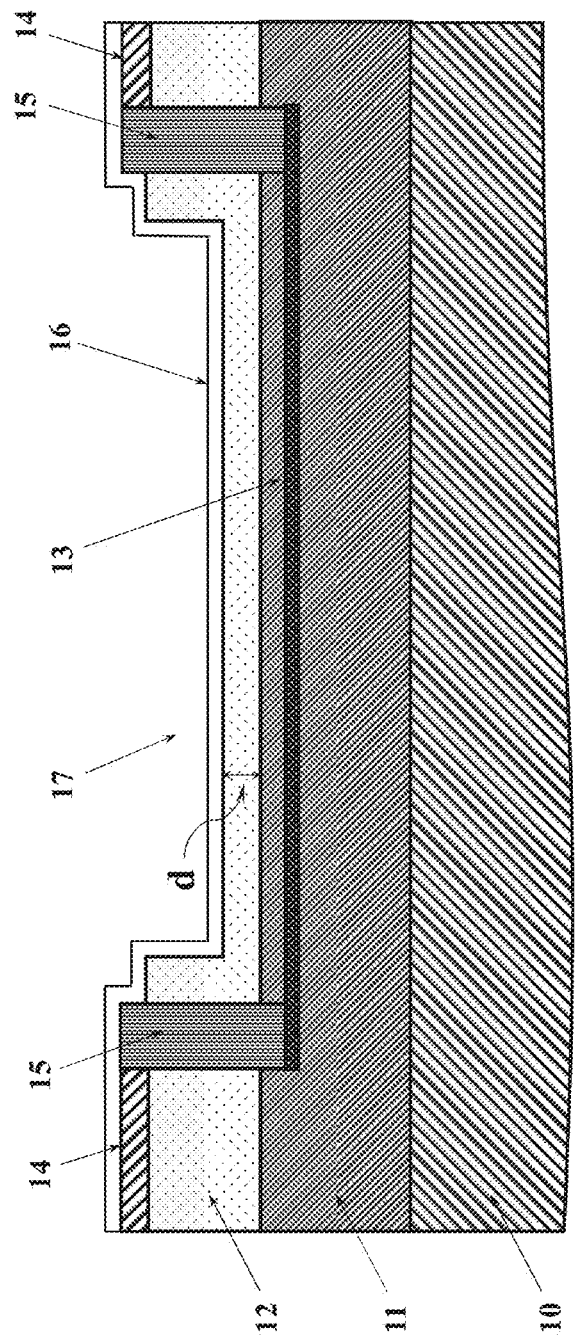
FIG. 4e schematically shows a cross-sectional view of the PC-HEMT of an embodiment with a dielectric layer.

The same transistors of the embodiments depicted in FIGS. 4a and 4c, but further comprising a dielectric layer (16), which is deposited on top of the barrier layer (12), are schematically shown in FIGS. 4e and 4f, respectively. In one embodiment, the optional dielectric layer (16), which is used for device passivation, is made, for example, of SiO—SiN—SiO ("ONO") stack of 100-100-100 nm thickness or SiN—SiO—SiN ("NON") stack having the same thicknesses. This dielectric layer (16) is deposited on top of the barrier layer by a method of plasma-enhanced chemical vapour deposition (PECVD), which is a stress-free deposition technique.

In a specific embodiment, the III-V semiconductor materials are selected from GaN/AlGaN, GaN/AlN, GaN/InN, GaN/InAlN, InN/InAlN, GaN/InAlGaN, GaAs/AlGaAs and $LaAlO_3/SrTiO_3$.

The electrical metallizations (14) connect the PC-HEMT to an electric circuit and allow electric current to flow between the source and drain contacts. The electrical metallizations (14) are made of metal stacks, such as Cr/Au, Ti/Au, Ti/W, Cr/Al and Ti/Al. The Cr or Ti layers of the metal stack is, for example, of 5-10 nm thickness, while the second metal layer, such as Au, W and Al, is of 100-400 nm thickness. The actual metallizations (14) are chosen according to the established technology and assembly line at a particular clean room fabrication facility. The source and drain ohmic contacts are usually made of metal stacks, such as Ti/Al/Mo/Au, Ti/Al/Ni/Au, Ti/Au and Ti/W having 15-50 nm thickness. The non-ohmic contacts on the other hand are capacitively coupled to the conducting 2DEG channel (13) via displacement currents (25).

In yet further embodiment, substrate layer (10) comprises a suitable material for forming the barrier layer and is composed, for example, of sapphire, silicon, silicon carbide, gallium nitride or aluminium nitride. The hetero-junction structure (11, 12) is deposited on the substrate layer (10), for example, by a method of metalorganic chemical vapour deposition (MOCVD), and forms a two-dimensional electron gas (2DEG) channel (13) in the close proximity to the interface between the buffer layer (11) and the barrier layer (12). The barrier layer (12) is then recessed between the source and drain contacts, thereby forming an open gate area.

The 2DEG channel (13) formed near the interface between the buffer layer (11) and the barrier layer (12) serves as a main sensitive element of the transistor reacting to a surface charge and potential. The 2DEG channel (13) is configured to interact with very small variations in surface or proximal charge or changes of electrical field on the barrier layer/liquid-air or barrier layer/metal/liquid-air interfaces interacting with the donor-like surface trap states of the barrier layer. This will be defined and discussed below in detail.

"Open gate area" of the PC-HEMT is defined as an area between the source and drain contacts of the transistor which is directly exposed to a conductive medium, such as liquid or gas capable of conducting current. An example of the conductive liquid is an electrolyte saline solution. In this case, instead of the fixed gate voltage, which is normally applied to a gate electrode, a reference potential is applied to the electrolyte-semiconductor system, via an optional reference electrode that is dipped into the electrolyte. As a result, in the absence of the physical gate, the electrolyte itself becomes an open gate of the transistor. This will be explained in more detail below.

The specific thickness of the barrier layer (12) in the open gate area is achieved by either dry etching the semiconductor material of the layer (12), i.e. recessing layer in the open gate area with the etching rate of 1 nm per 1-2 min in a controllable process, or coating the buffer layer (11) in the open gate area with an ultrathin layer of the III-V semiconductor material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after MOCVD growing.

Figure 5:
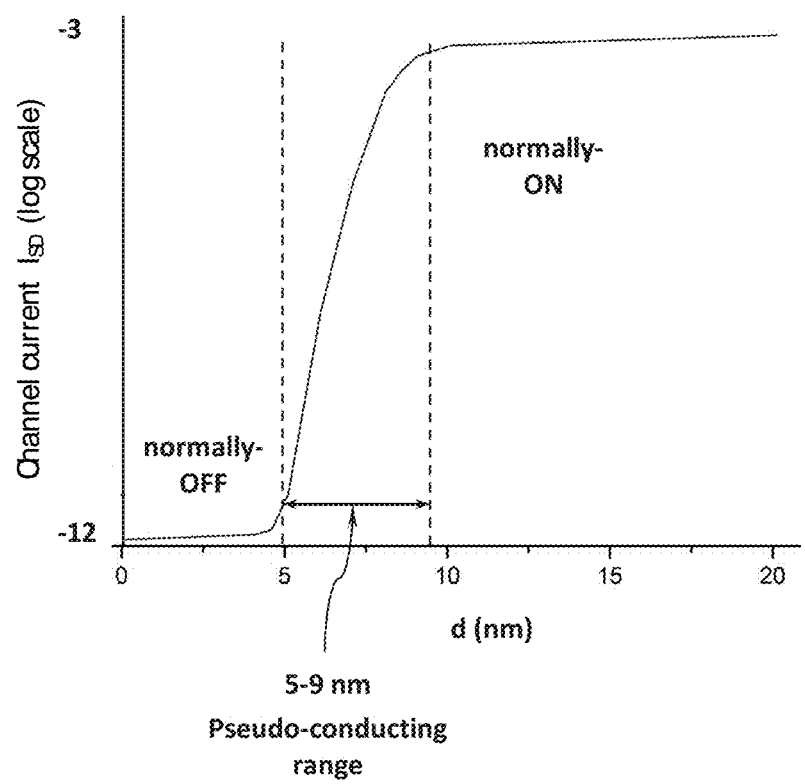
FIG. 5 schematically shows the dependence of the source-drain current (a charge carrier density) induced inside the 2DEG channel of a GaN/AlGaN HEMT on the thickness of the AlGaN barrier layer recessed in the open gate area.

FIG. 5 shows the dependence of the source-drain current (a charge carrier density) on the barrier layer thickness recessed in the open gate area. As seen from the plot, the HEMTs that have a thickness of the barrier layer in the open gate area larger than about 9 nm are normally-on devices. In such devices, due to the inherent polarisation effects present in the III-V materials, a thin sheet of charges is induced at the top and bottom of the interfaces of the barrier layer. As a result, a high electric field is induced in the barrier layer, and surface donor states at the top interface start donating electrons to form the 2DEG channel at the proximity of the hetero-junction interface without the application of a gate bias. These HEMTs are therefore normally-on devices. On the other hand, the HEMTs that have a thickness of the barrier layer in the open gate area lower than about 5 nm act as normally-off devices.

The barrier layer recessed in the open gate area to 5-9 nm is optimised for significantly enhancing sensitivity of the PC-HEMT sensor. This specific thickness of the barrier layer in the open gate area corresponds to the "pseudo-conducting" current range between normally-on and normally-off operation modes of the transistor and requires further explanation.

"Pseudo-contacting" current range of the HEMT is defined as an operation range of the HEMT between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps formed at the surface of the barrier layer of the HEMT are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state become pulled to the channel by the strong polarisation-induced electric field found in the barrier to form the 2DEG instantly. If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, crystal defects are created at the interface between the buffer layer and the barrier layer, and the piezoelectric polarisation instantly disappears causing deterioration in the 2DEG density.

Figure 6:
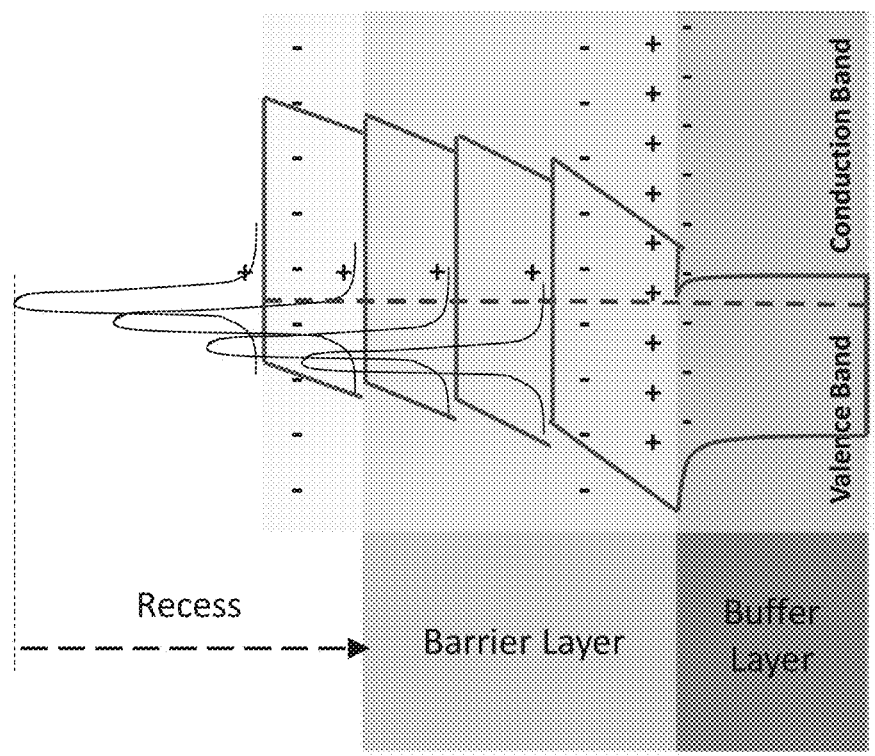
FIG. 6 illustrates a theory behind the 2DEG formation (charge neutrality combined with the lowest energy level) at the conduction band discontinuity.

In order to illustrate the above phenomenon of pseudo-conducting current, reference is now made to the following figures. As mentioned above, FIG. 5 shows the dependence of the source-drain current (a charge carrier density) on the recessed AlGaN barrier layer thickness. An energy equilibrium between the donor surface trap states and the AlGaN tunnel barrier leads to the 2DEG formation (charge neutrality combined with the lowest energy level) at the conduction band discontinuity. As explained above, decrease in the thickness of the barrier layer results in increase of the energy barrier. As a result, the ionisable donor-like surface trap states, which are responsible for electron tunnelling from the surface to 2DEG, drift bellow the Fermi level, thereby minimizing the electron supply to the 2DEG channel. This theoretical situation is illustrated in FIG. 6. Therefore, the recess of the AlGaN layer from 9 nm to 5 nm leads to extremely huge drop in the 2DEG conductivity for six orders of magnitude.

Thus, the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, such as surface reaction, charging etc., leads immediately to very strong 2DEG depletion. As a result, the surface of the barrier layer at this critical thickness is extremely sensitive to any smallest change in the electrical field of the surroundings.

Thus, recess of the gate area of the barrier layer from 9 nm down to 5 nm significantly reduces the 2DEG density, brings the transistor to the "near threshold" operation and results in highly increased surface charge sensitivity. The specific 5-9 nm thickness of the barrier layer responsible for the pseudo-conducting behaviour of the transistor gives the sensor an incredible sensitivity. So, when it comes into a contact with an ionic fluid or body skin, it opens up the gate to be able to do the ultrasensitive sensing.

In addition to the recessed barrier layer thickness, roughness of the barrier layer surface is another very important parameter that has not been previously disclosed. It has been surprisingly found that the roughness of the barrier layer surface (in the open gate sensitive area) bellow 0.2 nm prevents scattering of the donor-like surface trap states. Thus, the combination of these two features: 5-9 nm thickness of the barrier layer in the open gate area and strongly reduced roughness of its surface make the PC-HEMT an incredibly strong functional amplifier.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity

1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 7a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity

3) The N-face polarity is characterised by the 2DEG formation in the top GaN layer above the AlGaN barrier layer, as shown in FIG. 7b. In this case, the AlGaN barrier layer and two GaN buffer layers must be nominally undoped or n-type doped.
4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example with Mg or Be as an acceptor) and the bottom GaN layer should be also p-type doped with Mg, Be or intrinsic.

Thus, there are four hetero-junction three-layer structures implemented in the transistor of the embodiments, based on the above configurations:

A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area, with the roughness below 0.2 nm, and the thickness of the AlGaN barrier can be adjusted properly during growth.
B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).
C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth.

N-type doping levels of the GaN buffer layer and the AlGaN barrier layer must be adjusted; the 2DEG has to be contacted (in the ideal case by ohmic contacts).

D. N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 8:
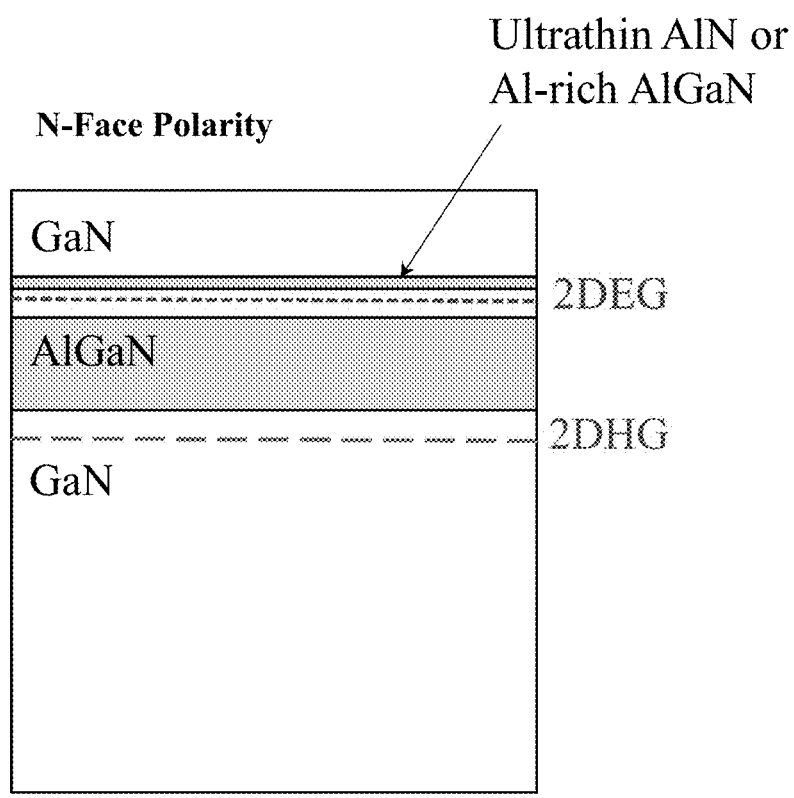
FIG. 8 schematically shows the formation of the 2DEG conducting channel in the N-face three-layer GaN/AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 8, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

Figure 9:
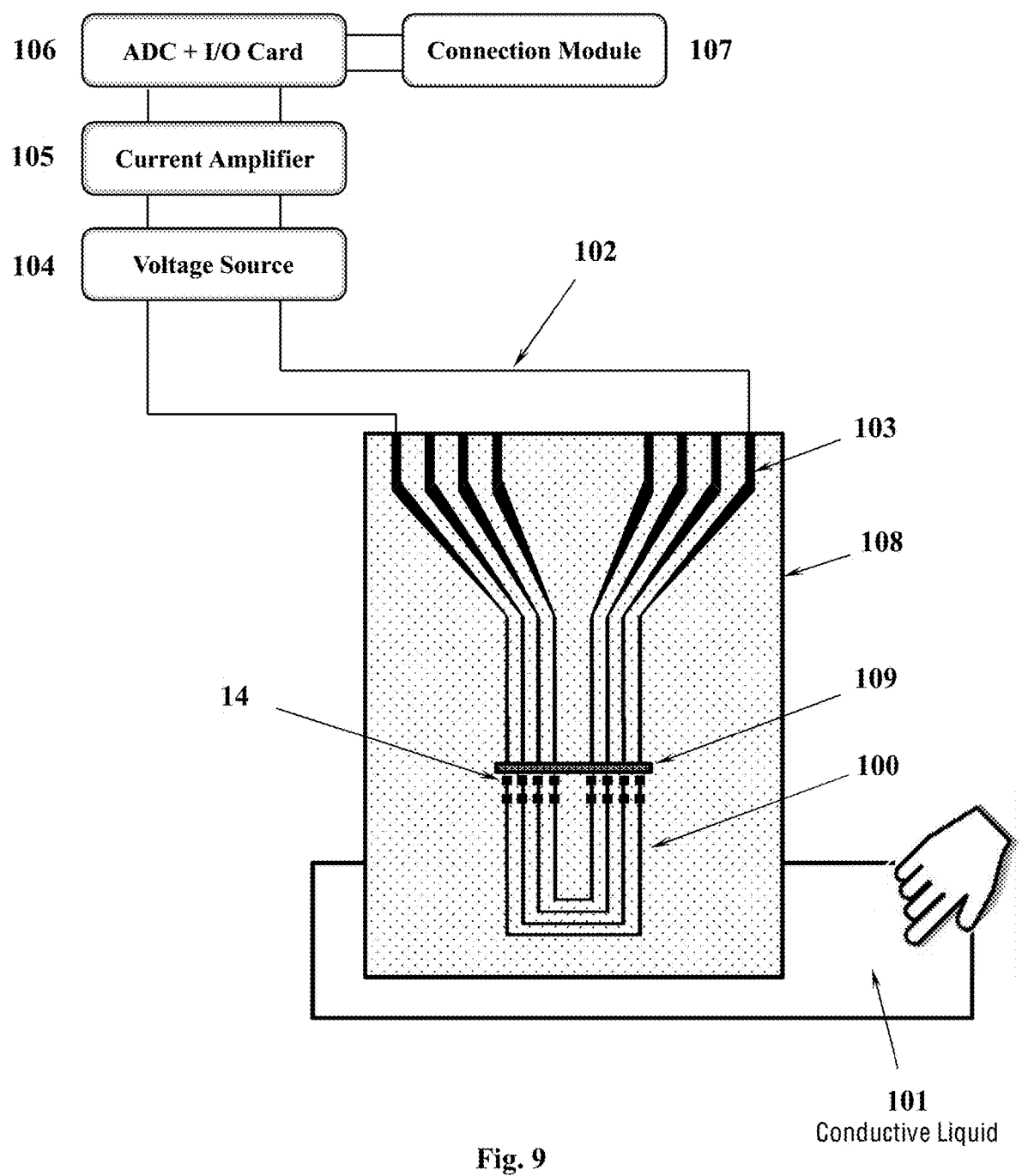
FIG. 9 represents a direct-contact microelectronic sensor of an embodiment.

In another aspect of the present disclosure, FIG. 9 illustrates a microelectronic sensor comprising the following components:

the PC-HEMT of an embodiment, or an array thereof (100), printed on a flexible printed circuit board (PCB) (108), wherein each one of said transistors is connected via electrical metallizations (14) to its dedicated electrical contact line (103) printed on said PCB (108);

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface; and a connection module (107) for connecting the sensor to the user interface.

All the above components of the sensor can be external or built in the transistor. As an example, the sensor layout shown on FIG. 9 has an array of four PC-HEMTs for more flexible test procedure. Each PC-HEMT of this sensor is fabricated on the substrate comprising 6-inch silicon wafers, the GaN buffer layer and the ultrathin AlGaN barrier layer, as described above. The AlGaN/GaN hetero-junction parameters used in this particular transistor were optimised for the ultrathin AlGaN barrier layer as follows: 3.5 nm SiN cap on top of the barrier layer, 6 nm $Al_{0.25}Ga_{0.75}N$ and 2 μm GaN buffer layer deposited on the Si wafer substrate. All the measurements further exemplified with this sensor were carried out on the fabricated samples without any additional surface treatment after ion implantation based 2DEG patterning step.

For utilisation within the conductive liquid (101), the fabricated sensor is glued on the flexible fibro-plastic PCB (108), and its wire bond connectors are protected with epoxy-based glob-top (109). The voltage source (104) can be any suitable and commercially available battery of the Li-ion type or any energy harvester with AC-DC or DC-DC converters. The ADC card (106) is any suitable analogue-to-digital converter card that can be purchased, for example, from National Instruments® or LabJack®. The current amplifier (105) can be any commercially available femto-ampere amplifier, for example SRS® SR570, DLPVA-100-F-S, FEMTO® current amplifier DDPCA-300 or Texas Instruments® INA826EVM.

In a further aspect of the present application, the sensor can be applied to a single-sensing point on patient's limbs (arms, elbows, forearms, wrists, palms or fingers) or can be used remotely from a patient's body. In a particular embodiment, the sensor of the present application can be used for cardiovascular monitoring from any single point on a patient's body and specifically from the wrist. In a further embodiment, the sensor can be applied to detection of electrical field or changes in electrical field of a body skin as a result of heart dipole charge dynamics during a complete heart cycle from atrial depolarization to ventricular repolarization.

In yet further embodiment, the sensor of the present application is contactless and used for remote cardiovascular monitoring. The sensor may be placed in a conductive liquid or left in open air within 5.0 m distance from a patient or less. In principle, any gas such as air, a liquid, such as saline solution, water or sweat, or a gel may be provided between the sensor and the body skin surface to detect the cardiac signals. The interaction between the body skin surface and the formed 2DEG channel occurs electrostatically via electric field in a manner similar to an interaction between a gate electrode and the 2DEG channel, by causing ionisation or energy shift of the donor-like surface trap states of the barrier layer. As shown in FIG. 9, a patient put his finger in the conductive liquid (101), for example sodium chloride solution. In that case, contact of the sensor with the conductive liquid (101) can physically represent the contact between the sensor and a skin surface. This situation is used in some embodiments of the present application in order to enable the cardiovascular monitoring remotely from the sensor. The conductive liquid (101) can be utilised in this case as a very stable intermediator for contact with the skin creating a gate as explained below.

Figure 10A:
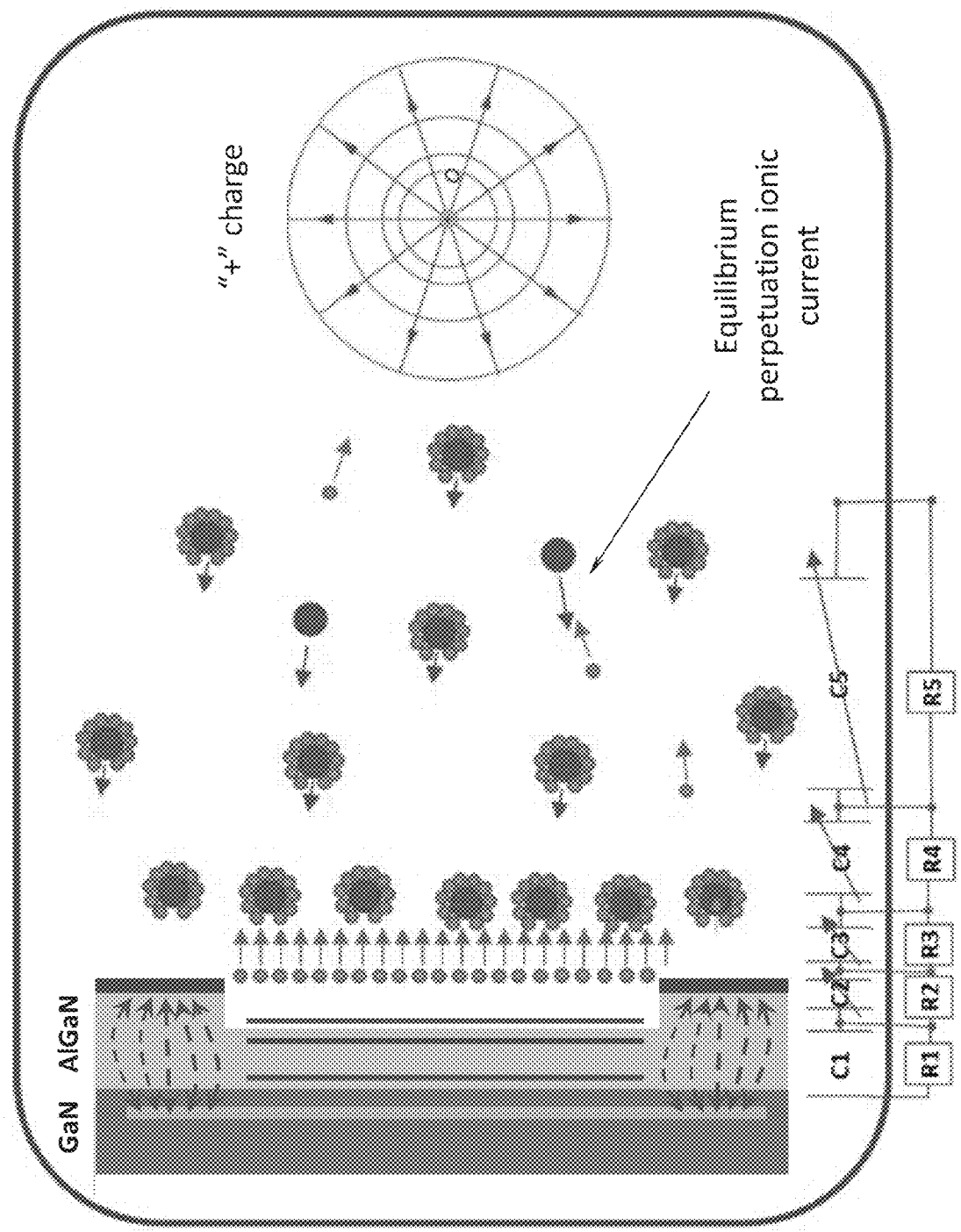
FIG. 10a schematically shows the barrier layer/liquid interface with the double layer formation, simplified equivalent interface circuity and ion electrodynamics during exposure of the sensor to a positive charge.
Figure 10B:
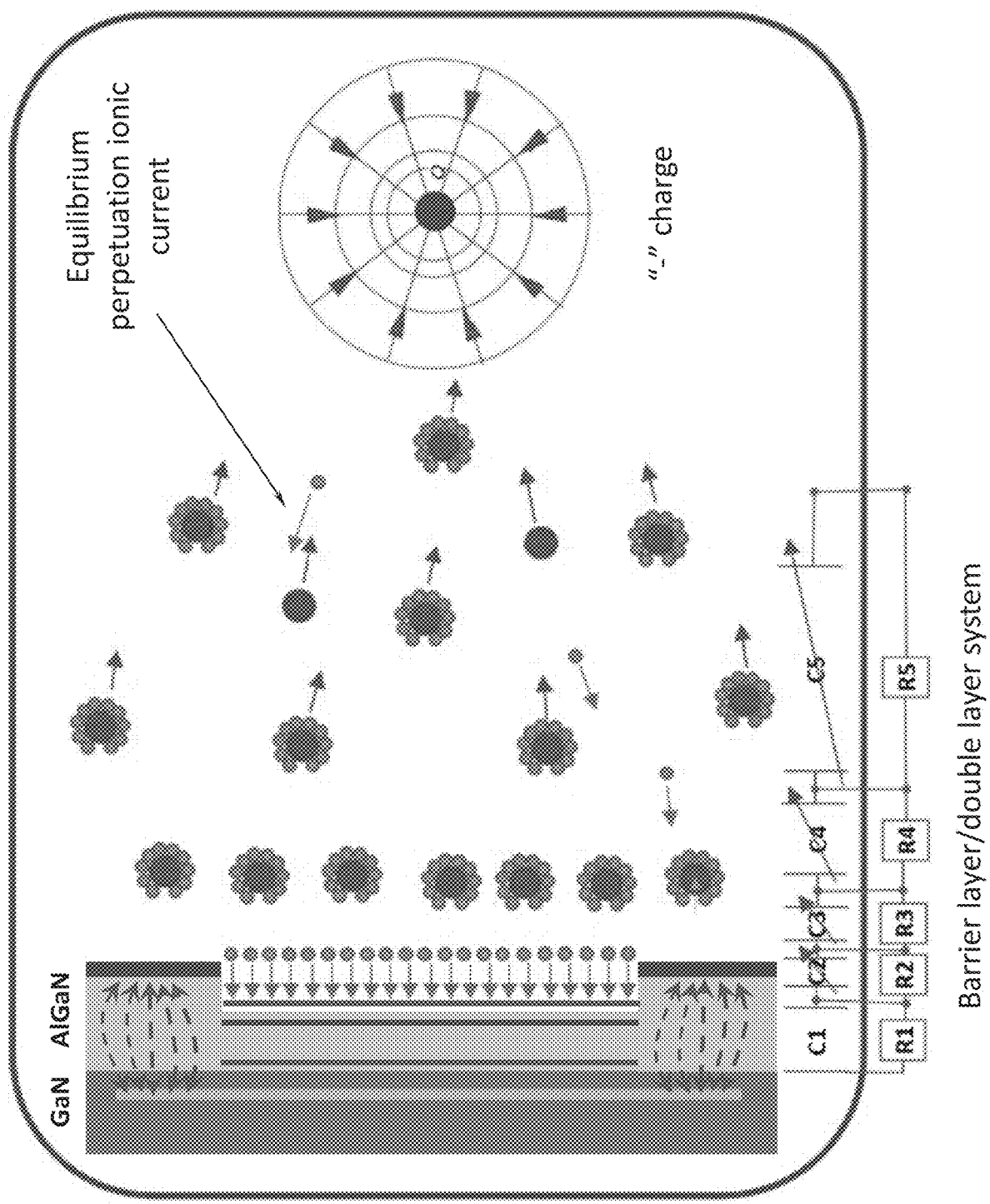
FIG. 10b schematically shows the barrier layer/liquid interface with the double layer formation, simplified equivalent interface circuity and ion electrodynamics during exposure of the sensor to a negative charge.

FIG. 10 schematically shows the barrier layer/liquid interface with the double layer formation, simplified equivalent interface circuity and ion electrodynamics during exposure of the sensor to (a) a positive charge and (b) a negative charge. Placed into a liquid, any surface potential causes the natural formation of an electrochemical double layer at the contact interface to maintain charge equilibrium between the solid state and ionic conductive liquid. In FIGS. 10a-10b, this double layer is shown schematically together with the simplified equivalent circuitry at the interface. The double layer is mostly created with a 1-3 nm thick sharp separation between the negative and positive ion space charge zones C2-R2 and C3-R3, which cause a secondary space charge equilibrium zone C4-R4 (10 nm-1 μm) and charge gradient zone C5-R5 disappearing in the bulk liquid. When there is no more potential shift from the solid and from the liquid, then the charge equilibrium is maintained with C1/R1-C5/R5 elements possessing a quasi-constant values.

Ion flow is schematically shown in FIGS. 10a-10b with vector arrows during an electrodynamic rearrangement when an external charge is introduced into an equilibrated electrolyte. FIG. 10a shows the electrodynamic rearrangement with an external positive charge, and FIG. 10b illustrates the electrodynamic rearrangement but with an external negative charge. When the ions react to an external electric field applied in the liquid, the equivalent circuitry mirroring the space charges changes accordingly. Since the sensor of some embodiments based on the PC-HEMT is extremely sensitive to any surface charge changes (C1/R1), the gradient ions rearrangement in the space charge zones from C5/R5 to a C2/R2 is able to modulate the 2DEG conductivity. The dynamic and magnitude of the new equilibrium is directly proportional to the liquid electrolyte conductivity, ions mobility and external charge value defining the resulted electrolyte charge. In general, any electrolyte strongly enhances the sensor charge response due to the excellent direct charge transfer towards the barrier layer/electrolyte interface. The ions of the liquid interact directly with the super sensitive surface trap states of the ultrathin barrier layer.

Thus, if the sensor is immersed into an ion conductive liquid, then the liquid ions will electro-dynamically react to any external charge by their movement. Being in direct contact to the barrier layer surface, the charge sensitivity is tremendously enhanced. The liquid functions in this case as an antenna perfectly matching to the 2DEG transducer. The heart generates electric charges, and a super position dipole of them is projected to a liquid antenna in which the sensor is immersed in. If the skin surface is in physical contact with the liquid, the detected signal is drastically increased, because the electric field within a body is transferred to the liquid with minimal loses. If the skin surface is outside of the liquid, then the sensed electric field created by the heart polarisation-depolarisation cycle is considerably weaker, but still can be detected by the sensor within 0.1-5.0 m distance from a patient or less, due to its extremely high sensitivity.

As discussed above, at any solid state/electrolyte interface, the capacitive and resistive elements of the sensor form an electrochemical surface potential originated from an interaction between the surface trap states and a double layer capacity, while the interaction between the 2DEG and the surface trap states originates from tunnelling and electrostatics. It has now been surprisingly found that operation of the PC-HEMT sensor as an open gate field-effect transistor is not required in order to modulate the surface electrochemical potential within the barrier layer/electrolyte system.

Figure 11:
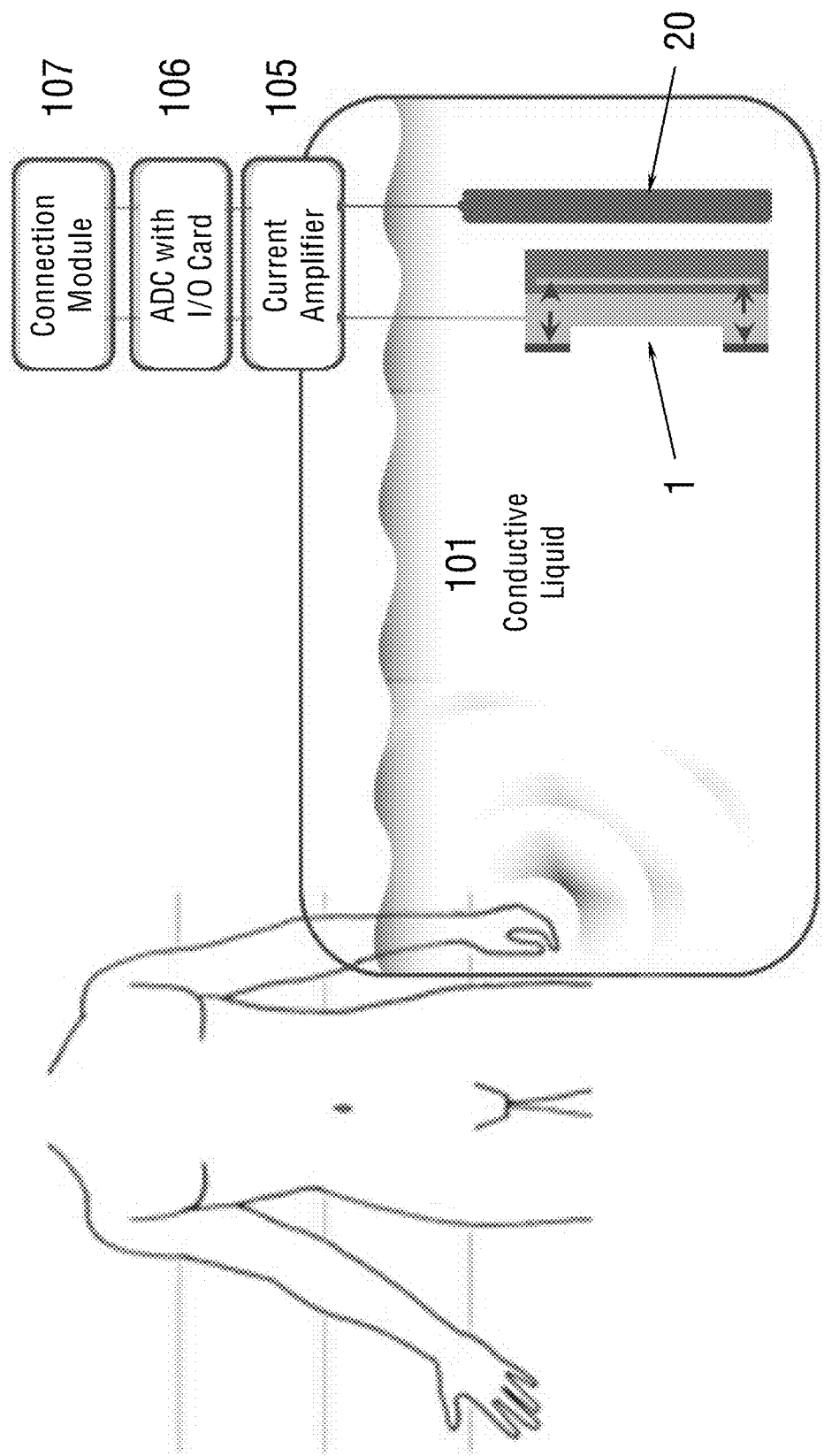
FIG. 11 schematically shows the system of an embodiment based on the PC-HEMT with an Ag/AgCl reference-cell electrode.

In a wired monitoring, the ECG electrodes can be attached to a patient's skin and further wired (bridges) with the electrolyte Au or Ag/AgCl gel electrodes. Small electrical resistance of the wires allows transporting the body (or skin) charges into the conductive liquid, where the PC-HEMT sensor is located. In another embodiment, the sensor of the present application additionally comprises a reference electrode for remote potentiometric body charge detection. FIG. 11 shows an embodiment of the system of the present application based on the PC-HEMT (1) with an Ag/AgCl reference-cell electrode (20), both dipped into conductive liquid (101) and connected to the readout circuit comprising the discussed above current amplifier (105), analogue-to-digital converter (106) and connection module (107).

Since the C1/R1 component is absent in the equivalent circuitry, there is no quantum mechanical interaction between the surface trap states and 2DEG in this system. Moreover, by definition, AgCl salt, which is non-polarising, cannot change its own potential at surface with ionic exchange processes. This is in contrary to AlGaN surface, which shows strong potential changes when an external charge is introduced in the liquid. While being exposed to the external charge, the response to changing potential at the barrier layer/liquid-interface within the PC-HEMT/liquid/AgCl system can be detected. The distance between the Ag/AgCl electrode and the PC-HEMT does not matter within a relatively compact vessel with the conductive liquid. Example 1 demonstrates the use of this potentiometric system and presents the bio-electrical data recorded with it.

Figure 12:
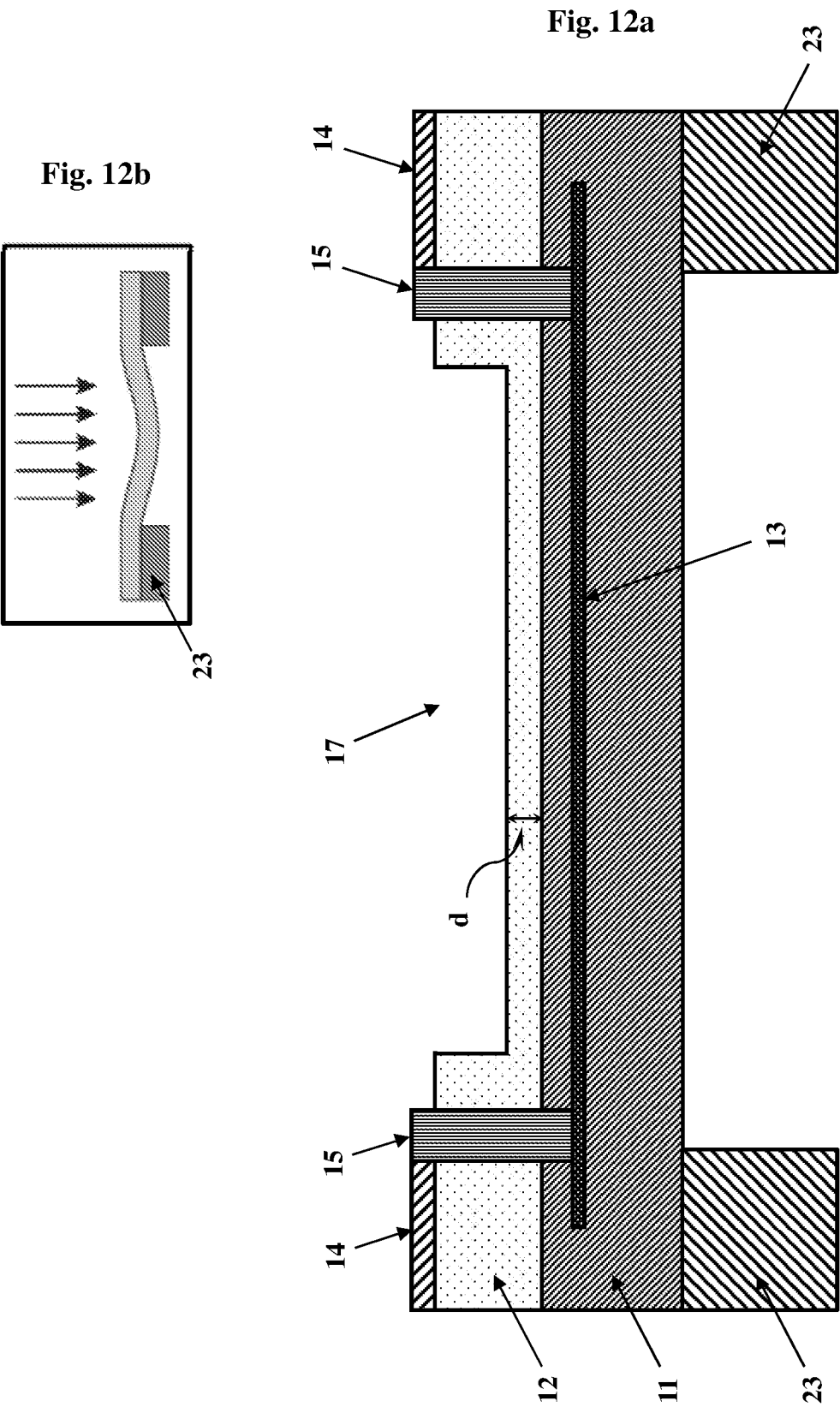
FIG. 12a schematically shows a cross-sectional view of the PC-HEMT of an embodiment with free-standing membranes.
FIG. 12b illustrates a situation when the external pressure (mass effect) is applied on the sensor incorporating the PC-HEMT of FIG. 12a, and transferred into a changed internal strain caused by bending.

FIG. 12a shows a cross-sectional view of the PC-HEMT configuration of an embodiment with free-standing membranes, comprising:

a multilayer hetero-junction structure made of III-V single-crystalline or polycrystalline semiconductor materials, said structure comprising at least one buffer layer (11) and at least one barrier layer (12), said layers being stacked alternately, and said structure being placed on free-standing membranes (23);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts;

the source and drain contacts (15) connected to said 2DEG or 2DHG conducting channel (13) and to electrical metallizations (14) for connecting said transistor to an electric circuit; and an open gate area (17) between said source and drain contacts (15);

wherein:

(i) the thickness of a top layer (barrier or buffer) (12) of said structure in said open gate area (17) is 5-9 nm which corresponds to the pseudo-conducting current range between normally-on and normally-off operation mode of the transistor, and (ii) the surface of said top layer (12) has a roughness of about 0.2 nm or less.

The PC-HEMT shown in FIG. 12a and placed on free standing membranes may be used in a "pressure-sensitive" sensors of an embodiment, which are capable of measuring very small pressures. These sensors use the free-standing membranes for creating a mass-loading effect which makes it possible to increase selectivity of the sensors via adding mechanical stress (mass-loading effect) as an additional parameter of the PC-HEMT-based sensor. The free-standing membranes (23) are very flexible free-standing columns of substrate composed of sapphire, silicon, silicon carbide, gallium nitride or aluminium nitride, preferably gallium nitride, having thickness of 0.5-2 μm. The free-standing substrate membranes are very sensitive to any tensile, compressive or mechanical stress changes on the surface of the multilayer hetero-junction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride (GaN), allow two mechanisms for strain transduction: piezoelectric and piezoresistive. The direct piezoelectric effect is used for dynamical pressure sensing. For measurements of static pressure, such sensors are not suitable due to some leakage of electric charges under the constant conditions. For static operation, the piezoresistive transduction is more preferable.

Piezoresistive sensors using wide band gap materials have been previously employed using hexagonal silicon carbide bulk materials for high temperature operation. Piezoresistivity of GaN and AlGaN structures is comparable to silicon carbide. However, piezoresistivity can be further amplified by HEMT structure, as taught by Eickhoff et al (2001). For piezoresistive strain sensing at relatively lower pressures (or pressure differences), diaphragm or membranes should be used, where the external pressure is transferred into a changed internal strain caused by bending, as shown in FIG. 12b. The resulting change in polarization alters the 2DEG channel current which is measured.

Eickhoff et al (2001) conducted the first experiments on AlGaN/GaN hetero-structures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN hetero-structures confined with the 2DEG channel.

The sensor configuration schematically shown in FIGS. 12a and 12b involves piezoelectrically coupled, charge and mass sensitive, free-standing GaN membranes, which are prepared, for example, according to U.S. Pat. No. 8,313,968, and offer an elegant and effective solution to achieve both downscaling and an integrated all-electrical low-power sensing-actuation. As mentioned above, GaN exhibits both, piezo- and pyro-electrical properties, which can be functionally combined. Whereas the piezoelectricity enables realisation of an integrated coupling mechanism, the 2DEG additionally delivers a pronounced sensitivity to mechanical stress and charge, which allows the sensor to use the pyroelectric effects. The dynamic change in 2DEG conductivity is also caused by a change in piezoelectric polarisation.

Figure 13:
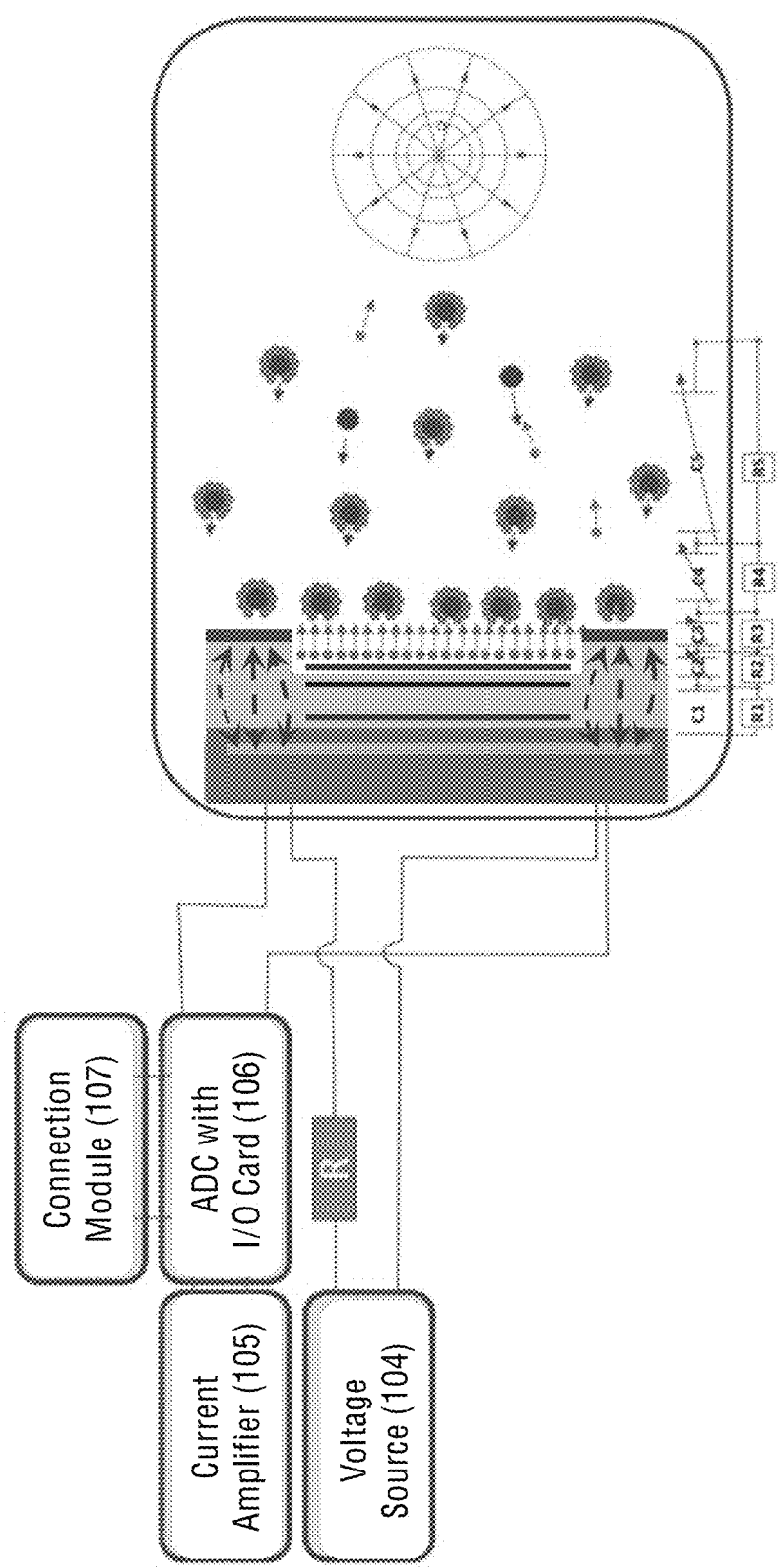
FIG. 13 schematically shows the system of an embodiment, wherein the voltage source is a battery.

In a specific embodiment, the sensor of the present application is powered by a battery. FIG. 13 shows an embodiment of the system of the present application, wherein the voltage source (104) is a battery, for example the AA-battery, which supplies electric current to the PC-HEMT. The setup also includes amplifier (105) with data logger card (106) and connection module (107), such as USB, NFC or Bluetooth. There are two options for setup operation including either differential voltage amplifier (105) connected in parallel, for example SRS® SR560, or a current amplifier (105) connected in-line, for example SRS® SR570. The SR560 setup allows the operation in high input impedance mode using the voltage divider resistance R. The relatively high SR560 input resistance of 100 MΩ is good for detection of very small charges without big leakages.

Another setup includes a current amplifier that operates directly with current flowing via the 2DEG channel of the PC-HEMT into the amplifier with small input resistance of 1MΩ at gain higher than $10^4$ and only 1Ω at gains lower than 200. Since the current amplifier in this case is switched off, the usage of voltage divider R is not necessary unless the voltage of 1.6V from the AA-element is too high. Thus, this setup directly amplifies the electric current modulation in the 2DEG channel originated from an external body charges. All readout components are battery powered to avoid ground loop parasitic current.

Figure 14:
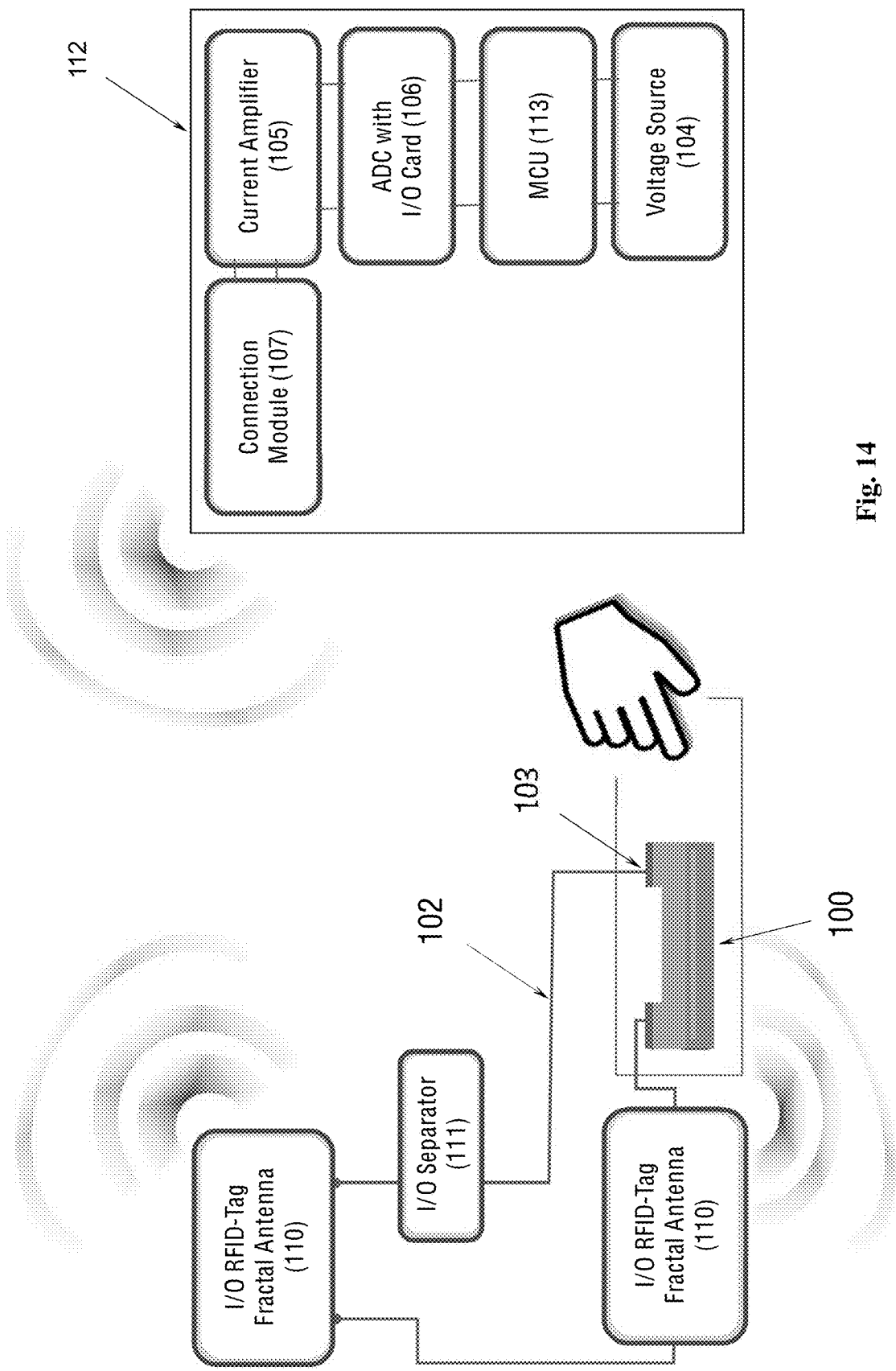
FIG. 14 schematically shows a zero-power RFID sensor of an embodiment with a remote readout.

For the cardiovascular measurements, there are two ways to establish the electrical (galvanic) contact with a patient's body. In a wireless monitoring, the finger can be immersed into an electrolyte solution with the PC-HEMT sensor. The test person and all set up components are electrically isolated to avoid ground loops. Reference is now made to FIG. 14 illustrating a zero-power radio-frequency identification (RFID) sensor of an embodiment of the present application for remote readout. In a particular embodiment, the RFID sensor comprises the following components:

the PC-HEMT of an embodiment, or an array thereof (100), wherein each one of said transistors is connected to its dedicated electrical contact line (103);

one or two out-input RFID-tag zero-power fractal antennas (110), each connected to said electrical contact lines (103) via an electric circuit (102) for receiving or transmitting a signal;

a diode input-output separator (111) to separate polarities in said circuit (102);

an integrated circuit (112) for storing and processing said signal, and for modulating and demodulating a radio-frequency (RF) signals, said circuit comprising:

a) a voltage source (104) supplying electric current to said transistors (100) and to said one or two antennas (110);

b) an integrated or CMOS current amplifier (105) for amplification of an electric current obtained from said transistors (100);

c) an analogue-to-digital converter (ADC) with wireless input/output modules (106) connected to said current amplifier (105) for wireless outputting the converted signal to a user interface;

d) a microcontroller unit (MCU) (113) for processing and converting the received signal into data readable in said user interface; and e) a wireless connection module (107) for wireless connection of said sensor to said user interface.

Figure 15:
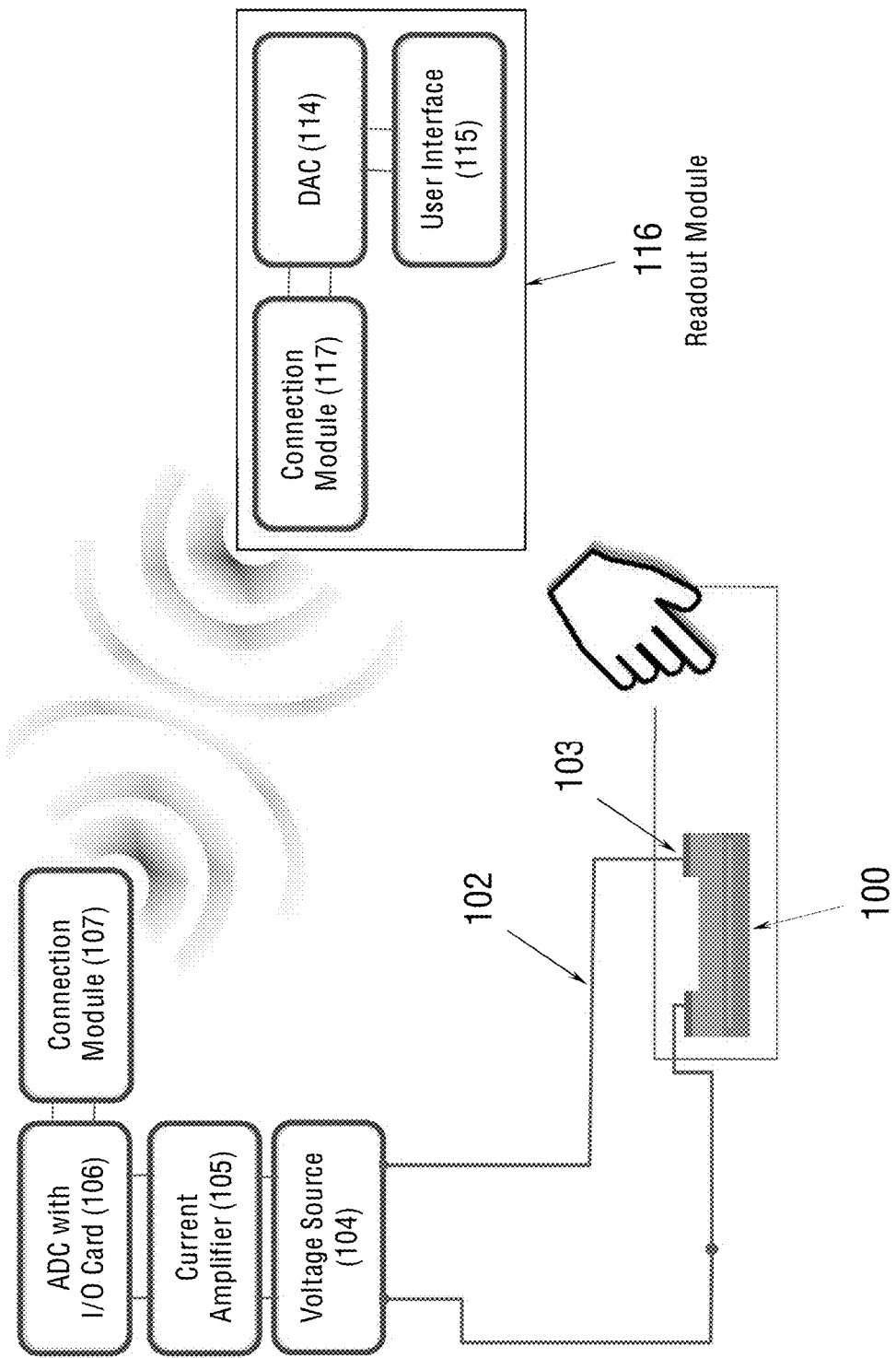
FIG. 15 schematically shows a direct-contact sensor of an embodiment with a remote readout.

The remote readout can be used with any sensor of the present application. In a specific embodiment, FIG. 15 schematically shows a microelectronic sensor of the present application comprising the following components:

the PC-HEMT of an embodiment, or an array thereof (100), wherein each one of said transistors is connected to its dedicated electrical contact line (103);

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface (115); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

In some embodiments, both wireless connection modules (107) and (117) are either Bluetooth or NFC, thereby providing wireless communication between the sensor and the readout module for up to 20 m. If these two modules are Wi-Fi, the connection between them can be established for up to 200 nm, while GSM allows the worldwide communication.

In yet further embodiment, the sensor of the present application additionally comprises a gate electrode for discharging parasitic electric current. The absence of any connection to a ground for a long time results in a parasitic readout in the system because of tribology effects, through the body friction, through the body charging and finally due to the parasitic charging of the PC-HEMT sensor itself.

Figure 16:
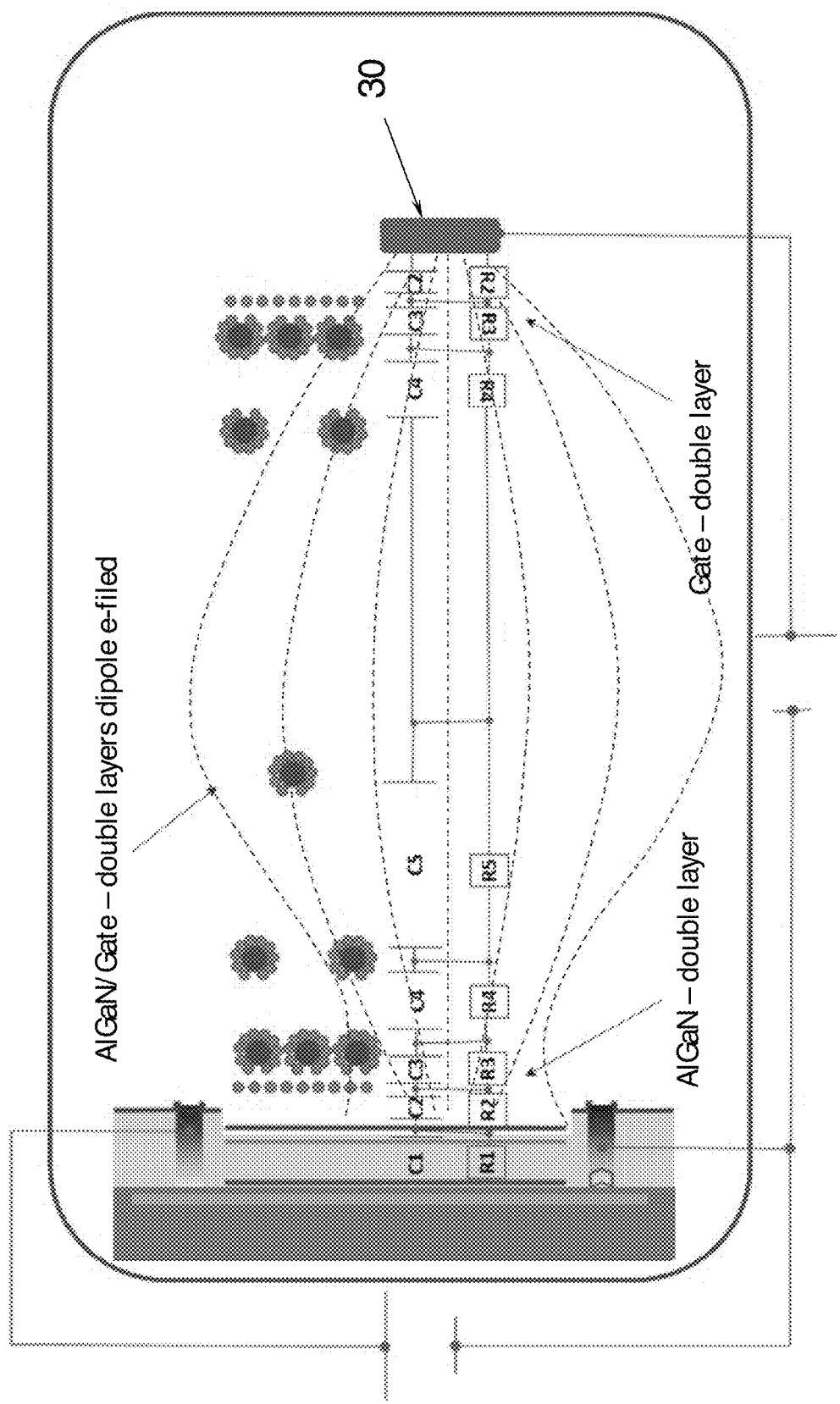
FIG. 16 illustrates the discharging method based on utilisation of the additional liquid gate electrode that is electrically connected to the power source of the sensor.

Since this parasitics has a low energy origin in the surface ionisation processes, it can be neutralised or discharged using an additional gate electrode. The discharging method is based on utilisation of the additional liquid gate electrode that is electrically connected to the power source of the sensor, as illustrated in FIG. 16. A potential difference to the gate electrode in the static liquid is formed, if no additional voltage source is connected to the system. As a result, an electrically coupled field is formed intrinsically affecting the surface charges from the sensor towards the gate electrode double layer. Due to creation of a direct potential difference with an electrical connection between the AlGaN layer surface and the gate electrode, there is much stronger influence on the C1/R1 components inside the AlGaN barrier layer. By applying an additional source-gate voltage through the battery powered signal generator or other power source, the parasitic charges can be de-trapped and neutralised at the AlGaN layer surface.

Figure 17:
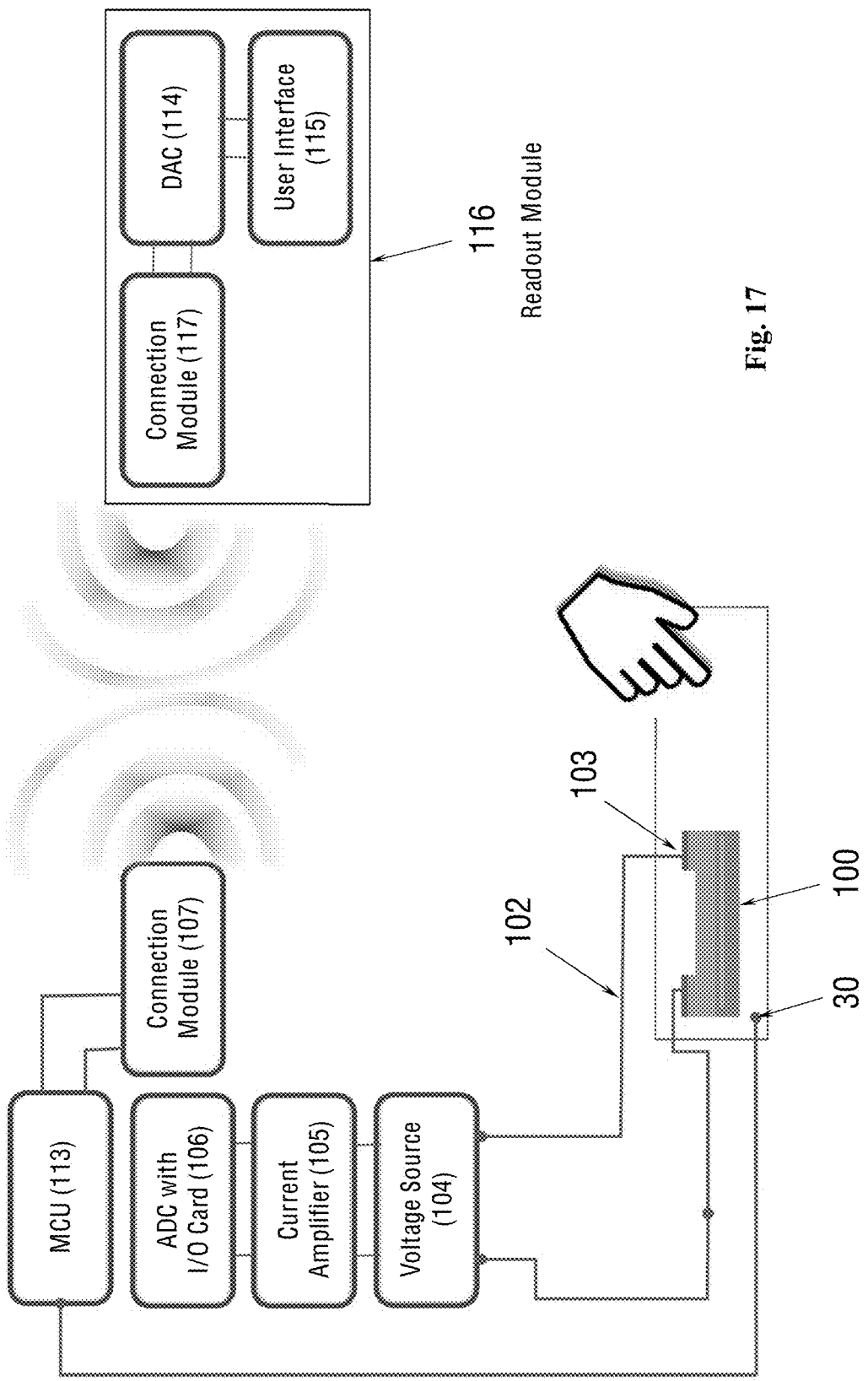
FIG. 17 schematically shows the direct-contact sensor of an embodiment with a remote readout and a feedback control for energy level adjustment and de-trapping via an external or integrated gate electrode.

In yet further embodiment, FIG. 17 schematically shows a microelectronic sensor with a feedback control for energy level adjustment and de-trapping via an external or integrated gate electrode, comprising the following components:

the PC-HEMT of an embodiment, or an array thereof (100), wherein each one of said transistors is connected to its dedicated electrical contact line (103);

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface (115);

a feedback control microcontroller unit (MCU) (113) for energy level adjustment and de-trapping via an external or integrated gate electrode (30); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

The gate electrode (30) is made, for example, of the following metal stacks: Cr/Au, Ti/Au, Cr/Al or Ti/W of 5-10/100-300 nm thicknesses, respectively.

Figure 18:
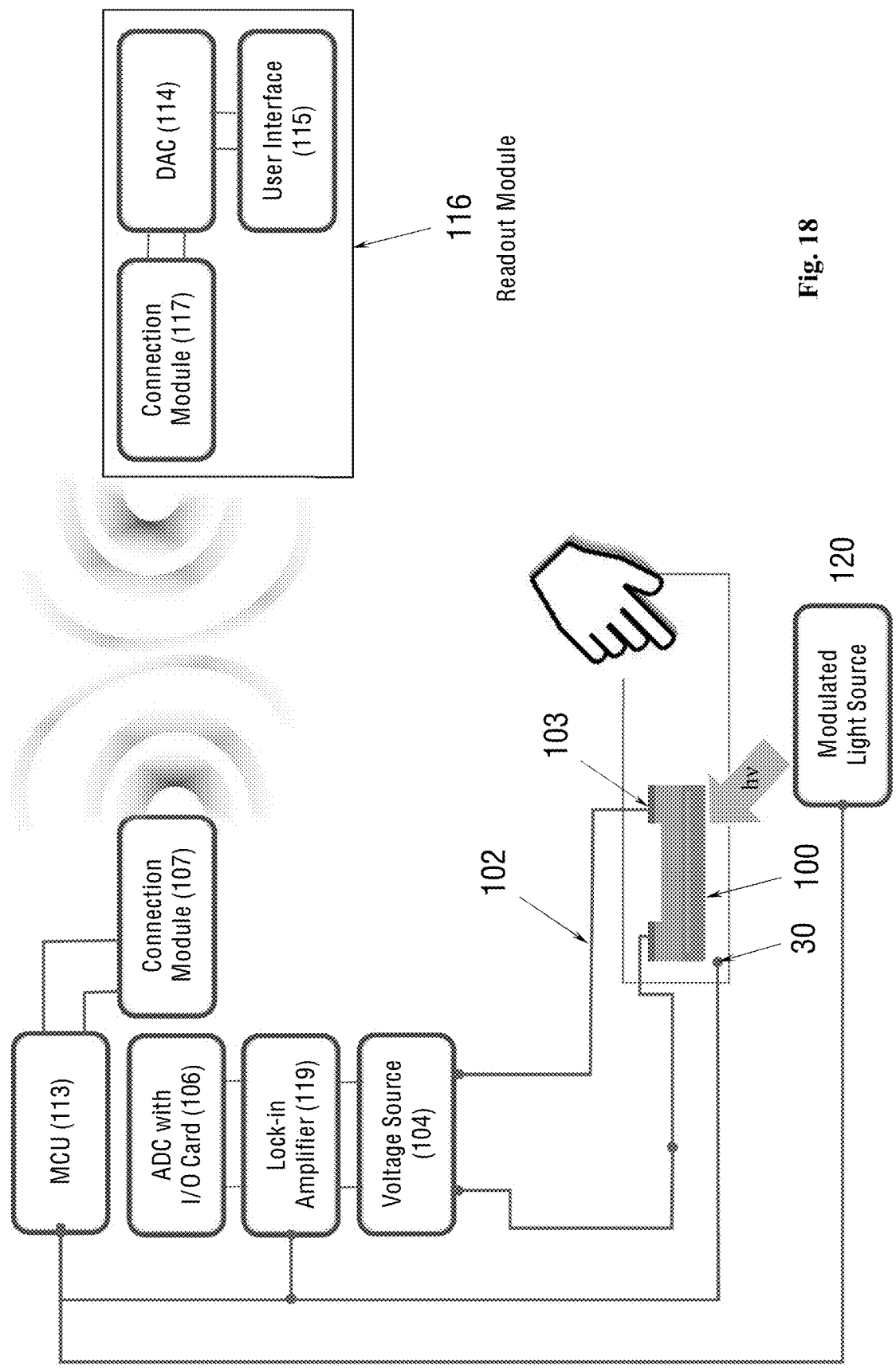
FIG. 18 schematically shows an optoelectronic sensor of an embodiment for remote readout.

In another embodiment, FIG. 18 schematically shows an optoelectronic sensor of the present application for remote readout comprises the following components:

the PC-HEMT of an embodiment, or an array thereof (100), wherein each one of said transistors is connected to its dedicated electrical contact line (103);

a modulated light source (120), such as a surface-mounted-device light-emitting diode (SMD LED) or UV-VIS-IR laser diode, for irradiating the barrier layer surface of said transistors;

a voltage source (104) connected to said electrical contact lines (103) via an electric circuit (102) for supplying electric current to said transistors;

a lock-in amplifier (119) connected to said voltage source (104) for amplification of a signal with a known carrier wave obtained from said transistors and increasing the signal-to-noise ratio;

an analogue-to-digital converter (ADC) with in-built digital input/output card (106) connected to said lock-in amplifier (119) for outputting the converted signal to a user interface (115);

a feedback control microcontroller unit (MCU) (113) for energy level adjustment and de-trapping via an external or integrated gate electrode (30); and a wireless connection module (107) for wireless connection of the sensor to a readout module (116); wherein said readout module (116) comprises another wireless connection module (117) connecting the sensor to said user interface (115) via a digital-to-analogue converter (DAC) (114).

As shown in the present application, some embodiments of the sensors of the present application can be used in the cardiovascular monitoring, i.e. detecting, measuring and monitoring the electrocardiography signals and central venous pressure (CVP). Some embodiments of the sensors of the present application are also capable of recording a phonocardiogram (PCG) and hence, considered as a replacement tool for regular stethoscopes. They are also capable of breath monitoring and lung activity diagnostics and hence, can be used in pulmonary and respiratory related applications. In another embodiment, these sensors can monitor the brain activity and measure and monitor electrical signals associated with an electroencephalogram (EEC). Further, some embodiments of the sensors of the present application can be used in eye pressure diagnostics.

In a particular embodiment, the sensors of the present application are applied to a single-sensing point on a patient's body, such as a patient's limb, for example arm, elbow, forearm, wrist, palm or finger. In another embodiment, the sensors of the present application are applied to an oral cavity of a patient. In a specific embodiment, the sensors of the present application are contactless and used remotely from a patient's body. In a particular embodiment, the sensor of the present application is used for detection of the primary heart activity signals as will be demonstrated in Example 1 below.

Figure 19:
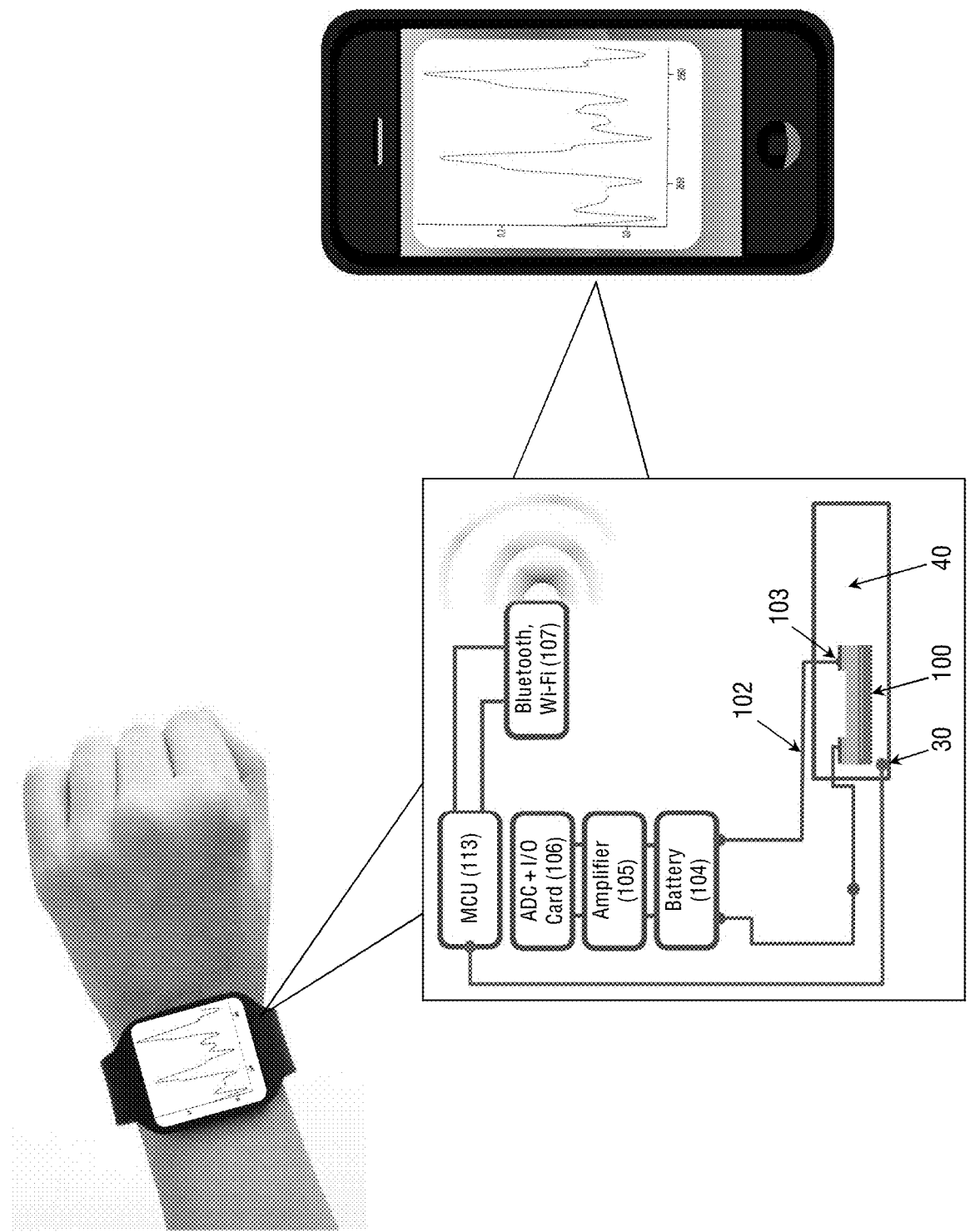
FIG. 19 shows a smart or fitness watch based on the PC-HEMT sensor of the present application according to some embodiments.

FIG. 19 shows a smart or fitness watch based on the PC-HEMT sensor of an embodiment of the present application. The in-built PC-HEMT sensor is capable of sensing the signals and transmitting them either to a phone or directly to a telemedicine cloud. Alternatively, some embodiments of the sensor of the present application can be integrated in a smartphone. The cardiovascular and pulmonary monitoring can be continuously carried out when the phone is in a contact with a hand or activated on calling or when a contact is established. The relevant medical data recorded is then transmitted to a medical-diagnostic telemedicine cloud and will be available for medical doctors.

In a certain aspect, a wearable device of the present application contains an integrated microelectronic sensor comprising the following components:

the PC-HEMT of an embodiment, or an array thereof (100), inserted in an electrolytic contact element (40), wherein each one of said transistors is connected to its dedicated electrical contact line (103);

a battery (104) connected to said electrical contact lines (103) via an electric circuit (102) for supplying electric current to said transistors;

an integrated or CMOS current amplifier (105) connected to said battery (104) for amplification of an electric current obtained from said transistors;

an analogue-to-digital converter (ADC) with in-built digital input/output card (106) connected to said current amplifier (105) for wirelessly outputting the converted signal to a smartphone or to a medical-diagnostic telemedicine cloud;

a microcontroller unit (MCU) (113) for energy level adjustment and de-trapping via an external or integrated gate electrode (30); and a wireless connection module (107) wirelessly connecting said wearable device to a smartphone or to a medical-diagnostic telemedicine cloud.

In a specific embodiment, the wireless connection module (107) can be a short-range Bluetooth or NFC providing wireless communication between the wearable device and a smartphone for up to 20 m. If this module is Wi-Fi, the connection can be established for up to 200 nm, while GSM allows the worldwide communication to a medical-diagnostic telemedicine cloud.

In some embodiments, the wearable device of and the system of the present application can be used for portable long-time-operation solution within a health, fitness and remote telemedicine cloud-based diagnostics. Since the device is used in a continuous cardiovascular and pulmonary monitoring, it should have a very small power consumption saving the battery life for a prolong usage. This is one of the major reasons to use the non-ohmic high-resistive contacts connecting the PC-HEMT sensor to an electric circuit, over the ohmic contacts. The non-ohmic contacts actually limit an electric current flowing through the 2DEG channel by having an electrical resistance 3-4 times higher than the resistance of the 2DEG-channel, thereby reducing electrical power consumption without sacrificing sensitivity and functionality of the sensor. Thus, the use of non-ohmic contacts in some embodiments of the PC-HEMT sensor of the present application is a hardware solution allowing to minimise the power consumption of the device. In another embodiment, the power consumption of the device can be minimised using a software algorithm managing the necessary recording time of the sensor and a battery saver mode, which limits the background data and switches the wireless connection only when it is needed.

EXAMPLES

Example 1

Electric Charge Origin of the Single-Point PC-HEMT Signal

There are different ways for detection of the primary heart activity signal in the beginning of pulse arrival (PAT) cycle within chest, which can be used for blood pressure calculation. The present inventors proved that, in some embodiments, the single-point PC-HEMT signal indeed originates from the heart dipole electric field variations and not from mechanical vibrations of the heart/body.

Figure 20A:
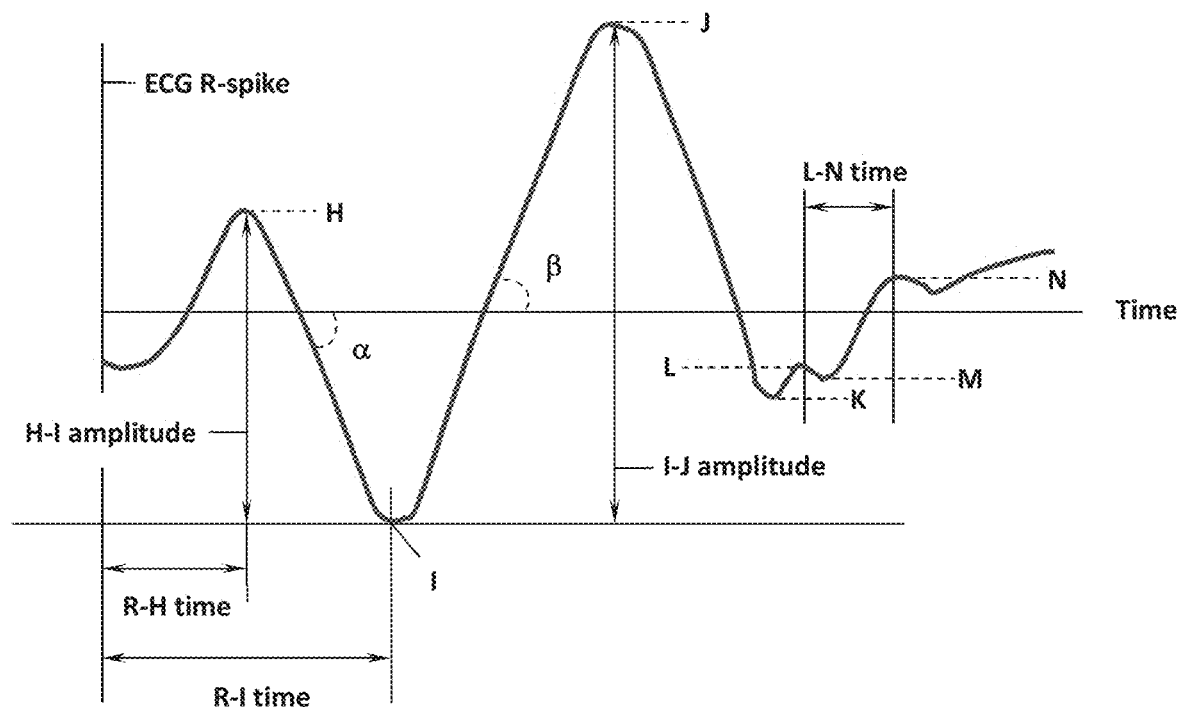
FIG. 20a shows a heart cycle expressed as characteristic ballistocardiography (BCG) peaks.
Figure 20B:
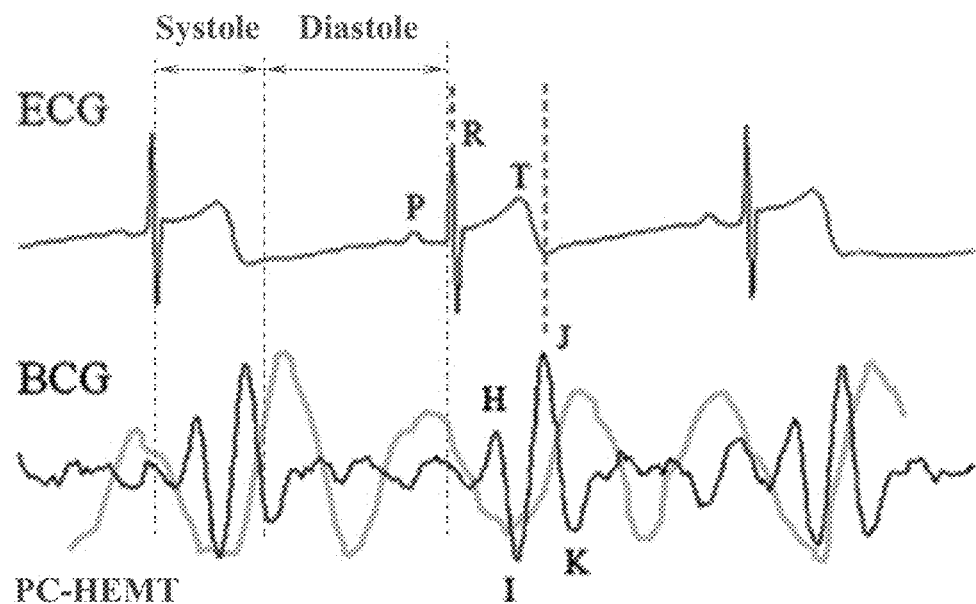
FIG. 20b shows simultaneously recorded ECG and BCG signals with the equivalently time-synchronised PC-HEMT sensor signal (in red).

In the applied biomedical research, the heart vibrations are measured by the technique known as ballistocardiography (BCG of the whole body movements) or seismocardiography (SCG mainly of the thorax movements). The mechanical BCG signal follows the electrical signal with a delay of about 30-40 ms. In the BCG, the mechanical motion of the heart is detected by measuring forces or acceleration from the chest. Alternatively, using the remote BCG recording, the blood pumping activity of the heart can be monitored. A single axis measurement in the length direction of the human body is normally adequate as this is the main direction of the blood flow. FIG. 20a shows a heart cycle expressed as characteristic ballistocardiography (BCG) peaks. FIG. 20b shows the simultaneously recorded ECG and BCG signals with the entirely (equivalently) time-synchronised PC-HEMT sensor signal (in red).

The wave amplitudes in FIG. 20a is a measure of the heart's beat volume, while the time of the peaks' appearance indicates the general functionality of the heart, the heart beat rate and its variability, the latter indicates the recovery state or stress of a person measured. The I and IJ amplitudes of the recorded signals in FIGS. 20a-20b can be useful in evaluating certain diseases such as aortic valve disease or coronary artery disease, and even in predicting life expectancy. When measuring the BCG signal with an accelerometer, the engineering challenges are the low level of signal acceleration relative to the noise from the sensor and the environment, as well as the frequency response and vibrations of a mechanical setup.

Figure 21:
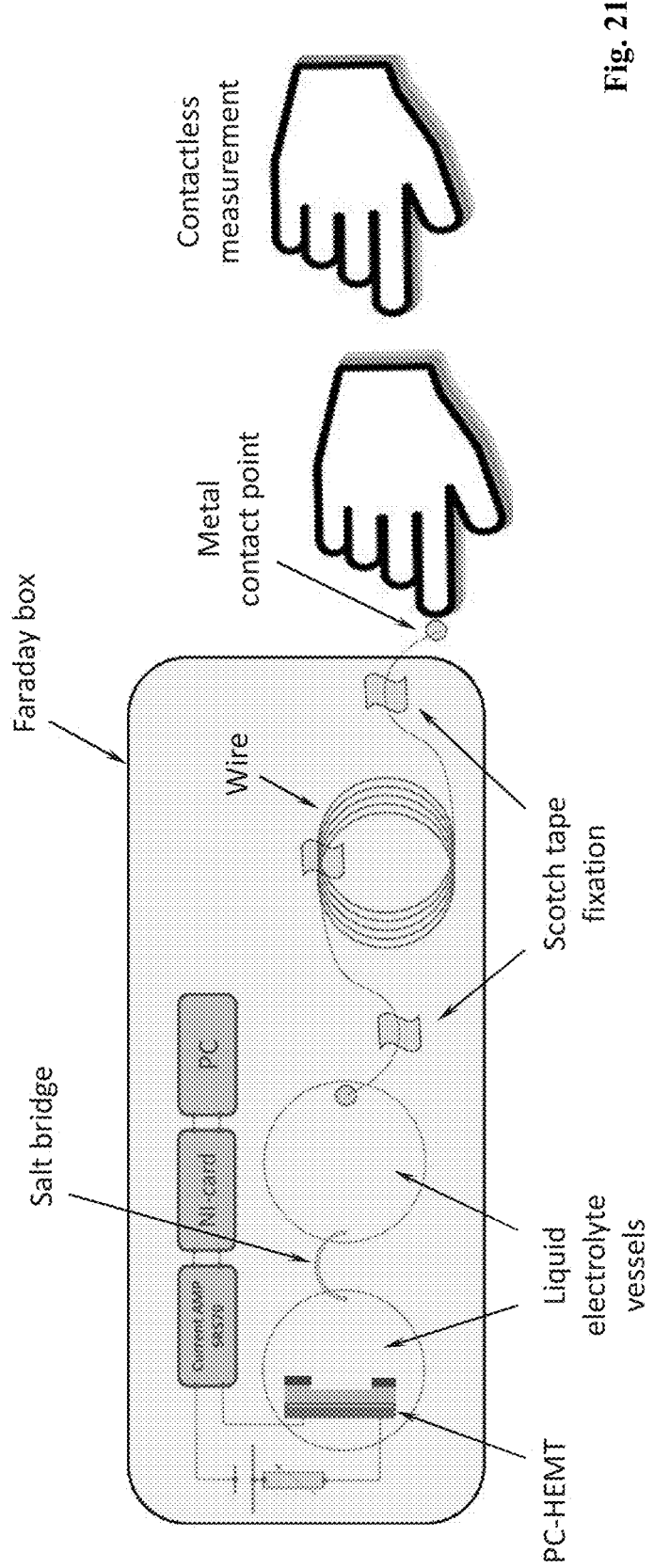
FIG. 21 schematically shows the experimental setup for minimisation of mechanical and vibrational heart movement artefacts.

FIG. 20b shows a comparison of the time-synchronised ECG, BCG and single-point PC-HEMT sensor measurements. The BCG-signal dynamics of the shown vibrational H-IJK-L-cycle in relation to the P-QRS-T-cycle of the ECG is completely different from the PC-HEMT sensor signal dynamics. The reason for such difference is that the signals obtained from the PC-HEMT originate from dipole charges created by the heart movement and not from its mechanical vibrations. This can be further proven with the PC-HEMT sensor setup shown in FIG. 21, which excludes any mechanical wave transfer. This particular sensor is used for minimising the mechanical and vibrational heart movement artefacts, where the PC-HEMT sensor is placed and shielded within a Faraday box. Inside this box, the sensor is placed in a small vessel containing electrolyte saline solution and connected via a salt bridge to another similar vessel with the electrolyte solution. One end of a coiled extension wire was placed in a liquid, while another end was used for contacting a fingertip outside the Faraday box.

The measurements carried without a Faraday box showed the same signal detection. Moreover, the same signal was also detected contactlessly. Thus, the single point monitoring using the PC-HEMT sensor shown in this setup can only be based on the cardiac signals originated from the dipole charges, simply because the transfer of the mechanical vibrations from heart to the sensor is not possible with this particular sensor.

Example 2

Cardiovascular and Pulmonary Monitoring with the PC-HEMT Sensor

Figure 22:
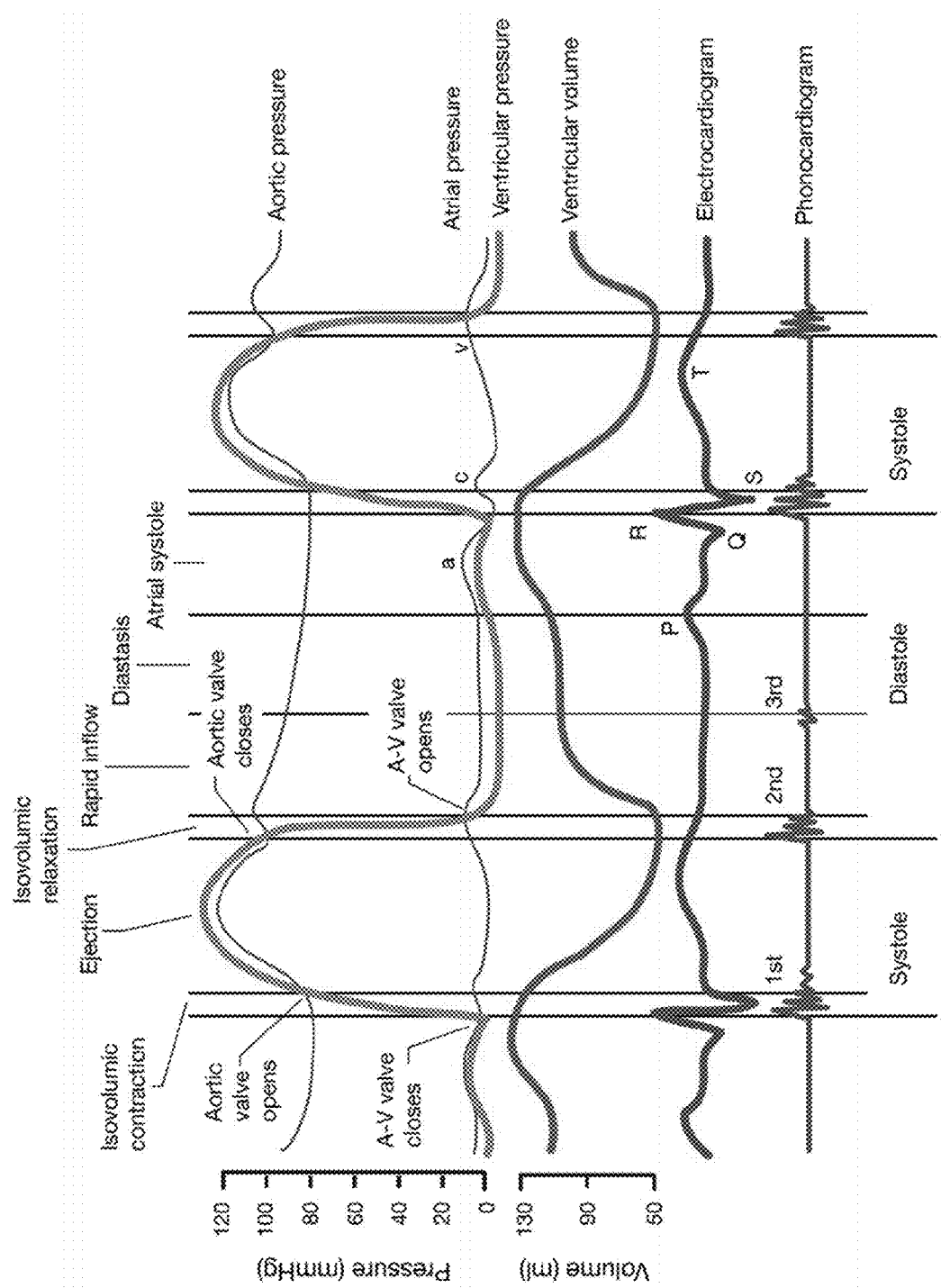
FIG. 22 shows the formal representation of the heart beat recorded with conventional instruments.
Figure 23:
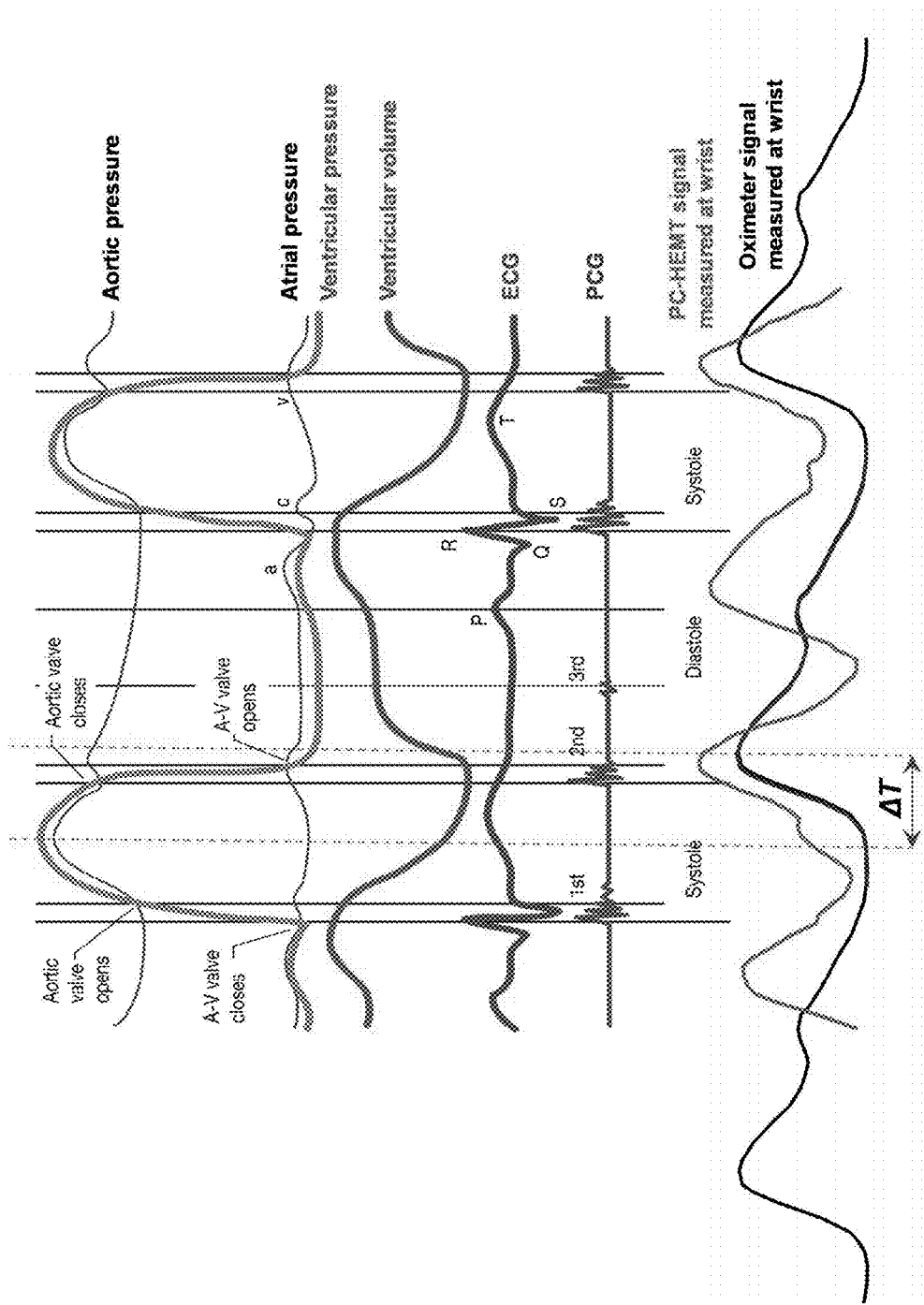
FIG. 23 shows the heart beat detected with the PC-HEMT sensor and with an oximeter at wrist compared to standard signals.
Figure 24A:
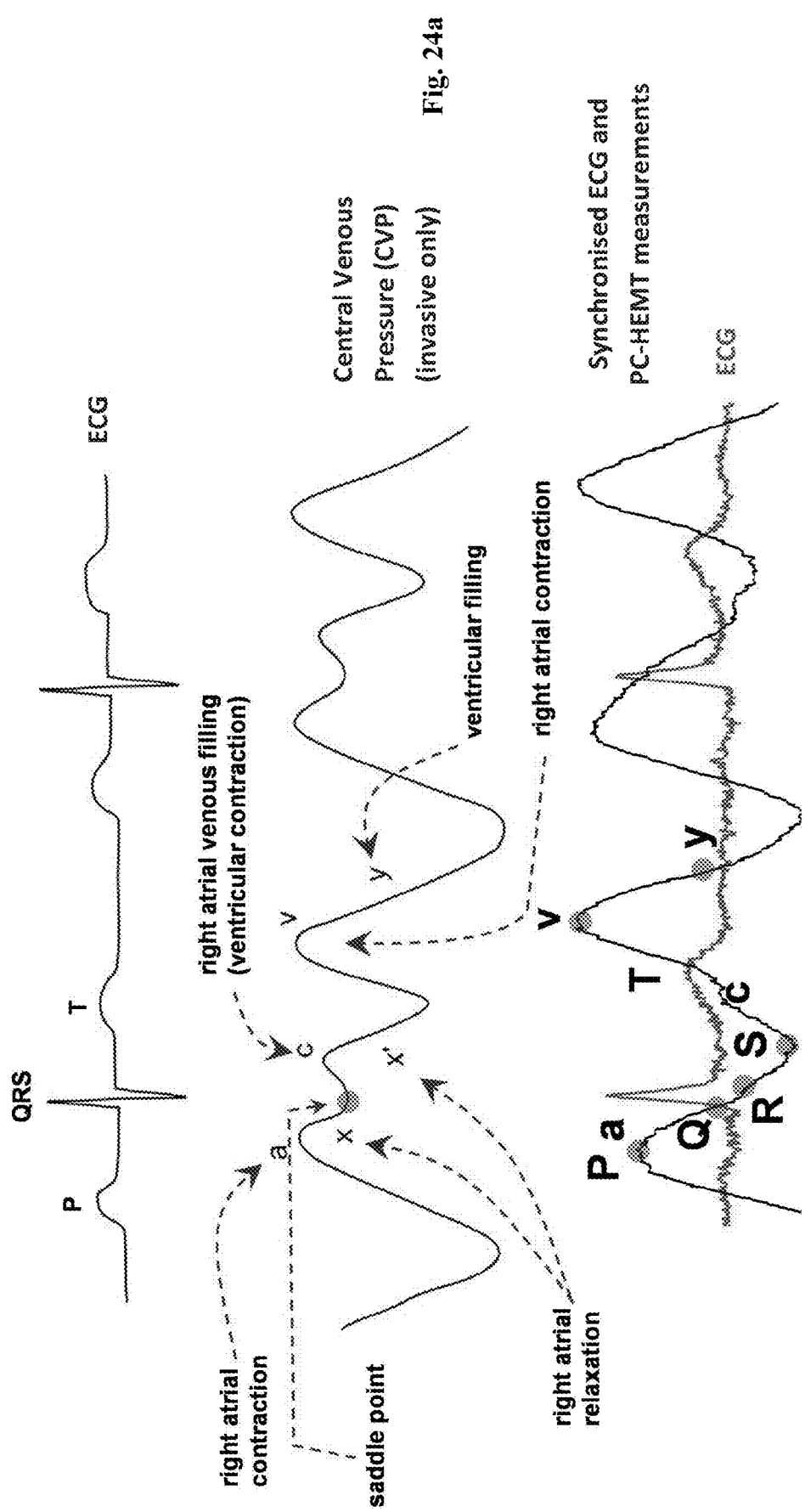
FIG. 24a shows the central venous pressure (CVP) waveform data synchronised with the cardiac signals data recorded with the ECG and with the PC-HEMT sensor.
Figure 24B:
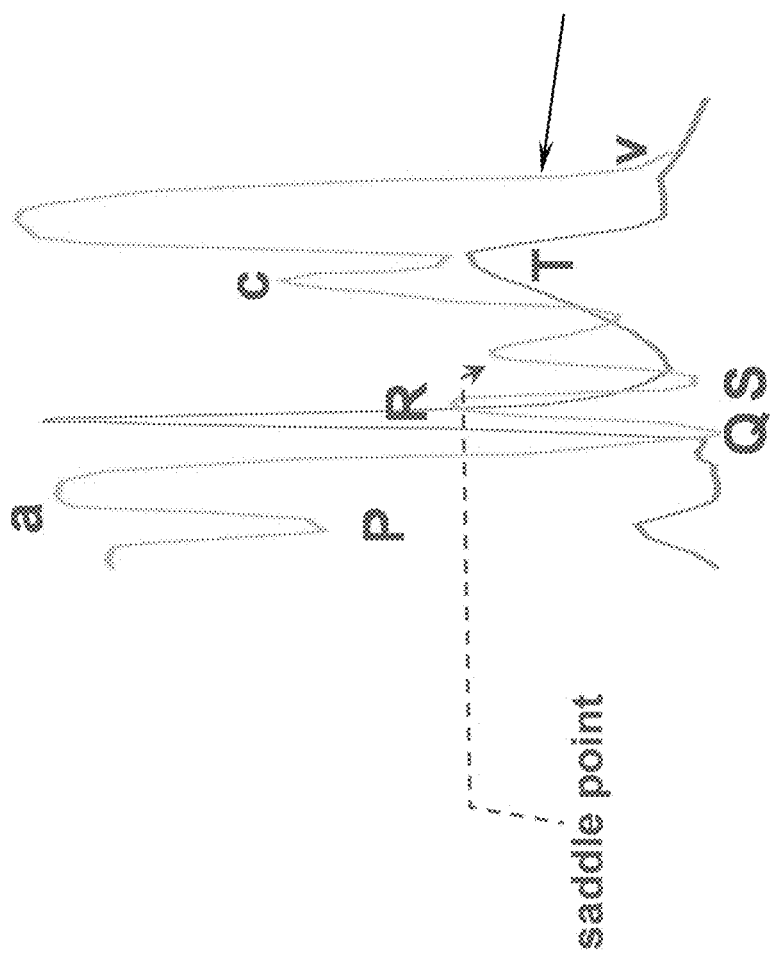
FIG. 24b shows the first derivative of the recorded ECG curve of FIG. 23a obtained with one hundred combined measurements using the PC-HEMT sensor.

Reference is now made to FIG. 22 showing the heart beat waveform recorded with different conventional instruments (Wiggers Diagram, cited from WikiCommons 2008). FIG. 23 shows the heart beat detected with the single-point PC-HEMT sensor and with a pulse oximeter at wrist compared to standard signals. The oximeter signal follows the aortic pressure waveform with a time delay $\Delta T$ which is typical to placement of the device. FIG. 24a shows the central venous pressure (CVP) data synchronised with the cardiac signals data recorded with the ECG and with the PC-HEMT sensor. FIG. 24b shows the first derivative of the recorded ECG curve obtained from 100 combined data measurements using the PC-HEMT sensor. It conforms to the CVP readings and enables the non-invasive CVP to be performed in conjunction with the above ECG using an embodiment of the sensor of the present application. Thus, the cardiac signals recorded with the PC-HEMT sensor non-invasively contain all the information relating to the heart activity and central venous pressure.

Figure 25:
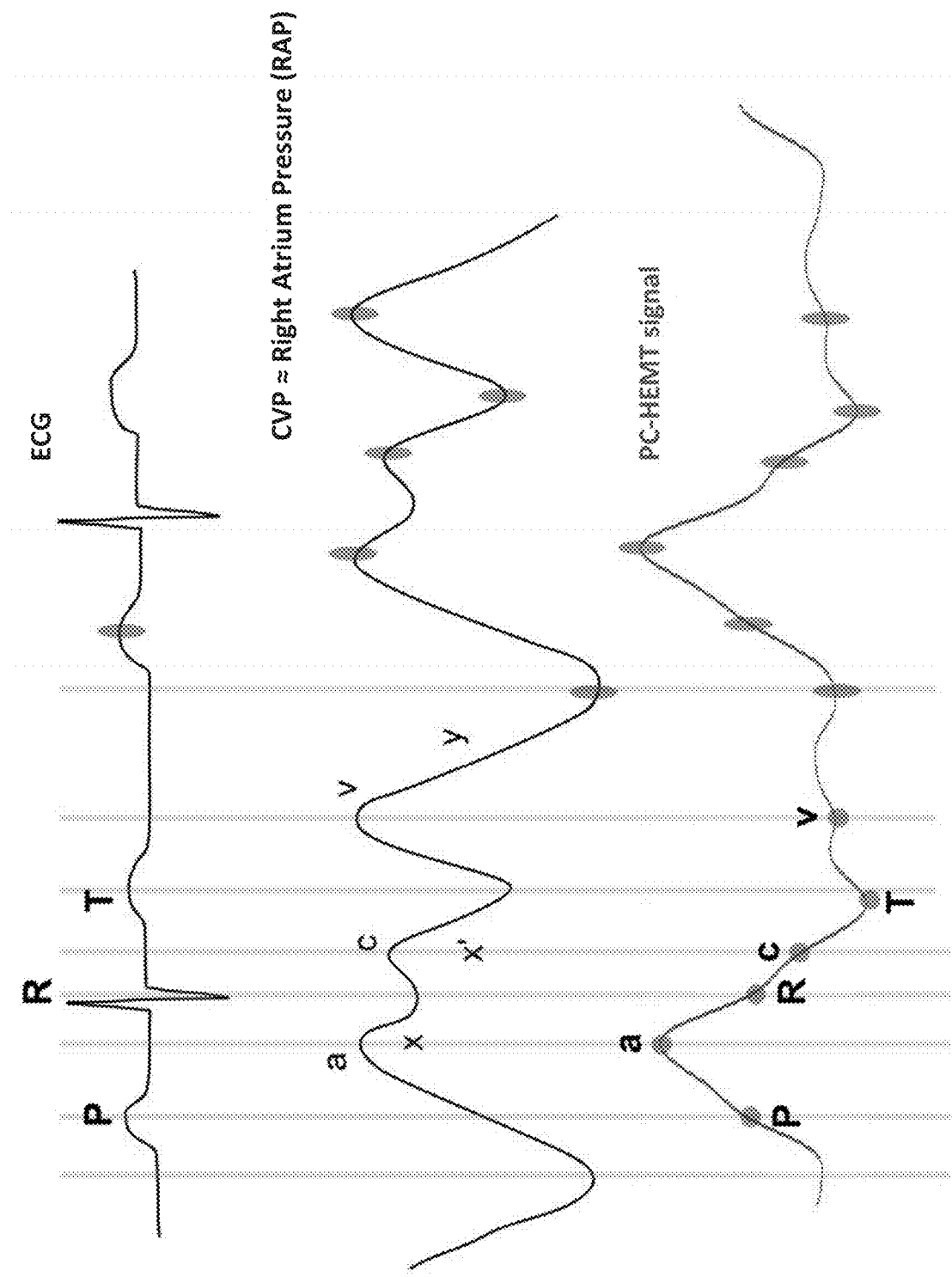
FIG. 25 shows the correlation between the cardiac signals data recorded with ECG and the CVP waveform data and with the PC-HEMT sensor.

Central venous or right atrium pressures dynamics can be measured precisely today only by means of heart catheterisation. FIG. 25 shows the experimentally obtained correlation between the ECG and CVP waveform data and cardiac signals data recorded with the PC-HEMT sensor. Since the CVP is equivalent to the right atrium pressure (RAP), the cardio signal data recorded with the PC-HEMT (bottom waveform) actually contains the ECG peak positions and CVP-RAP positions. This clearly opens new horizons for the non-invasive diagnostics of right ventricular infarction, right heart failure and cor pulmonale, tamponade, tricuspid regurgitation or stenosis, complete heart block and constrictive pericarditis using the single-point and contactless PC-HEMT sensor.

FIGS. 26a-26b shows the comparison of normal (red) and abnormal (grey) cardiac signal shape from two patients recorded with the PC-HEMT sensor. The clear difference in the waveform peaks, in their amplitude and timing immediately allows a trained doctor to diagnose the abnormalities in the heart activity of a patient.

Example 3

Ambulatory Tests

A prototype single-point measurement PC-HEMT sensor was used for an activity recording of a complete heart cycle including physical movement of right- and left heart atriums with a real time synchronisation to a heart polarisation/depolarisation electrocardiography dynamics. This technique described in the present application allows performing a non-invasive heart diagnostics, which alternatively can be only carried out by invasive right- and left atriums heart catheterisation in addition to the simultaneously recorded ECG. Moreover, the PC-HEMT sensor of some embodiments of the present application makes it possible to contact a single point on a patient's body, which is needed for carrying out the cardiac measurements. This allows the smooth integration of the PC-HEMT sensor into a wristwatch format revolutionising the whole cardiovascular and pulmonary diagnostics and therapy monitoring approach. Furthermore, using the integrated PC-HEMT sensor makes it possible to unprecedentedly improve the cardiac telemedicine in the point-of-care diagnostic and tremendously reduce the therapy expenditures in the hospitals.

The purpose of the ambulatory tests was to compare the shape and time-related features between the right atrium pressure (RAP) waveform recorded at catheter and the PC-HEMT signal on different volunteers under clinical conditions.

Figure 27:
FIG. 27 shows the ambulatory environment during the clinical tests.

Ambulatory tests including the single-point cardio-dynamics measurements were conducted at the Hospital of Giessen (UKGM Giessen, Germany), in the laboratory for the RAP catheter measurements without motion artefacts of medical personnel and intensive usage of medical devices in the lab. On the first day of the clinical tests, the EM-compatibility of the ambulatory room was evaluated. The PC-HEMT sensor has a very high charge and EM-sensitivity. During patient treatment there is normally a lot of medical equipment emitting EM-noise mainly from power supply units. Therefore, it was important to evaluate the impact of such intensive EM-environment on the PC-HEMT sensor utilisation. FIG. 27 shows the ambulatory environment during the test. In this test, the patient was laying on a bed with a wire extended Ag/AgCl ECG reference electrode, which was attached to a single-point at his left wrist. The signals were recorded from the patient's wrist.

Figure 28B:
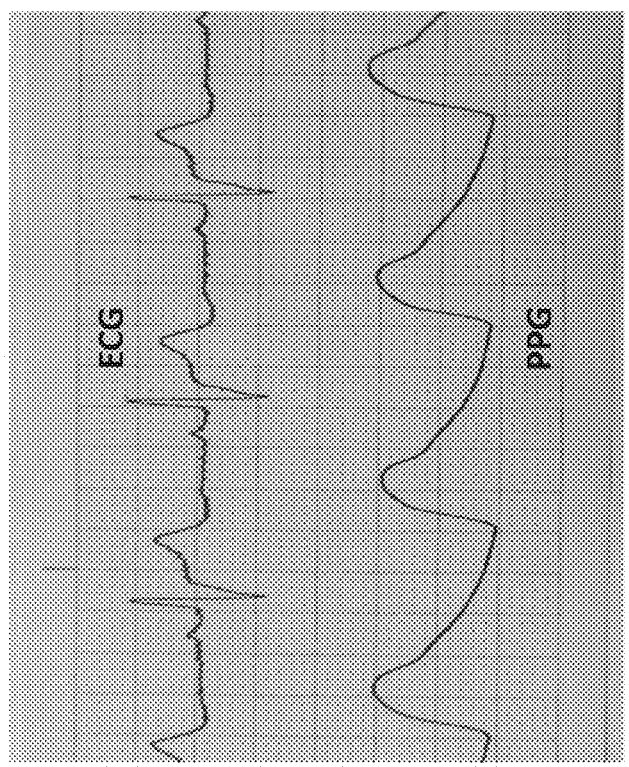
FIG. 28b shows the ECG and PPG print-outs obtained from the medical catheter control-unit for the first patient.
Figure 28A:
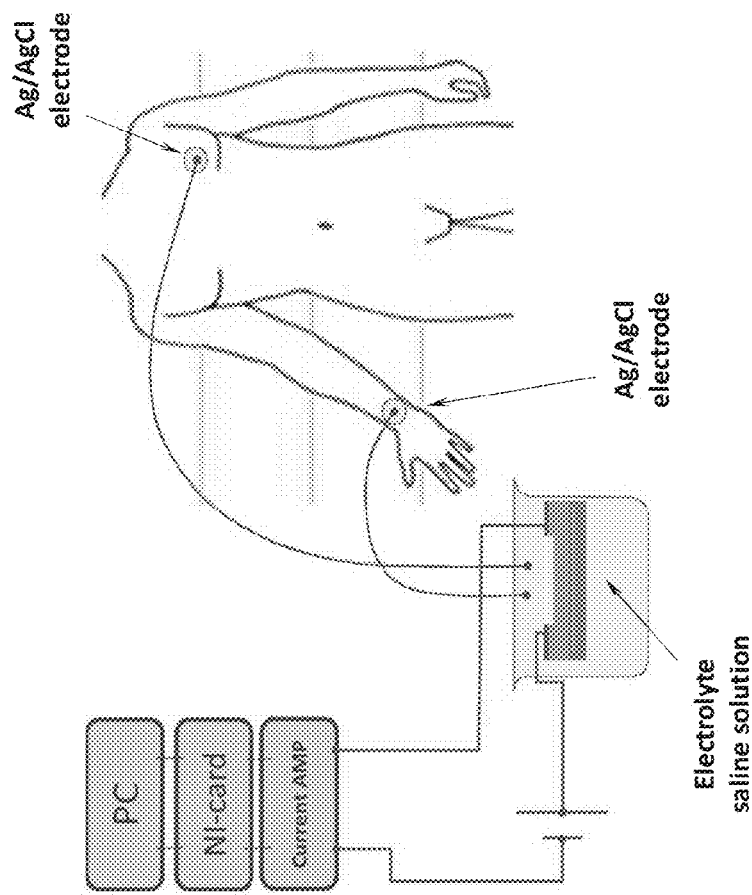
FIG. 28a schematically shows the sensor setup used in the clinical tests.

Initially, a 30-min light surgery for implantation of a pre-prepared and pre-configured sterile RAP-catheter was performed by a pneumologist. Then the RAP-profile and blood samples composition were analysed by medical personnel of the lab. Then, the electrodes of the PC-HEMT sensor were placed on the left wrist, and the sensor was placed in an electrolyte saline solution inside the light/EM protection cage. Single-point detection was performed with metallic wires bridging the Ag/AgCl ECG reference electrode on a body of the patient with the electrolyte solution. The setup is schematically shown in FIG. 28a, and the ECG and PPG (photoplethysmograph) print-outs from the medical catheter control-unit are shown in FIG. 28b. The ECG and PPG were recorded synchronously and transmitted via Bluetooth. The waveform signal from the PC-HEMT sensor was then recorded for 15-20 minutes and synchronised with the ECG/PPG signals recorded from a patient's wrist.

Figure 28C:
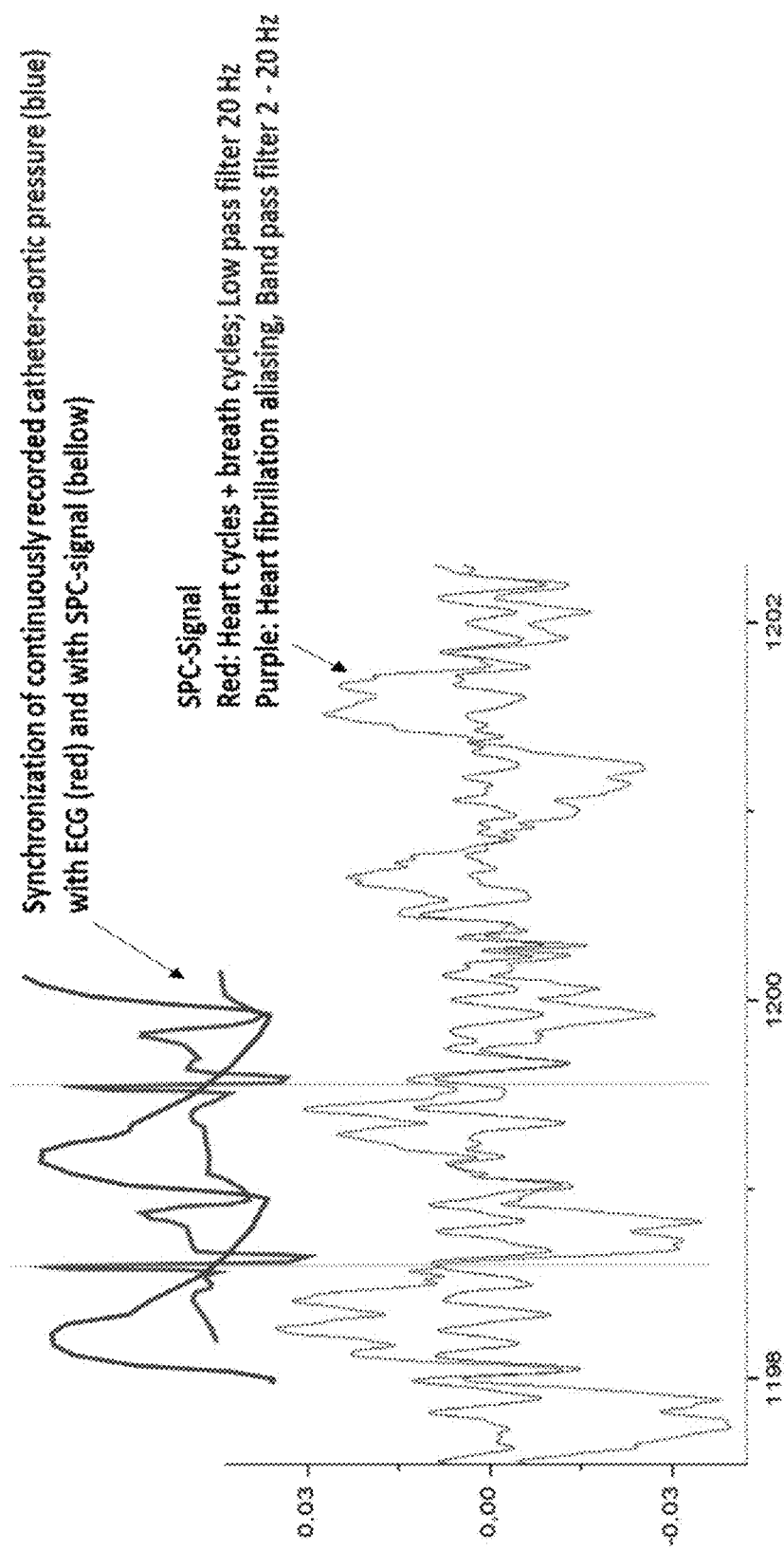
FIG. 28c shows synchronised and continuously recorded signals for catheter-aortic pressure (blue) with ECG (bold red) and with the PC-HEMT in the clinical tests with low pass filter of 20 Hz for the first patient (thin red: heart cycles plus breath cycles with a low-pass 20 Hz filter; purple: heart cycles with a band pass filter of 2-20 Hz) ("SPC" in the figure stands for "single-point cardio", and it is actually the waveform signal recorded by the PC-HEMT sensor.)

FIG. 28c shows the synchronised and continuously recorded signals for catheter-aortic pressure (blue) with ECG (bold red) and with the PC-HEMT sensor signal (thin red: heart cycles plus breath cycles with a low-pass 20 Hz filter; purple: heart cycles with a band pass filter of 2-20 Hz). As shown in FIG. 28c, strong sustained potential shift signals were recorded with no motion artefacts of medical personnel and without medical tools usage, even in the presence of electromagnetic noise. ("SPC" in FIG. 28c stands for "single-point cardio", the term defined as the signal recorded by the PC-HEMT sensor.)

Despite the clearly visible 50 Hz power line noise, it was possible to obtain the valid PC-HEMT sensor recordings after simple FFT-DSP-data filtering using a 20 Hz low-pass filter on the raw waveform data. From the shown waveform signals, the heart rate and single heart cycles can be easily extracted as will be detailed below. As can be seen from the recorded data, the breath rate of this patient was very high and even higher than a heart rate. Such fast breath is unusual. Moreover, the RAP-catheter pressure could not be measured properly due to the heart failure. In addition, the PC-HEMT sensor shows the higher frequency fibrillation inside the signal.

Figure 29A:
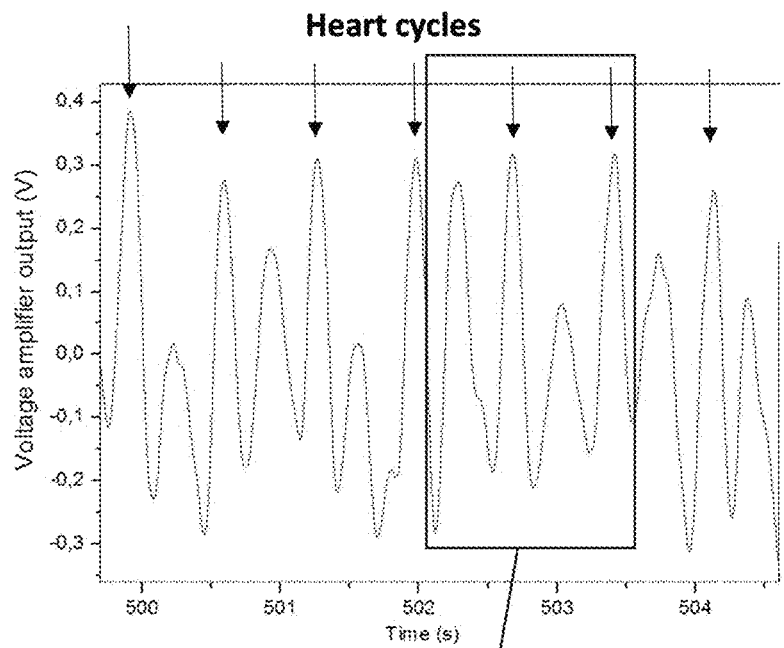
FIGS. 29a-29b shows the SPS signals from heart cycles recorded at clinical conditions with low pass filter of 20 Hz in a control test.
Figure 29B:
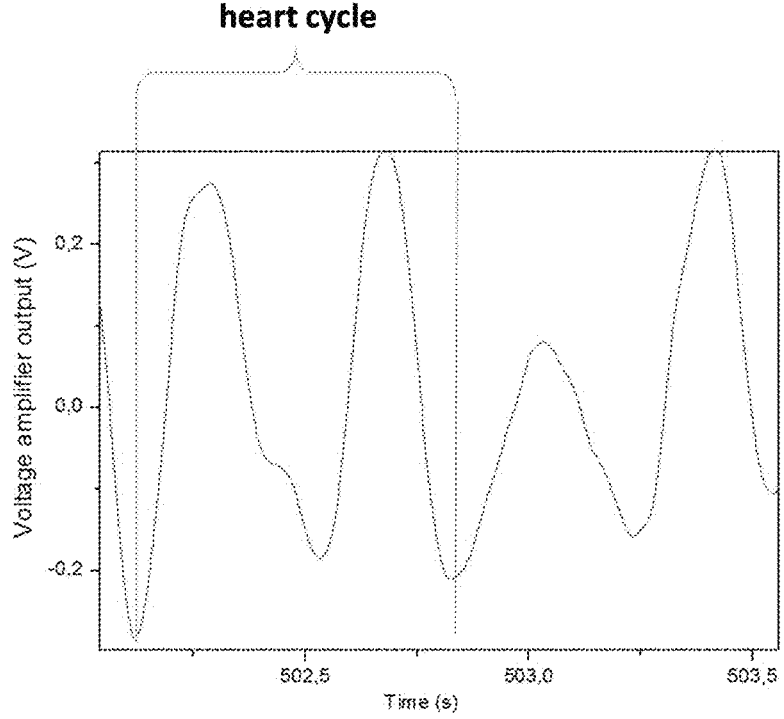

In a separate control test, strong sustained potential shift (SPS) signals shown in FIGS. 29a-29b were recorded from another volunteer in the same clinical conditions, with low pass filter of 20 Hz, with no motion artefacts of medical personnel and without medical tools usage, even in the presence of electromagnetic noise.

Figure 30B:
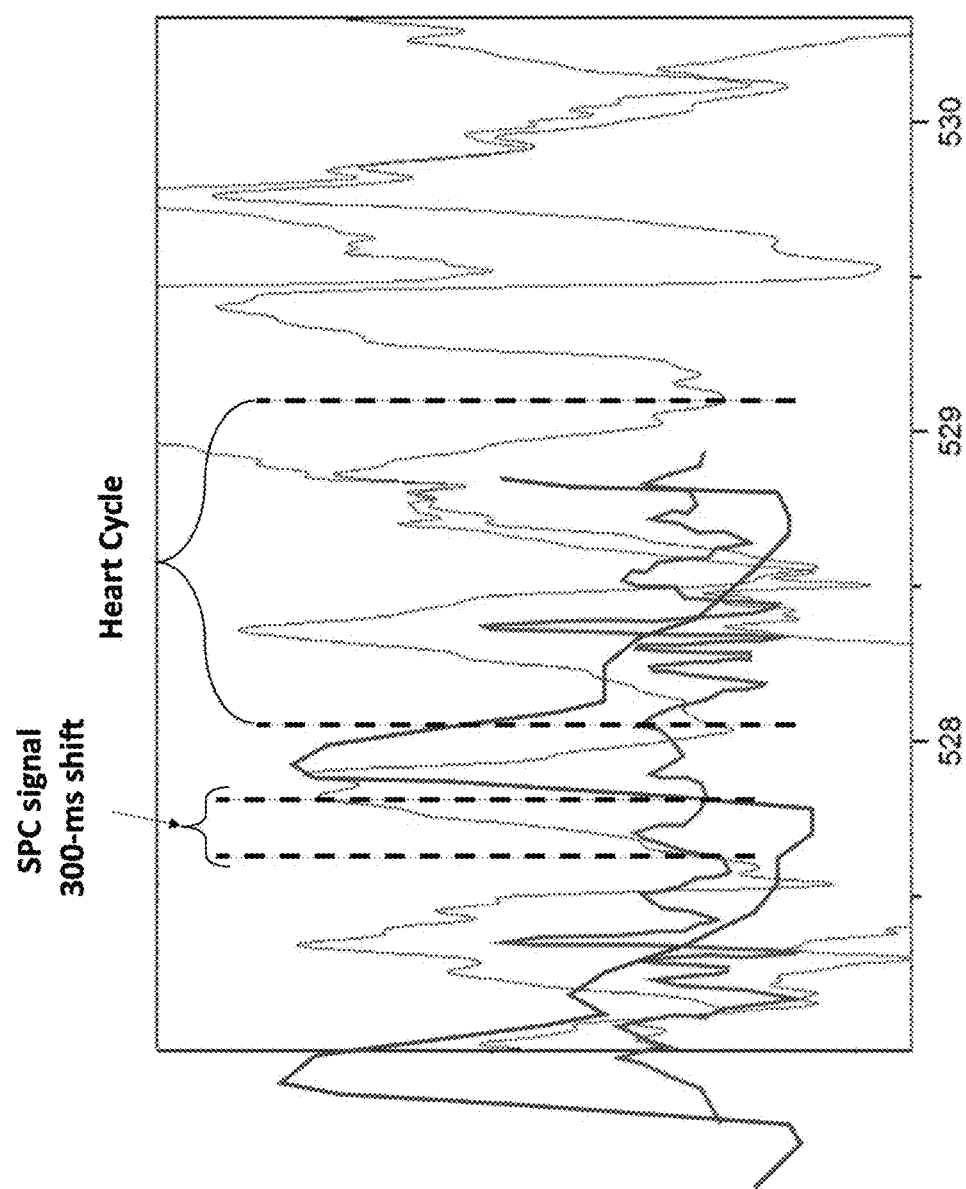
FIG. 30b shows synchronisation of continuously recorded signals for catheter-aortic pressure (blue) with ECG (bold red) and with the PC-HEMT in the clinical tests with low pass filter of 20 Hz for the second patient (thin red: heart cycles plus breath cycles with a low-pass 20 Hz filter; purple: heart cycles with a band pass filter of 2-20 Hz) ("AP" in the figure is abbreviated for "aortic pressure", and "SPC" is abbreviated for "single-point cardio", and it is actually the signal recorded by the PC-HEMT sensor.)

Another patient was operated for the RAP-catheter setting in the same lab. The PC-HEMT data recording was carried out approximately three hours after the first patient according to the same experimental sequence presented above. FIG. 30a shows the recorded ECG and PPG print-outs from the medical catheter control-unit for the second patient and his laboratory environment during the test. FIG. 30b shows synchronization of the continuously recorded signals for catheter-aortic pressure (blue) with ECG (bold red) and with the PC-HEMT sensor signal (thin red: heart cycles plus breath cycles with a low-pass 20 Hz filter; purple: heart cycles with a band pass filter of 2-20 Hz). ("AP" in the figure stands for "aortic pressure", and "SPC" stands for "single-point cardio", and it is actually the signal recorded by the PC-HEMT sensor.)

As can be seen from the recorded data for the second patient, it was still impossible to obtain the stable RAP signal. However, it was possible to record a very stable PC-HEMT signal shown in FIG. 30b. The PC-HEMT signal exhibited a full heart cycle with two major characteristic peaks. Upon synchronisation and comparison of the signals in FIG. 30b, it became clear that the PC-HEMT signals are about 300 ms ahead of the PPG signals. This experimental evidence supported the phenomenal idea that the physical origin of the signal recorded by the PC-HEMT sensor is actually an electric field accompanied by shown heart motion, which typically does not have the pulse transit time behaviour of a photoplethysmograph.

Figure 31A:
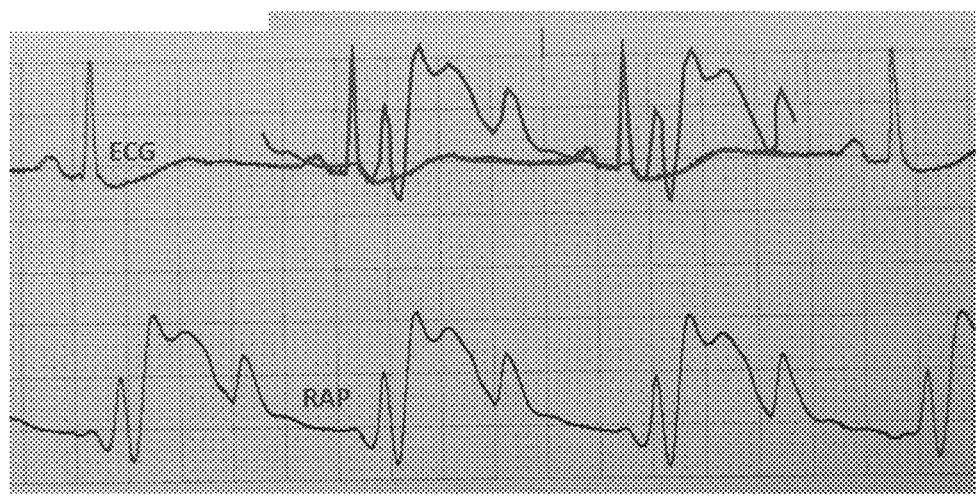
FIG. 31a shows the ECG and PPG print-outs from the medical catheter control-unit for the third patient.
Figure 31B:
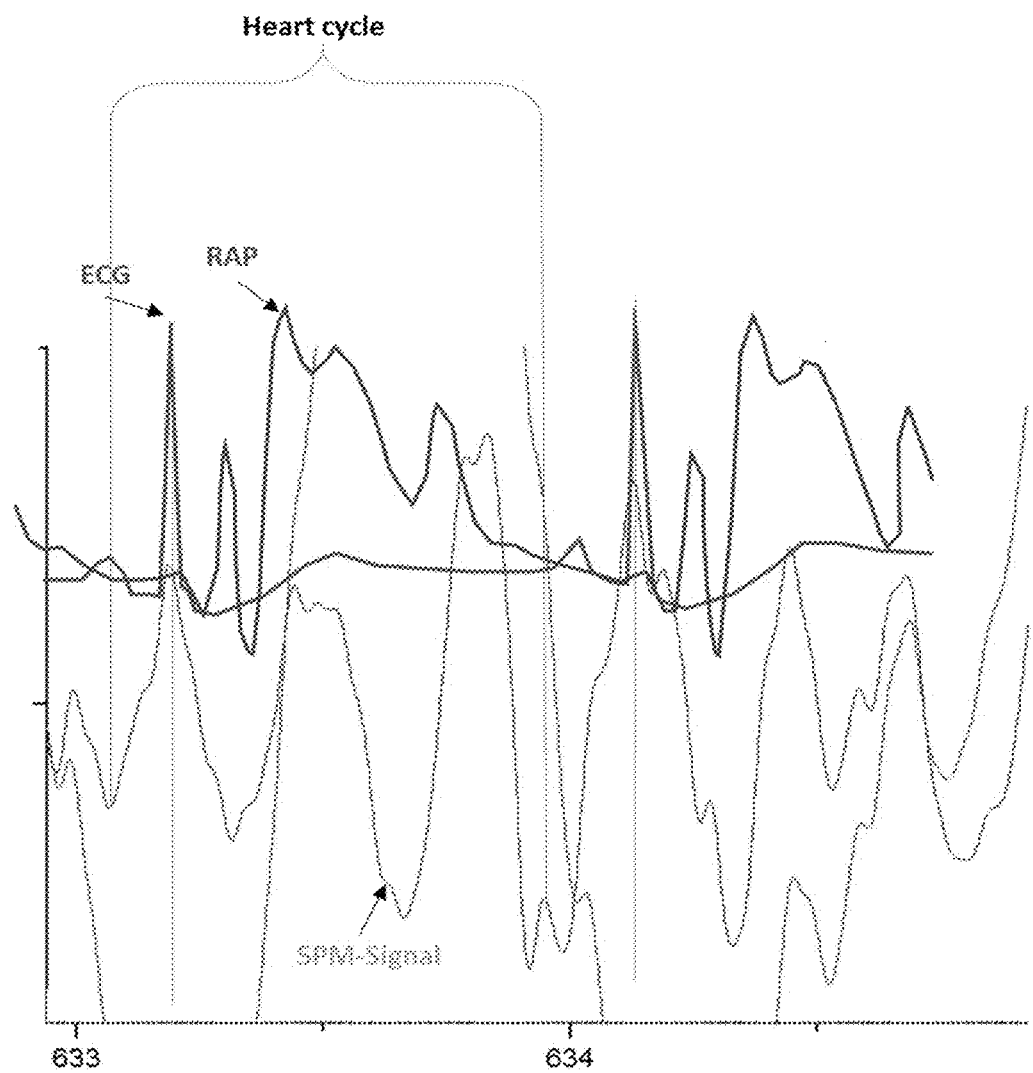
FIG. 31b shows synchronisation of continuously recorded signals for catheter-right atrium pressure (bold purple line) with the PC-HEMT signal (thin red line for heart cycles plus breath cycles with a low-pass 20 Hz filter and thin purple line) and ECG (bold red line) in the clinical test for the third patient ("RAP" in the figure stands for "catheter-right atrium pressure", and "SPM" is abbreviated for "single-point monitoring", and it is the signal recorded by the PC-HEMT sensor.)

In the next test, for the third patient, the RAP signal was recorded in parallel, which was synchronized with the PPG/ECG and with the PC-HEMT signals and is shown in FIGS. 31a-31b. The RAP signal recorded for this patient differs from the previous patients showing some splits. As seen in FIG. 31b, these splits are observable in the PC-HEMT waveform demonstrating a unique splitting during a heart cycle.

Figure 32A:
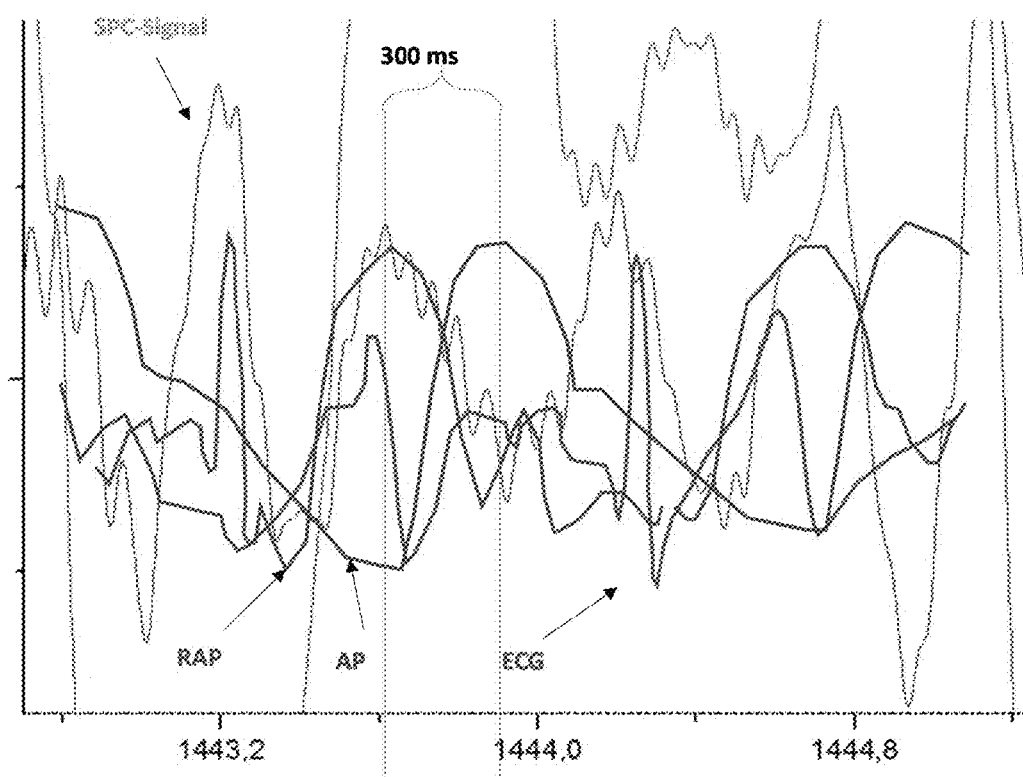
FIGS. 32a-32b show synchronization of continuously recorded signals from catheter RAP (purple line), aortic pressure (AP, blue line), ECG (red line) and the PC-HEMT sensor (purple line recording heart cycles with a band pass filter of 2-20 Hz).

Another patient with high lung pressure was diagnosed in the same laboratory. Reference is made to FIG. 32a demonstrating synchronization of continuously recorded signals from catheter RAP (purple line), aortic pressure (AP, blue line), ECG (red line) and the PC-HEMT sensor (purple line recording heart cycles with a band pass filter in the range of 2-20 Hz). This trial was conducted with small motion artefacts of medical personnel and with intensive medical tools usage, including the RAP-catheter control unit, ECG, PPG, spirometer, ultrasound, blood radiometer (blood composition spectral analyser) and ventilator.

Figure 32B:
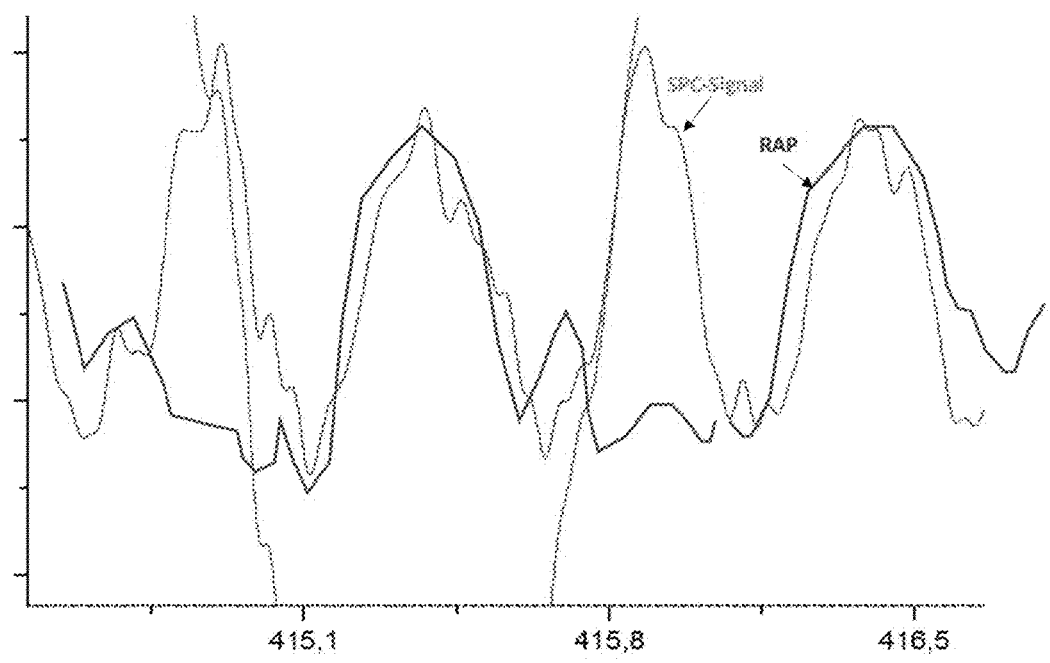

FIG. 32b shows a synchronised graph of the RAP and PC-HEMT signal. It is clearly seen from the synchronised graphs that the RAP dynamics is very similar to the signal dynamics recorded with the PC-HEMT sensor. To sum up, the PC-HEMT signals were successfully detected at the hospital conditions. Comparison of the PC-HEMT and AP signals showed a 300 ms time lead of the former, which is more typical for the RAP dynamics. Comparison of the PC-HEMT and RAP signals clearly demonstrates the full time equivalent dynamics for cardiovascular monitoring. In fact, while the RAP catheter delivers information only about a right heart side, the PC-HEMT sensor of some embodiments of the present application is capable of non-invasive measuring of both the right and left atrium pressures.

Example 4

Single-Point Clinical Tests

Figure 33:
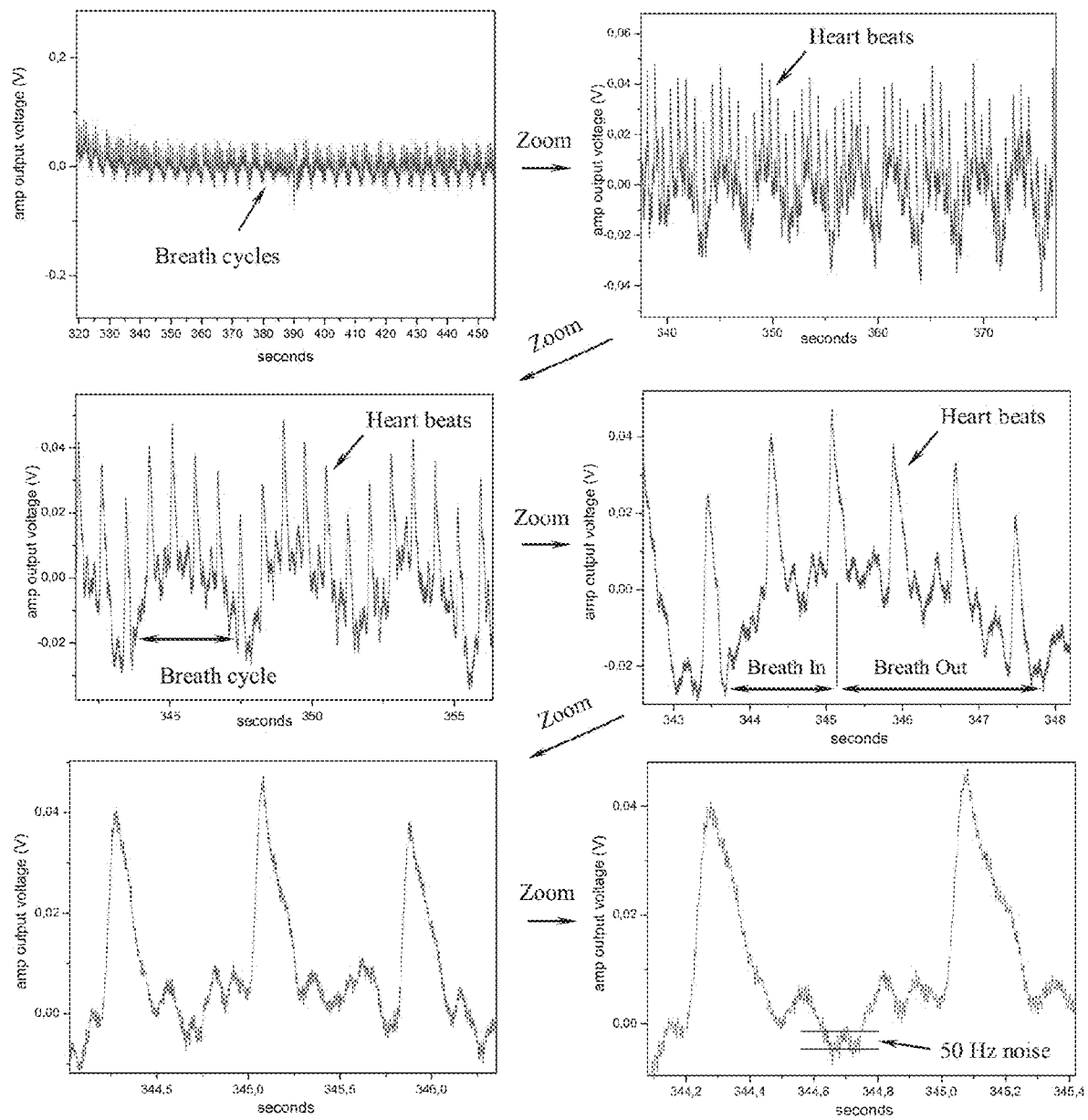
FIG. 33 shows recorded cardiovascular activity at a single body point on the left wrist in zoom-in figures sequence.
Figure 34:
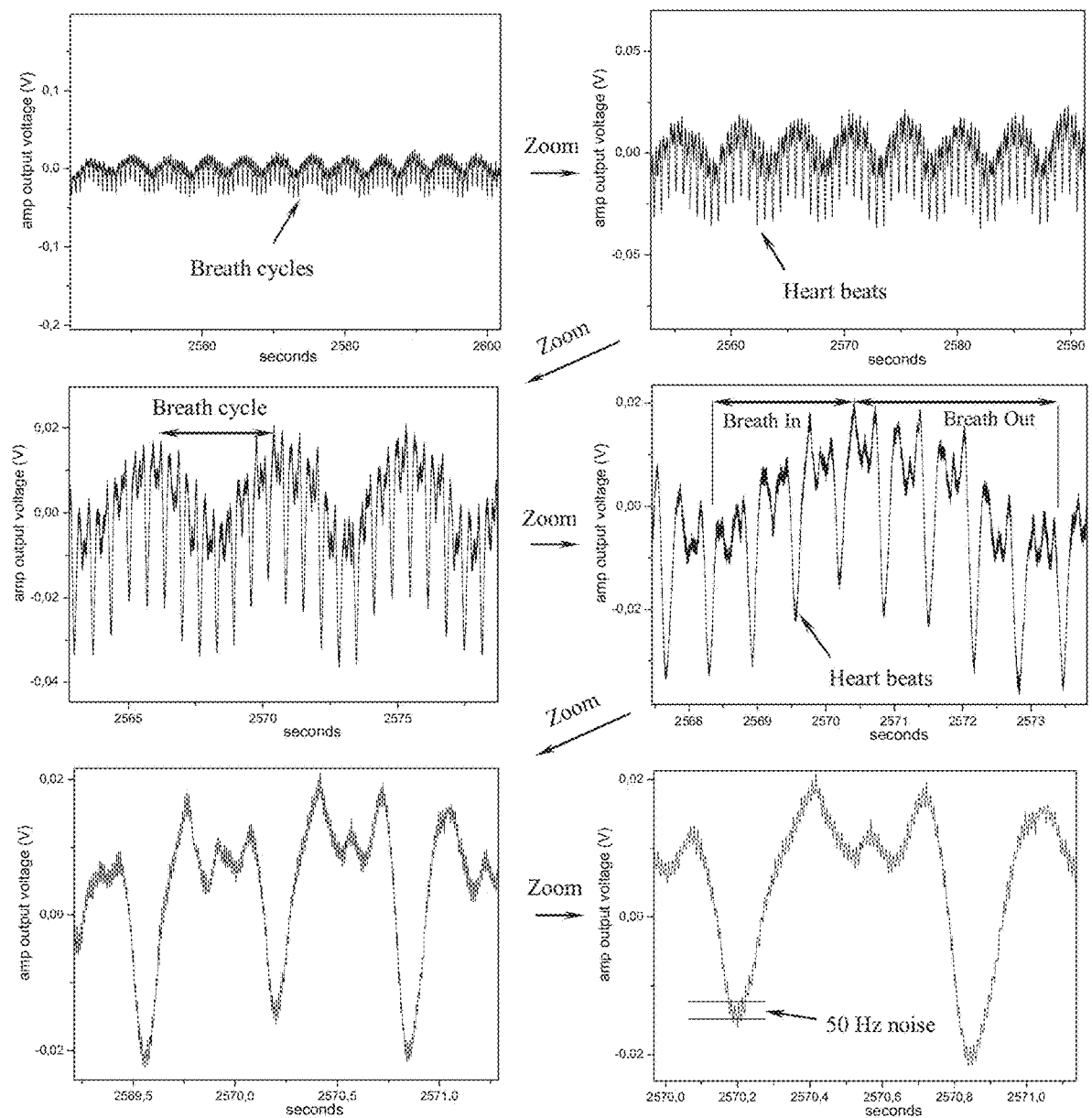
FIG. 34 shows recorded cardiovascular activity at a single body point on the right wrist in zoom-in figures sequence.
Figure 35:
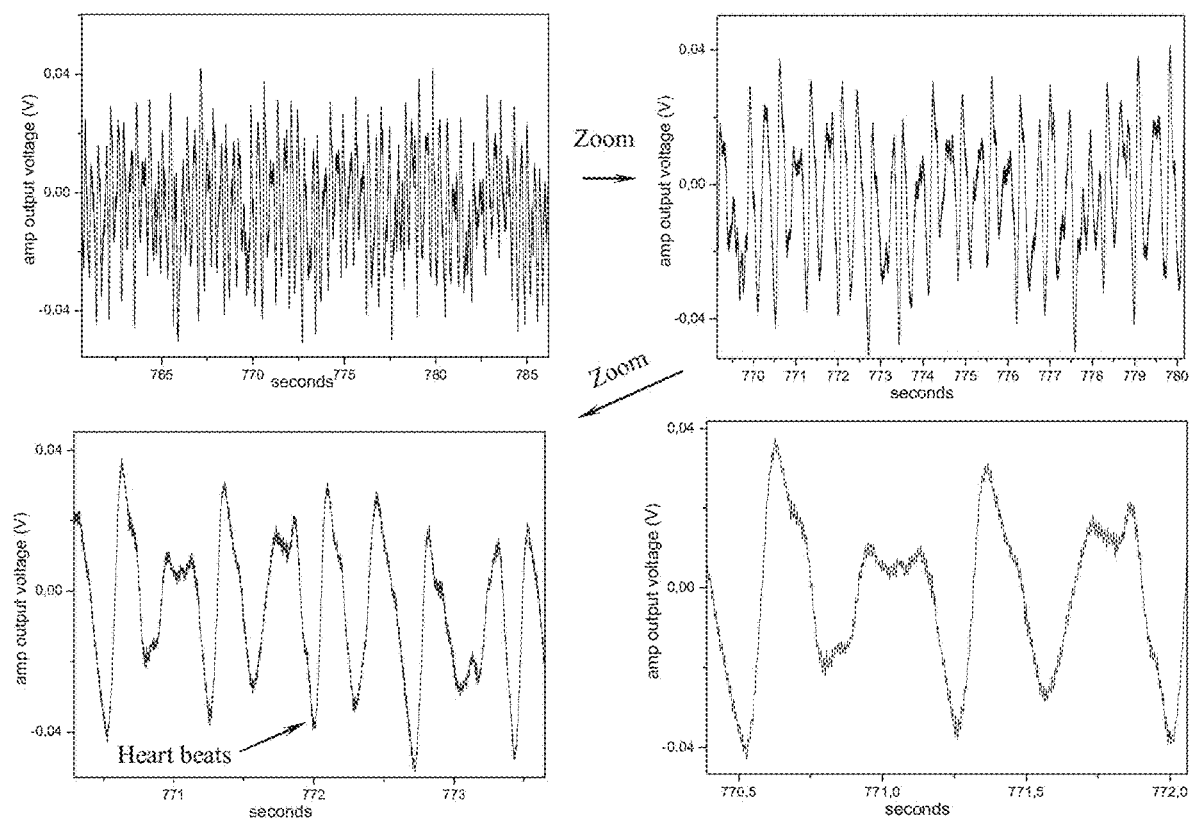
FIG. 35 shows recorded cardiovascular activity measured within oral cavity in zoom-in figures sequence.

The next set of clinical trials has been conducted on a single body point sequentially, first on the left and right wrist positions followed by the measurements on heart, neck and in oral cavity. All the measurements were carried out using current amplifier with a 6 dB bandwidth filter (0.3-30 Hz) and sensitivity (amp factor) of 200 nA/V with input resistance of 10 kOhm. The single body heart signals obtained on the left hand are shown in FIG. 33 in zoom-in figures sequence. The single body heart signals obtained on the right hand are shown in FIG. 34. The signals recorded at both left and right wrists are shape-identical but exhibit opposite polarity due to the natural heart dipole projection in limbs fully conforming above experiments. FIG. 35 demonstrates the single point heart signals measured within oral cavity in zoom-in figures sequence. During the signal recording inside the oral cavity, the breath oscillations are much smaller compared with wrist signals and the cardiac signal do not anymore exhibit a pronounced upwards or downward orientation of the sharpest heart polarisation cycle peaks.

Example 5

Demonstration of a Huge Intrinsic Amplification Phenomenon

Figure 36A:
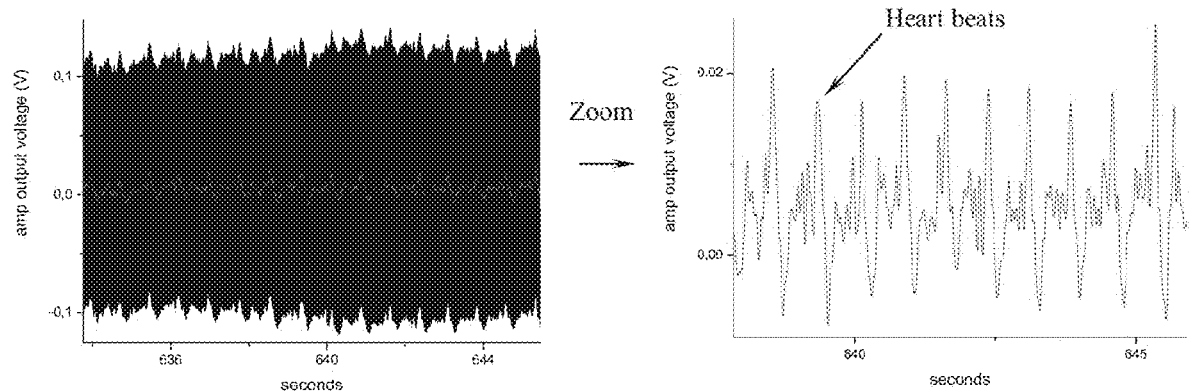
FIG. 36a shows the cardiac signals recorded at a single body point inside the building exposed to a power line of 50 Hz parasitic electromagnetic field. The signals were modulated with 50 Hz noise, in-plane $V_{GS}=-1.6V$ and amp gain 500, and plotted after 10 Hz low-pass (LP) filter.
Figure 36B:
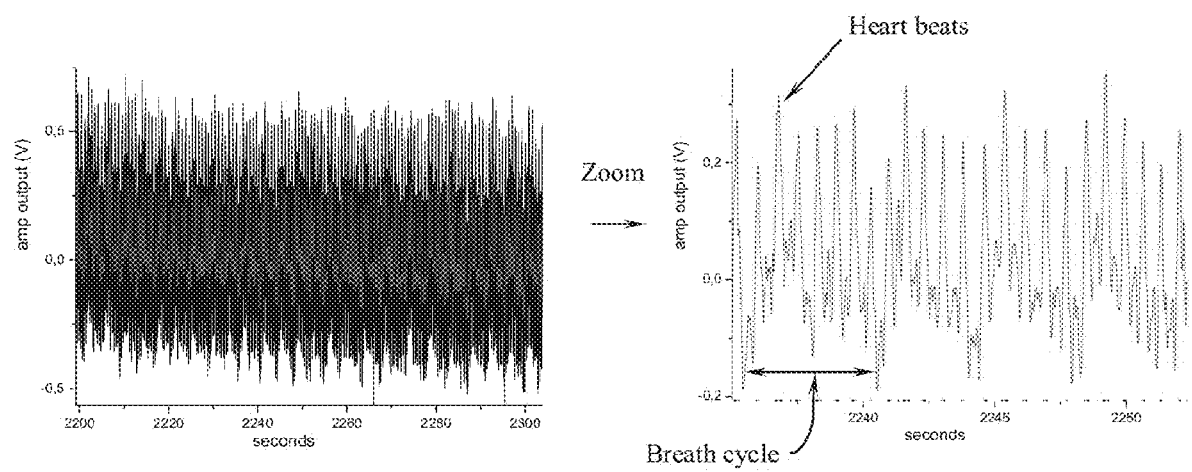
FIG. 36b shows the cardiac recorded at a single body point inside the building exposed to a power line of 50 Hz parasitic electromagnetic field. The signals were modulated with 50 Hz noise, in-plane $V_{GS}=0V$ and amp gain 500, and plotted after 10 Hz LP filter.

A series of experiments on increase of the signal stability by means of in-plane gating effect is demonstrated in this example. These experiments show cardiovascular signals well detected indoor in the presence of surrounding 50 Hz noise in Faraday cage protecting the sensor. FIG. 36a shows the cardiac signals recorded at a single body point inside the building exposed to a power line of 50 Hz parasitic electromagnetic field. The signals were modulated with 50 Hz noise, in-plane $V_{GS}=-1.6V$ and amp gain 500, and plotted after 10 Hz LP filter. FIG. 36b shows the same cardiac signals recorded with 50 Hz noise, in-plane $V_{GS}=0V$ and amp gain 500, and plotted after 10 Hz LP filter. Thus, despite a strong parasitic 50 Hz noise, it is possible to detect a cardiac signals at single body point with rather high signal-to-noise ratio. This parasitic modulation can be easily filtered out using simple (10 Hz-20 Hz low pass) mathematical data processing.

Figure 37A:
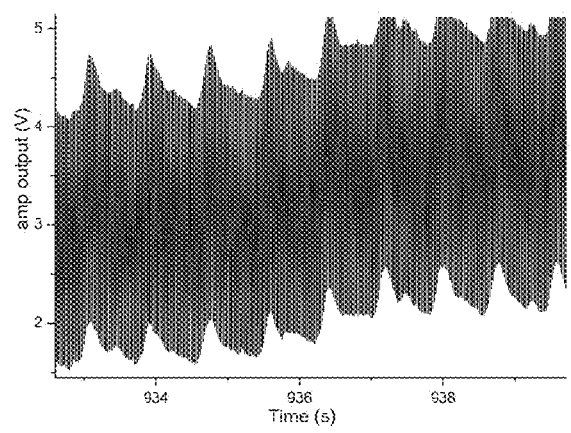
FIG. 37a shows the cardiac signals recorded at a single body point inside the building exposed to a power line of 50 Hz parasitic electromagnetic field. The signals were modulated with 50 Hz noise and amp gain 1000, and plotted after 10 Hz LP filter.
Figure 37B:
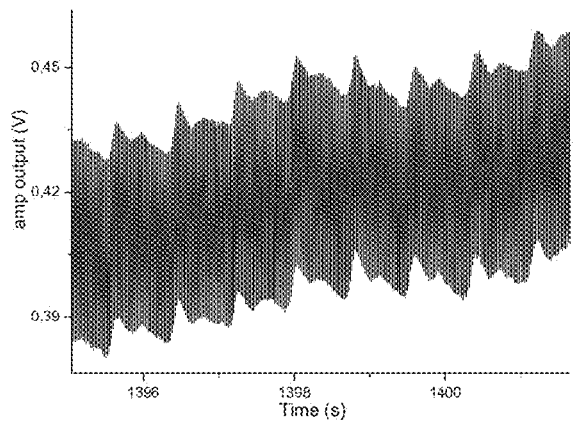
FIG. 37b shows the cardiac signals recorded at a single body point inside the building exposed to a power line of 50 Hz parasitic electromagnetic field. The signals were modulated with 50 Hz noise and zero (0) amp gain, and plotted after 10 Hz LP filter.

A huge intrinsic amplification phenomenon of the PC-HEMT sensor is demonstrated in FIGS. 37a-37b showing the cardiac signals recorded at a single body point inside the building exposed to a power line of 50 Hz parasitic electromagnetic field. In FIG. 37a, the signals were modulated with 50 Hz noise and amp gain 1000, and plotted after 10 Hz LP filter, while in FIG. 37b, the amp gain was zero. Thus, such increase in the amplification factor immediately results in the 100% modulation of the sensor current. Since the PC-HEMT signal is tremendously amplified, it is possible to operate the sensor without any additional (external) current amplifier, thereby simplifying an electronic circuit of the sensor and significantly lowering its mass production cost.

Example 6

Recording a Phonocardiogram (PCG) Using the PC-HEMT Sensor

The PC-HEMT sensor of the present invention can successfully replace a medical stethoscope used in listening to the internal sounds of a human body (phonocardiography). A series of experiments on recording electrical signals corresponding to physiological splits of the second heart sound (S2), while the patient breathes in and out, from a single spot on the patient's wrist, is demonstrated in this example.

Different heart abnormalities cause different heart sounds resulted from abnormal heart dynamics. The second heart sound (S2) is created by closing of the aortic valve followed by closing of the pulmonic valve. The physiological S2-split phenomena of the heart sound effect occurs during a deep inspiration and breath hold, where the second heart sound, which is normally observed as a single objective tone recorded with a stethoscope, is splitting into a two clearly separated sounds, conditional to normal activity of a healthy heart. Careful analysis of the splitting and intensity of the S2 can indicate the presence of many cardiovascular diseases. The splitting varies between zero and eighty milliseconds depending on the specific phase of the respiratory cycle. The aortic component of S2 (S2A) precedes the pulmonic component (S2P).

Figure 38A:
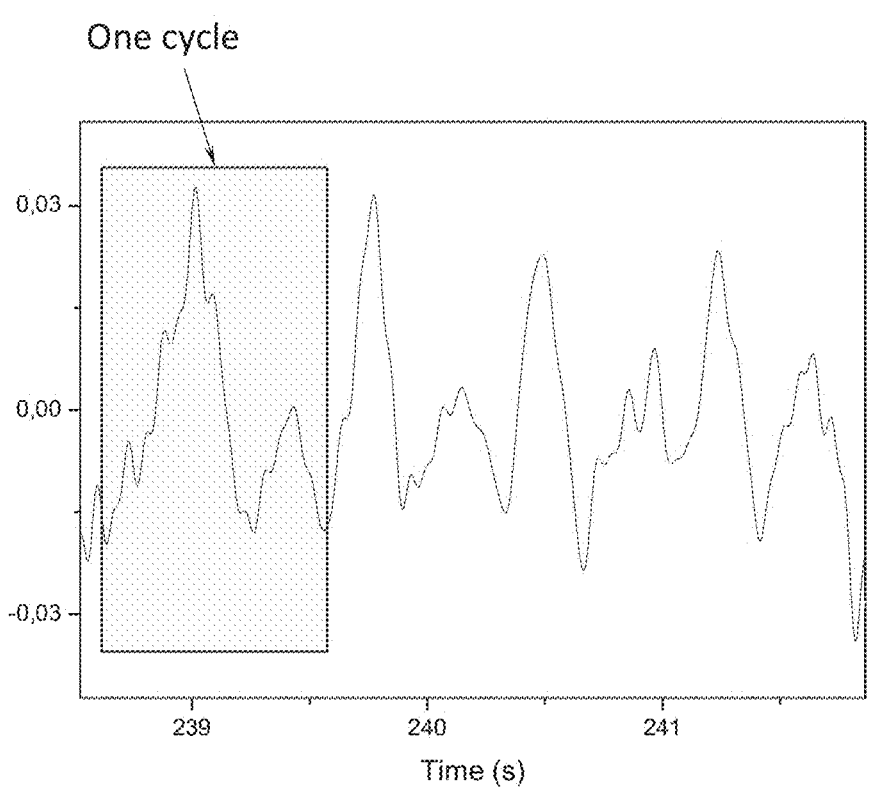
FIG. 38a shows the cardiac signals (four cardiac cycles) recorded at a single body point (a wrist) at breath-out phase (expiration) during the normal breath rhythm.
Figure 38B:
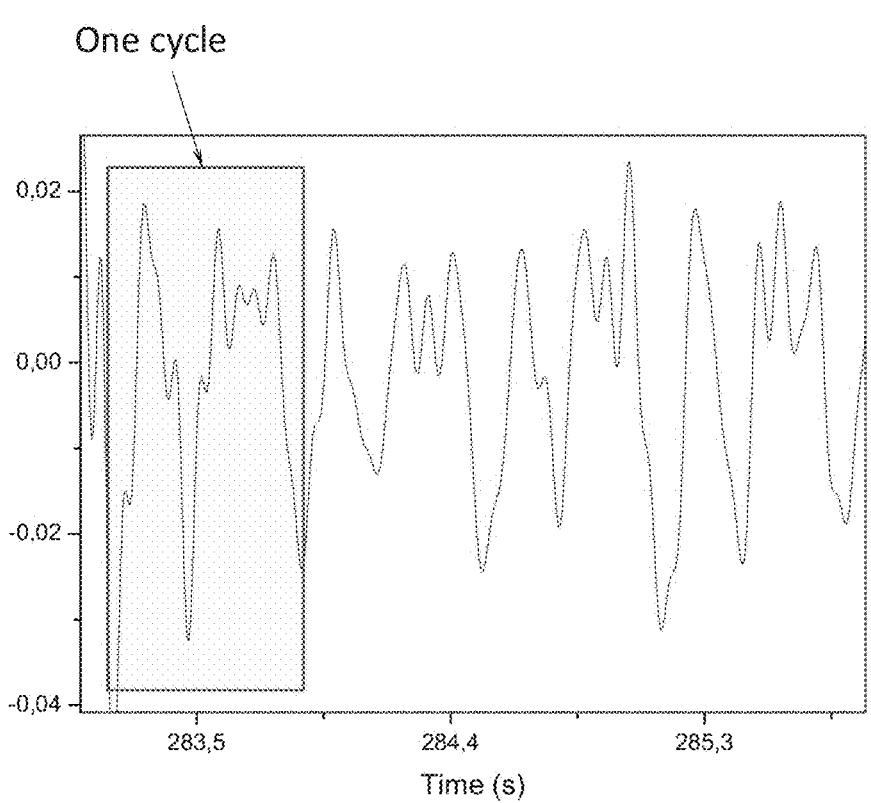
FIG. 38b shows the cardiac signals recorded at a wrist during the continuous breath-in for 20-30 sec (deep inspiration).

Using the PC-HEMT sensor makes it possible to obtain the phonocardiography data from the patient's wrist. The actual measurements were conducted for 30-45 sec with holding breath after each inspiration during the signal recording. The single point signal recorded for the cycle of inspiration and breath hold was compared with the signal obtained during the normal breath. FIG. 38a shows the cardiac signals (four cardiac cycles) recorded at a single body point (a wrist) at breath-out phase (expiration) during the normal breath rhythm, while FIG. 38b shows the cardiac signals recorded at a wrist during the continuous breath-in for 20-30 sec (deep inspiration). As shown in FIG. 38b, the signals recorded during the deep inspiration and breath holding are different from the expiration cycle signals shown in FIG. 38a. The former can be easily identified by the splitting of the second smaller peak into three sub-peaks within the same single heart cycle.

Figure 39:
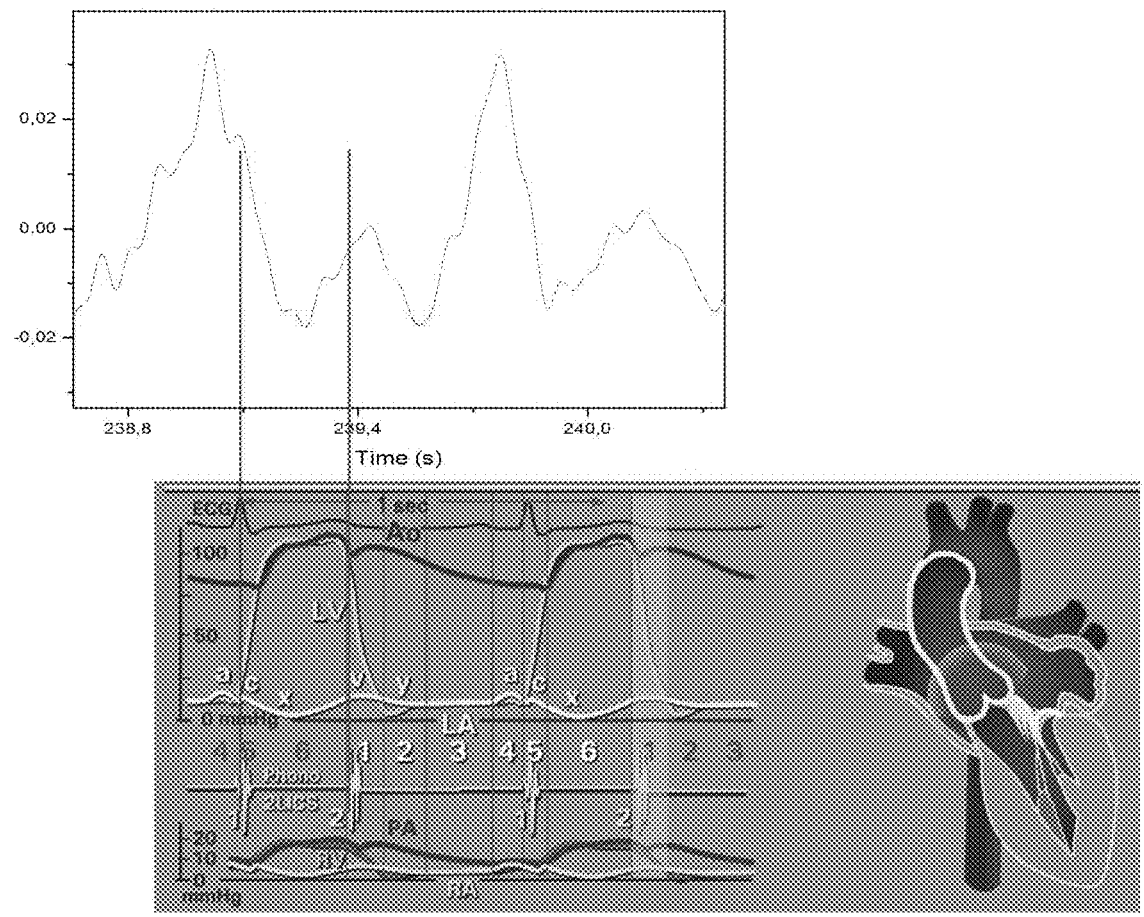
FIG. 39 shows the cardiac signals (two cycles) recorded with the PC-HEMT sensor at breath-out phase during the normal breath rhythm and time-synchronized with a referential biophysical cardiac dynamics cycle.
Figure 40:
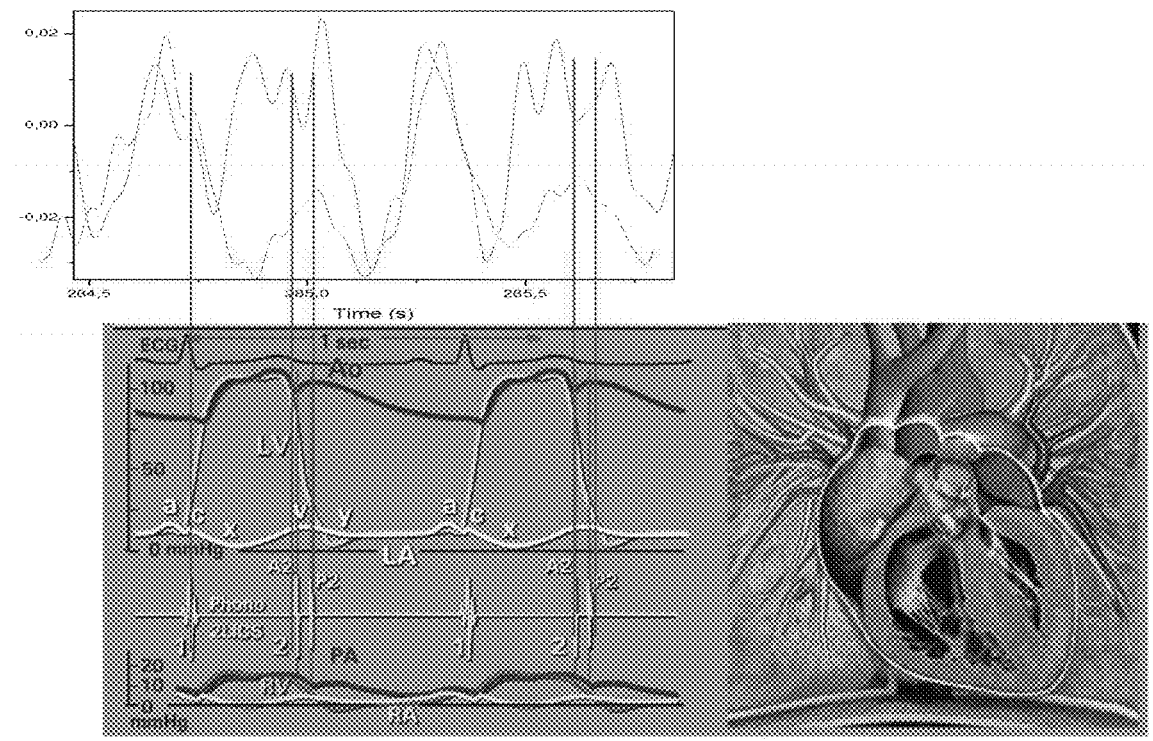
FIG. 40 shows the cardiac signals (two cycles) recorded with the PC-HEMT sensor during continuous breath-in for 20-30 sec (red solid line) and time-synchronized with a referential biophysical cardiac dynamics cycle. The cardiac signals (two cycles) during the breath-in phase are shown in the background (blue dashed line).

FIG. 39 shows the cardiac signals recorded with the PC-HEMT sensor at the breath-out phase (two cycles) during the normal breath rhythm and time-synchronized with a referential biophysical cardiac dynamics cycle. FIG. 40 shows the cardiac signals (two cycles) recorded with the PC-HEMT sensor during continuous breath-in for 20-30 sec (red solid line) and time-synchronized with a referential biophysical cardiac dynamics cycle. The cardiac signals (two cycles) during the breath-in phase are shown in the background (blue dashed line).

The experimental results presented in FIGS. 38-40 clearly demonstrates that the characteristic PCG S2-split into A2-P2 peaks correlates with the peak splitting recorded with the present sensor. The signals recorded with the PC-HEMT sensor clearly represent the differences between breath-in and breathe-out phases. Thus, the PC-HEMT sensor can detect the S2-split phenomena and the whole breath dynamics using the measurements at a single point on a patient's body and can be seen as a future substitute for a stethoscope.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

REFERENCES

J. Malmivuo, R. Plonsey, in book: *Bioelectromagnetism—Principles and Applications of Bioelectric and Biomagnetic Fields*, Chapter 15: 12-Lead ECG System, pp. 277-289, Publisher: Oxford University Press (1975).

S. Nakayama, K. Sawamura, K. Mohri, T. Uchiyama, "Pulse-Driven Magnetoimpedance Sensor Detection of Cardiac Magnetic Activity", Plos One, Volume 6, Issue 10, e25834, 2011.

J. An, H. Li, L. Miao, S. Qin, "A Study on Human Magnetocardiogram Using Giant Magneto-impedance Sensor", Second International Conference on Electronics, Communications and Control, 2012.

Y. Kado, M. Shinagawa, "*RedTacton* Near-body Electric-field Communications Technology and Its Applications", NTT Technical Review, Vol. 8, No. 3, March 2010.

S. D. Burnham, K. Boutros, P. Hashimoto, C. Butler, D. W. S. Wong, M. Hu, and M. Micovic, "Gate-recessed normally-off GaN-on-Si HEMT using a new $O_2$—$BCl_3$ digital etching technique", Phys. Status Solidi C, vol. 7, no. 7-8, pp. 2010-2012, 2010.

C. Y. Chang, S. J. Pearton, C. F. Lo, F. Ren, I. I. Kravchenko, A. M. Dabiran, A. M. Wowchak, B. Cui, and P. P. Chow, "Development of enhancement mode AlN/GaN high electron mobility transistors", Appl. Phys. Lett., vol. 94, no. 26, p. 263505, 2009.

H. Chen, M. Wang, and K. J. Chen, "*Self-aligned enhancement-mode AlGaN/GaN HEMTs using 25 keV fluorine ion implantation*", in Device Research Conference (DRC), 2010, pp. 137-138.

M. Eickhoff, O. Ambacher, "*Piezoresistivity of $Al_xGa_{1-x}N$ layers and $Al_xGa_{1-x}N$/GaN heterostructures*", Journal of Applied Physics 90, 3383 (2001).

The invention claimed is:

1. A microelectronic sensor for non-invasive monitoring of at least one physiological parameter of a patient, comprising at least one open-gate pseudo-conductive high-electron mobility transistor, printed on a flexible printed circuit board (PCB), and connected to its dedicated electrical contact line printed on said PCB;

wherein said transistor comprises:
(a) a multilayer hetero-junction structure made of gallium nitride (GaN) and aluminium gallium nitride (AlGaN) single-crystalline or polycrystalline semiconductor materials, and deposited on a substrate layer or placed on free-standing membranes; said structure comprising at least one buffer layer and at least one barrier layer, said layers being stacked alternately;
(b) a conducting channel comprising a two-dimensional electron gas (2DEG) or a two-dimensional hole gas (2DHG), formed at an interface between said buffer layer and said barrier layer, and upon applying a bias to said transistor, becoming capable of providing electron or hole current, respectively, in said transistor between source and drain contacts;
(c) source and drain contacts connected to said 2DEG or 2DHG conducting channel and to electrical metallizations for connecting said transistor to an electric circuit; and
(d) an open gate area between said source and drain contacts;
said transistor is characterised in that a thickness of the top layer of said heterojunction structure in the open gate area is 5-9 nanometres (nm) and a surface of said top layer has a roughness of 0.2 nm or less, wherein the combination of said thickness and said roughness of the top layer upon applying a bias to said transistor, creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor.

2. The microelectronic sensor of claim 1, wherein the source and drain contacts of said transistor are ohmic.

3. The microelectronic sensor of claim 1, wherein the electrical metallizations of the transistor are capacitively-coupled to the 2DEG or 2DHG conducting channel for inducing displacement currents, thus resulting in said source and drain contacts being non-ohmic.

4. The microelectronic sensor of claim 1, wherein the transistor further comprises a dielectric layer deposited on top of the multilayer hetero junction structure.

5. The microelectronic sensor of claim 1, wherein the thickness of the top layer of the transistor in the open gate area is 6-7 nm, or 6.2-6.4 nm.

6. The microelectronic sensor of claim 1, wherein the surface roughness of said recessed top layer in the open gate area is 0.1 nm or less, or 0.05 nm or less.

7. The microelectronic sensor of claim 1, further comprising:
   a voltage source connected to said electrical contact line via an electric circuit for supplying electric current to said transistor;
   an integrated or complementary metal oxide semiconductor (CMOS) current amplifier connected to said voltage source for amplification of an electric current obtained from said transistor;
   an analogue-to-digital converter (ADC) with in-built digital input/output card connected to said current amplifier for outputting the converted signal to a user interface, external memory or readout module; and
   a wired or wireless connection module for connecting said sensor to said user interface, external memory or readout module.

8. The microelectronic sensor of claim 7, further comprising at least one of:
   a feedback control microcontroller unit (MCU) for energy level adjustment and de-trapping via an external or integrated gate electrode;
   a reference electrode for remote potentiometric body charge detection; or
   a gate electrode for discharging parasitic electric current.

9. The microelectronic sensor of claim 1, wherein the transistor further comprises an excitation light source for irradiating the multilayer hetero-junction structure, thereby inducing an electric current in the 2DEG or 2DHG conducting channel.

10. The microelectronic sensor of claim 9, wherein said excitation light source is a laser diode or LED.

11. The microelectronic sensor of claim 9, further comprising:
   a voltage source connected to said electrical contact line via an electric circuit for supplying electric current to said transistor;
   a modulated light source for irradiating said transistor;
   a lock-in amplifier connected to said voltage source for amplification of a signal with a known carrier wave obtained from said transistor and increasing the signal-to-noise ratio;
   an analogue-to-digital converter with in-built digital input/output card connected to said lock-in amplifier for outputting the converted signal to a user interface, external memory or readout module;
   a feedback control microcontroller unit (MCU) for energy level adjustment and de-trapping via an external or integrated gate electrode; and
   a wired or wireless connection module for connecting the sensor to the user interface, external memory or readout module.

12. The microelectronic sensor of claim 1, further comprising:
   one or two out-input RFID-tag zero-power fractal antennas, each connected to said electrical contact line via an electric circuit for receiving or transmitting a signal;
   a diode input-output separator to separate polarities in said circuit;
   an integrated circuit for storing and processing said signal, and for modulating and demodulating a radio-frequency (RF) signals, said circuit comprising:
   a) a voltage source supplying electric current to said transistor and to said one or two antennas;
   b) an integrated or complementary metal oxide semiconductor (CMOS) current amplifier for amplification of an electric current obtained from said transistor;
   c) an analogue-to-digital converter (ADC) with wireless input/output modules connected to said current amplifier for wireless outputting the converted signal to a user interface, external memory or readout module;
   d) a microcontroller unit (MCU) for processing and converting the received signal into data readable in said user interface, external memory or readout module; and
   e) a wireless connection module for wirelessly connecting said sensor to said user interface, external memory or readout module.

13. The microelectronic sensor of any one of claim 7, further comprising at least one of:
   1) a reference electrode for remote potentiometric body charge detection, or
   2) a gate electrode for discharging parasitic electric current.

14. The microelectronic sensor of claim 7, wherein said external memory is a mobile device, desktop computer, server, remote storage, internet storage or telemedicine cloud.

15. The microelectronic sensor of claim 7, wherein said connection module is a wireless connection module for wireless connection of said sensor with the readout module, said readout module comprises another wireless connection module connecting the readout module to the user interface via a digital-to-analogue converter (DAC).

16. A non-invasive method for continuous monitoring of at least one physiological parameter of a patient comprising:
   contacting a single sensing point on the patient's body with, or remotely positioning in a space against the patient's body, the microelectronic sensor of claim 1, said sensor is adapted to contact a sensing point on the patient's body or be remotely positioned in a space against the patient's body;
   continuously recording electrical signals received from the patient's body in a form of a source-drain electric current of said transistor over time with said sensor;
   continuously transmitting the recorded signals from said sensor to the external memory; and
   processing the transmitted signals in the external memory, correlating said IDS dynamics with the physiological parameter and extracting the physiological parameter from said signals in a form of medical data, thereby continuously monitoring said physiological parameter.

17. The method of claim 16, wherein said monitored physiological parameters are a cardiac output and primary heart activity associated with an electrocardiogram (ECG), a central venous pressure (CVP), left and right atrium pressures (LAP and RAP), a heart rate variability (HRV), breath cycle and dynamics, respiratory rate and volume relating to lung or pulmonary activity, a stroke volume, breathing related changes of the stroke volume, peripheral vascular resistance, breathing rate and amplitude (tidal volume), and arterial compliance.

18. The method of claim 16, wherein the step of contacting the single sensing point on the patient's body with the microelectronic sensor is done by fastening a wearable device comprising said microelectronic sensor to the wrist of a patient.

19. The method of claim 16, wherein said single sensing point on the patient's body is a patient's limb selected from an arm, an elbow, a forearm, a wrist, a palm or a finger.

20. The method of claim 16, wherein said microelectronic sensor is contactless and used remotely from a patient's body, being positioned in a space against the patient's body.

21. The sensor of claim 1, wherein said multilayer heterojunction structure comprises:
- A. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or
- B. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or
- C. (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer.

* * * * *